(12) United States Patent
May et al.

(10) Patent No.: US 11,583,642 B2
(45) Date of Patent: Feb. 21, 2023

(54) MEDICINAL INHALER COMPRISING A LOCKOUT OVERRIDE MECHANISM

(71) Applicant: KINDEVA DRUG DELIVERY L.P., St. Paul, MN (US)

(72) Inventors: Robert May, Cambridgeshire (GB); David M. Molony, Cambridgeshire (GB); Iain G. McDerment, Hertfordshire (GB)

(73) Assignee: Kindeva Drug Delivery L.P., St. Paul, MN (US)

( * ) Notice: Subject to any disclaimer, the term of this patent is extended or adjusted under 35 U.S.C. 154(b) by 485 days.

(21) Appl. No.: 16/607,291

(22) PCT Filed: Apr. 25, 2018

(86) PCT No.: PCT/US2018/029332
§ 371 (c)(1),
(2) Date: Oct. 22, 2019

(87) PCT Pub. No.: WO2018/200655
PCT Pub. Date: Nov. 1, 2018

(65) Prior Publication Data
US 2020/0046916 A1 Feb. 13, 2020

(30) Foreign Application Priority Data
Apr. 25, 2017 (GB) .................... 1706504

(51) Int. Cl.
*A61M 15/00* (2006.01)
*A61M 16/00* (2006.01)
(52) U.S. Cl.
CPC ........ *A61M 15/002* (2014.02); *A61M 15/008* (2014.02); *A61M 15/009* (2013.01);
(Continued)

(58) Field of Classification Search
CPC ...... A61M 15/00; A61M 15/002–0026; A61M 15/0068; A61M 15/008–0083;
(Continued)

(56) References Cited

U.S. PATENT DOCUMENTS

| 5,394,866 A | * | 3/1995 | Ritson | ................... | A61M 15/00 128/200.14 |
| 6,637,432 B2 | | 10/2003 | Wakefield | | |

(Continued)

FOREIGN PATENT DOCUMENTS

| EP | 1229953 | 11/2006 |
| GB | 2262452 | 6/1993 |

(Continued)

OTHER PUBLICATIONS

International Search Report for PCT International Application No. PCT/US2018/29332, dated Jul. 20, 2018, 3 pages.

*Primary Examiner* — Rachel T Sippel
*Assistant Examiner* — Jacqueline M Pinderski
(74) *Attorney, Agent, or Firm* — Mueting Raasch Group

(57) ABSTRACT

A refill assembly configured to be removably coupled to a reusable assembly of a medicinal inhaler is disclosed and includes a patient port, a canister actuable by the reusable assembly to deliver a dose of medicament to the patient port, and a sleeve which is selectively actuable by a user independently of the reusable assembly so as to act on the canister to deliver a dose of medicament. The refill assembly further includes an override element which engages the sleeve, the override element being moveable from a first position in which the sleeve is retained in a first position by the override element and a second position in which the sleeve is permitted to move to a second position upon depression of the sleeve by a user to cause a dose of medicament to be delivered to the patient port.

20 Claims, 42 Drawing Sheets

(52) U.S. Cl.
    CPC ............ *A61M 2016/0015* (2013.01); *A61M 2205/123* (2013.01); *A61M 2205/27* (2013.01); *A61M 2205/3569* (2013.01); *A61M 2205/3584* (2013.01); *A61M 2205/52* (2013.01)

(58) Field of Classification Search
    CPC ............................. A61M 15/009–0098; A61M 2016/0015–0024; A61M 2205/123; A61M 2205/27; A61M 2205/3569; A61M 2205/3584; A61M 2205/52; A61M 2016/0021; A61M 2016/0027; A61M 2205/103; A61M 2205/106; A61M 2205/276; A61M 2205/332; A61M 2205/3334; A61M 2205/3553; A61M 15/0026; A61M 2205/3561; A61M 2205/3592; A61M 2205/505; A61M 2205/583; A61M 2205/8212
    See application file for complete search history.

(56) References Cited

U.S. PATENT DOCUMENTS

| | | | |
|---|---|---|---|
| 7,219,664 B2 | 5/2007 | Ruckdeschel | |
| 8,082,918 B2 | 12/2011 | Jansen | |
| 8,381,719 B1* | 2/2013 | Lawrence | A61M 15/009 128/200.23 |
| 2003/0000524 A1* | 1/2003 | Anderson | A61M 15/0028 128/203.23 |
| 2004/0025874 A1* | 2/2004 | Seppl | A61M 15/0081 128/203.15 |
| 2006/0243275 A1 | 11/2006 | Ruckdeschel | |
| 2007/0119450 A1 | 5/2007 | Wharton | |
| 2008/0156321 A1 | 7/2008 | Bowman | |
| 2011/0017210 A1* | 1/2011 | Sugianto | A61M 15/0076 128/203.12 |
| 2020/0086069 A1* | 3/2020 | Riebe | A61M 15/009 |

FOREIGN PATENT DOCUMENTS

| | | |
|---|---|---|
| GB | 2263068 | 7/1993 |
| WO | WO 2001-34231 | 5/2001 |
| WO | WO 01/45768 A2 | 6/2001 |
| WO | WO 2006-064159 | 6/2006 |
| WO | WO 2017-015303 | 1/2017 |
| WO | WO 2017-112400 | 6/2017 |
| WO | WO 2017-176693 | 10/2017 |
| WO | 2018200431 | 11/2018 |

* cited by examiner

MEDICINAL INHALER COMPRISING A LOCKOUT OVERRIDE MECHANISM

CROSS REFERENCE TO RELATED APPLICATIONS

This application is a national stage filing under 35 U.S.C. 371 of PCT/US2018/029332, filed Apr. 25, 2018, which claims the benefit of United Kingdom Patent Application No. GB1706504.6, filed Apr. 25, 2017, the disclosure of which is incorporated by reference in its/their entirety herein.

FIELD

This present disclosure generally relates to medical inhaler refill assemblies comprising a lockout override mechanism, and specifically, but not exclusively, to medicinal inhalers comprising such a refill assembly and a reusable assembly.

BACKGROUND

Delivery of aerosolized medicament to the respiratory tract for the treatment of respiratory and other diseases is conventionally done using inhalers of either the pressurized metered dose inhaler (pMDI), the dry powder inhaler (DPI) or the nebulizer type. pMDI inhalers in particular have become an industry standard, and are familiar to many patients who suffer from either asthma or from chronic obstructive pulmonary disease (COPD). Conventional pMDI devices comprise an aluminum canister, sealed with a metering valve, which contains the medicament formulation. Generally, the medicament formulation is a pressurized formulation containing either fine particles of one or more medical compounds suspended in a liquefied hydrofluoroalkane (HFA) propellant, or a solution of one of more medicinal compounds dissolved in a propellant/co-solvent system. Formulations incorporating one drug in solution and another one in suspension form are also known.

In a conventional pulmonary pMDI, the sealed canister is provided to a patient in an actuator. The actuator is conventionally a generally L-shaped plastic molding comprising a general cylindrical vertical tube that surrounds the canister plus a generally horizontal tube that forms a patient port (e.g., a mouthpiece or nosepiece) that defines an inspiration orifice. To use such an inhaler, the patient exhales, places the patient port into a body cavity (e.g., a mouth or nose) and then inhales to draw air through the inspiration orifice. The majority of such inhalers are of the pulmonary "press-and-breathe" type, where the patient must press down on the protruding end of the canister in order to operate the metering valve to release a metered dose of medicament in order to operate the metering valve to release a metered dose of medicament from the canister into the inhaled air stream and thence through the mouthpiece into their lungs. This requires a significant degree of coordination of timing of inhalation and dose release if the emerging cloud of aerosolized medicament is to be taken far enough into the lungs to provide maximum therapeutic benefit. If the patient releases the dose before inspiratory flow has been established, then a proportion of the drug is likely to be lost in the mouthpiece or the patient's mouth. Conversely, if released much after the start of inhalation, then the deeper regions of the lungs might already be full of air and not penetrated by the following bolus of released medicament aerosol.

Spacer device have previously been devised which fit onto the mouthpiece of a pMDI in order to reduce the velocity of the emergent plume of medicament aerosol and to provide a volume in which it can expand and its propellant can evaporate more completely. This serves to avoid some of the problems of coordination and also avoids the tendency for high throat deposition caused by excessively fast drug particle inhalation. However, spacer devices are very bulky, and they can retain an excessive proportion of drug on their walls, thereby reducing the dose that reaches the patient. Spacer devices can also be highly sensitive to electrostatic charge, which can often be strongly affected by the way in which they are washed and dried.

To overcome what can be quite a challenge for some patients, pMDI device designs have been created that employ automatic breath-actuated triggering, releasing a dose only in response to the patient's inhaled breath. The AUTOHALER™ metered dose inhaler, available from 3M Company, St. Paul, Minn., and the EASIBREATHE™ inhaler, available from Teva Pharmaceutical Industries Ltd., Israel, are two such pMDI devices that use breath-actuation to attempt to better coordinate dose release with inhalation.

Due to the relatively high cost of such devices compared to conventional pMDI devices it is known to provide an inhaler formed of a reusable assembly (which includes much of the relatively expensive hardware and electronics) and a refill assembly which includes the canister of medicament and the patient port.

SUMMARY

Whilst breath-actuated inhalers of the type described above present significant advantages to the user, it is recognized that from time to time the breath actuated triggering mechanism may be lost by the user of may fail. Such a failure may be a result of damage or misuse of the device or some other failure mode as may occur during manufacturing.

In the event of such a failure it is imperative that the user of the device is still able to receive the prescribed dose of medicament by bypassing the breath-actuation to manually administer the medicament.

In the event that the inhaler is formed of a reusable assembly and a refill assembly a user must also be prevented from reattaching the reusable assembly and the refill assembly as it is not desirable for the dose counter to continue counting doses once a dose has been manually administered (and therefore not counted by the dose counter). It is conceivable in such circumstances that the canister could be emptied before the dose counter indicates that the canister is nearing the end of its life.

It is therefore an object of the invention to at least mitigate some of the problems set about above.

Accordingly, a first aspect of the invention provides a refill assembly for use in a medicinal inhaler, the refill assembly being configured to be removably coupled to a reusable assembly of a medicinal inhaler, the refill assembly comprising:
  a patient port;
  a canister actuable by the reusable assembly to deliver a dose of medicament to the patient port,
  a sleeve which is selectively actuable by a user independently of the reusable assembly so as to act on the canister to deliver a dose of medicament,
  the sleeve having a first position in which the sleeve cannot be actuated to cause a dose of medicament to be released from the canister and a second position in which the sleeve is actuable to cause a dose of medicament to be delivered to the patient port;
the refill assembly further comprising:
an override element which engages the sleeve,
the override element being moveable from a first position in which the sleeve is retained in its first position by the override element and a second position in which the sleeve is permitted to move to its second position upon depression of the sleeve by a user.

Advantageously, the provision of an override element allows the user of the device to administer a dose of medicament in the event of loss of, or damage to, the reusable assembly. This presents significant clinical benefit to the user who is in a position to maintain their treatment regime whilst medical professionals are contacted to remedy the loss of, or damage to, the reusable assembly.

Preferably, the canister is actuable in the absence of the reusable assembly by depression of the sleeve by the user with the override element in its second position.

Preferably, the override element is movable from its first position to its second position and cannot be moved from its second position to its first position.

Advantageously, this element of the invention ensures that once the refill assembly is in its override condition it cannot be returned to its normal condition. This is advantageous as any dose administered by the refill assembly in its override condition would not be counted by a dose counter in the reusable assembly. Ensuring that the refill assembly remains in the override condition allows the prevention of subsequent reassembly to the reusable assembly. This avoids the situation where the dose counter displays fewer doses than have in fact been administered from the canister.

Preferably, the sleeve is configured to receive at least a portion of a canister, the canister comprising a medicament and a dose release valve, the sleeve movable between its first position in which the dose release valve is not actuated to release a dose of medicament and its second position in which the dose release valve is actuated to release a dose of medicament.

Preferably, the override element is configured to rotate between its first and second positions.

Preferably, the sleeve defines a protrusion for selectively engaging the override element.

Preferably, the protrusion engages an abutment on the override element when the sleeve and override element are in their respective first positions to prevent movement of the sleeve from its first position.

Preferably, the protrusion disengages from the abutment on the override element when the override element is moved from its first position to its second position permitting movement of the sleeve from its first position to its second position upon depression of the sleeve by a user.

Preferably, the sleeve has a cylindrical body and the protrusion is defined by at least one leg which extends from the cylindrical body.

Preferably, the abutment is defined by at least one ledge which is aligned with, and engages with, the at least one leg on the sleeve when the sleeve and override element are in their respective first positions.

Preferably, the sleeve defines 3 legs and the override element defines 3 ledges, wherein the three legs are respectively aligned with the three ledges when the sleeve and override element are in their respective first positions.

Preferably, the override element includes a boss which is operable by the user to move the override element from its first position to its second position.

According to a second aspect of the invention there is provided an inhaler comprising:
the refill assembly of the first aspect of the invention; and
a reusable assembly,
wherein the reusable assembly is configured to be coupled to the refill assembly, the reusable assembly comprising a dose release firing system configured to act on the canister to deliver the dose of medicament.

Preferably, the refill assembly is releasable from the reusable assembly after it has been coupled to the reusable assembly.

Preferably, the dose release firing system is breath-actuated.

The invention will now be described by way of example only and with reference to the following drawings.

DETAILED DESCRIPTION

Figure 1:
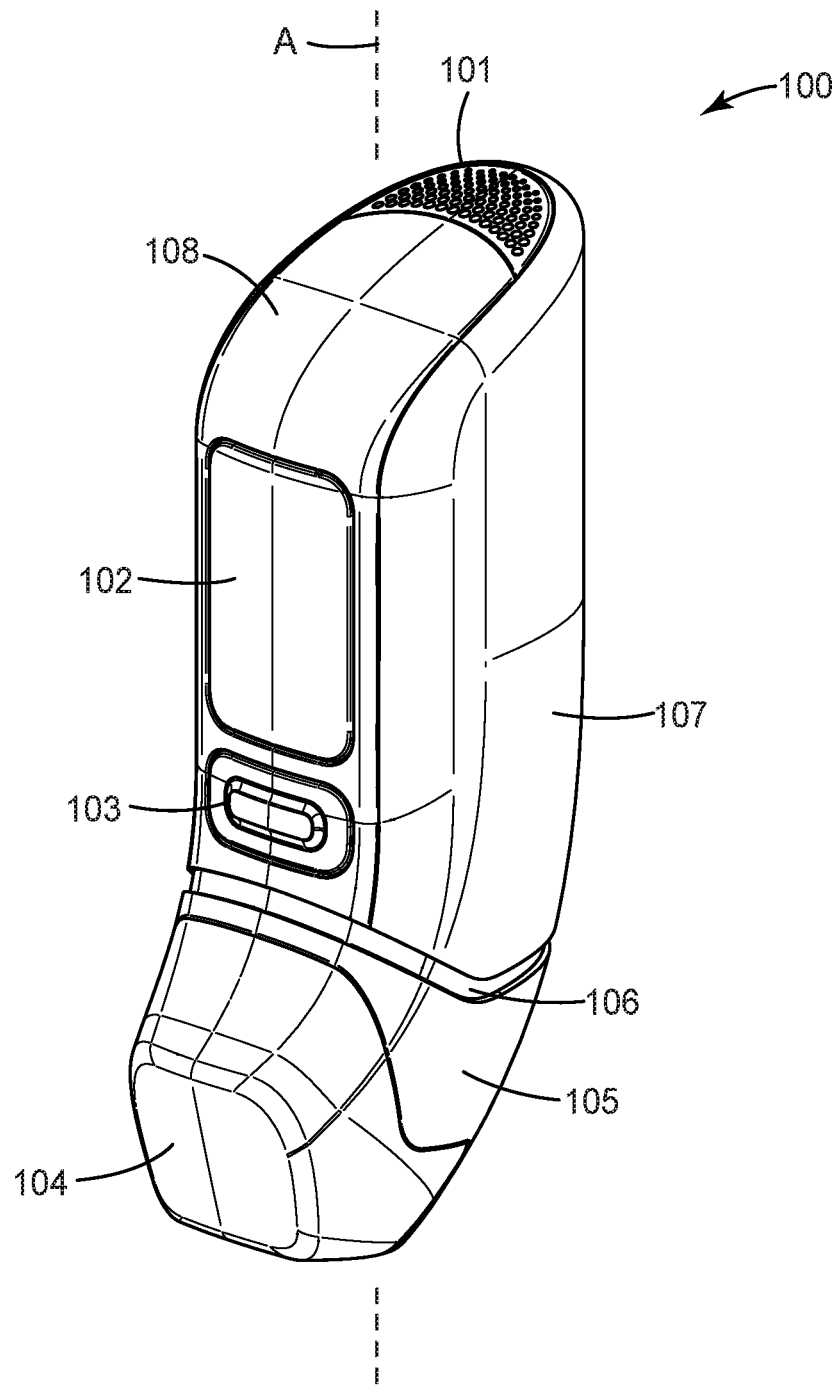
FIG. 1 is a front isometric view of a medicinal inhaler according to the present invention, the inhaler comprising a reusable assembly and a refill assembly, the inhaler shown assembled.
Figure 2:
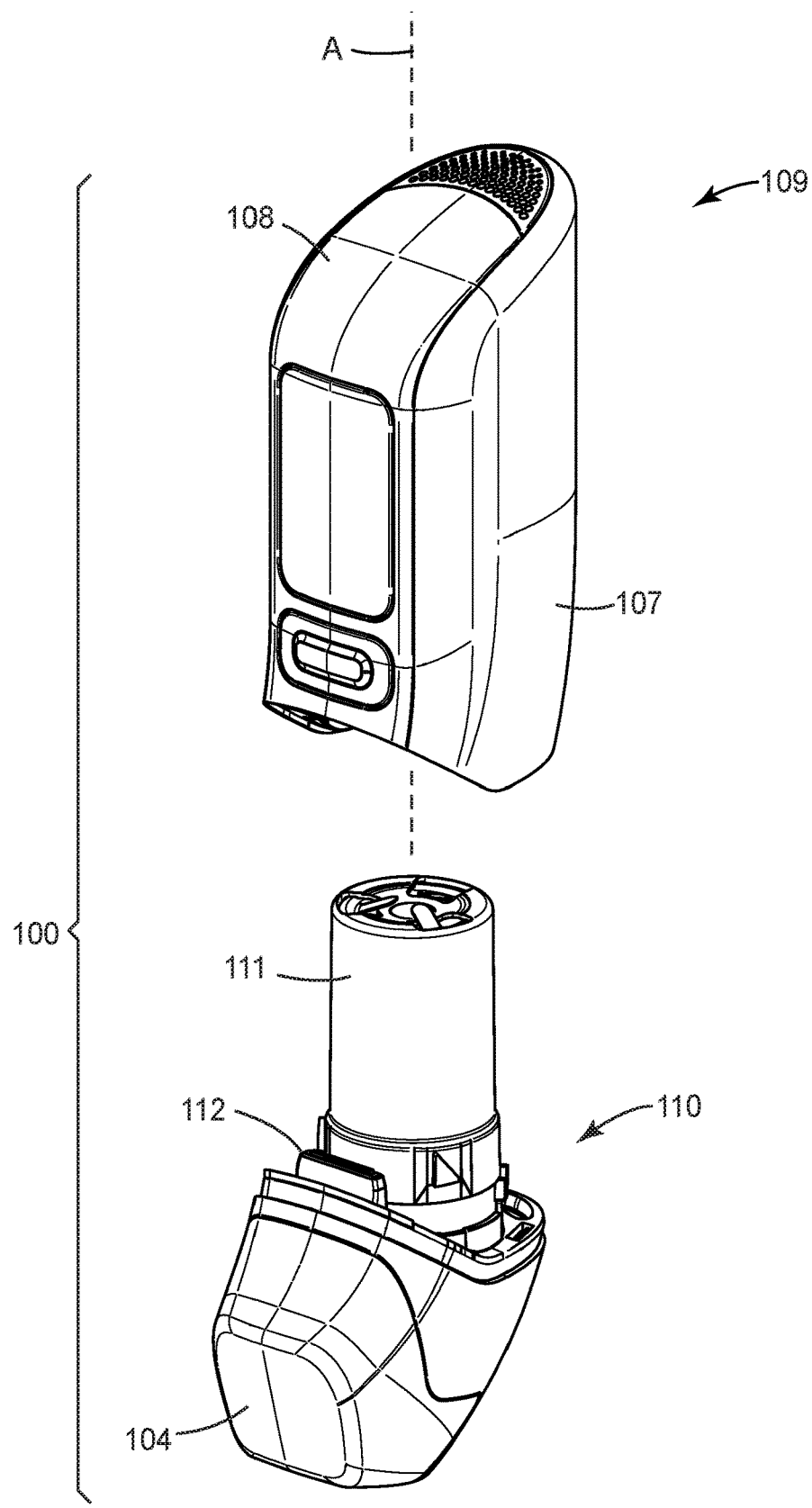
FIG. 2 is an exploded front isometric view of the inhaler of FIG. 1.
Figure 2A:
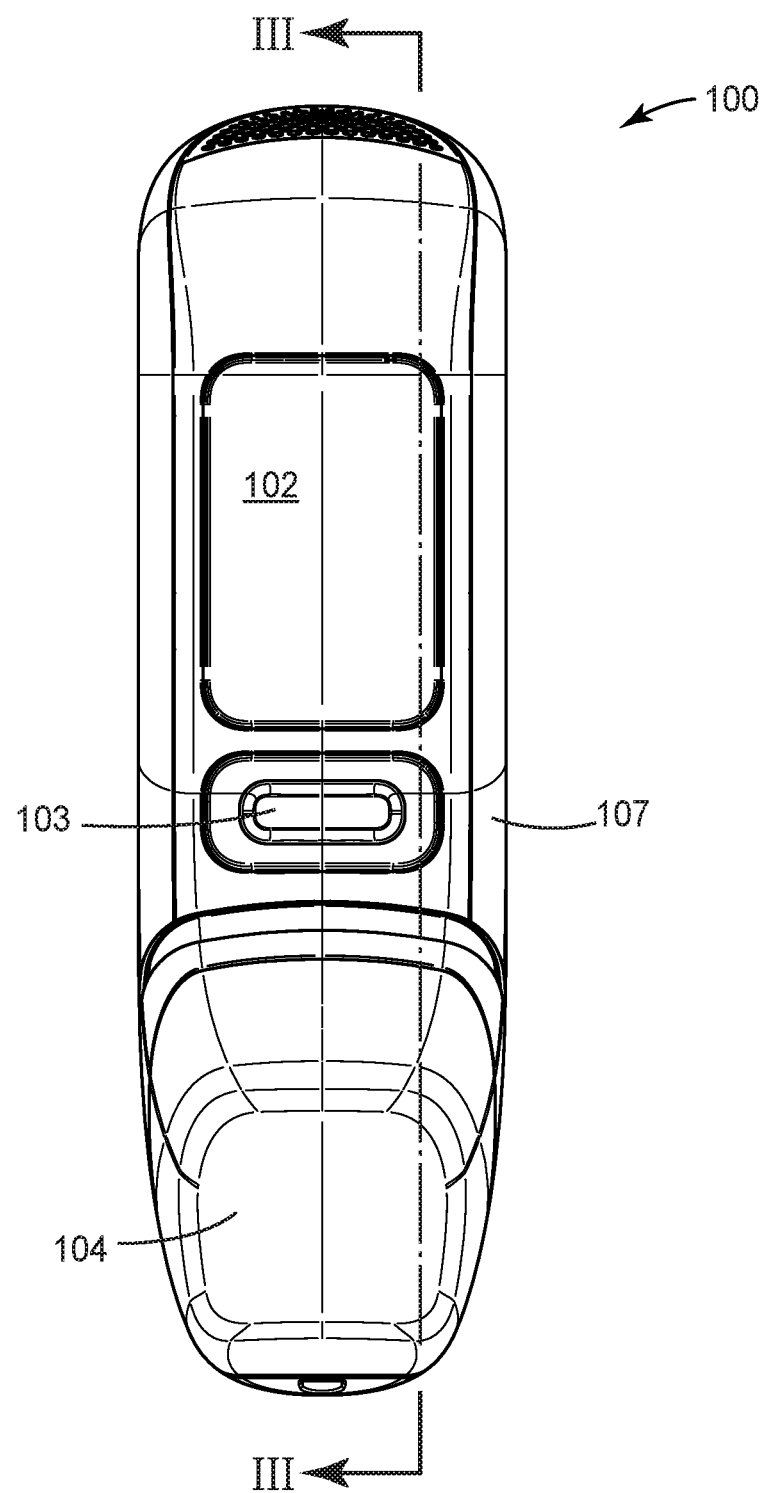
FIG. 2A is a front view of the inhaler of FIG. 1.
Figure 2B:
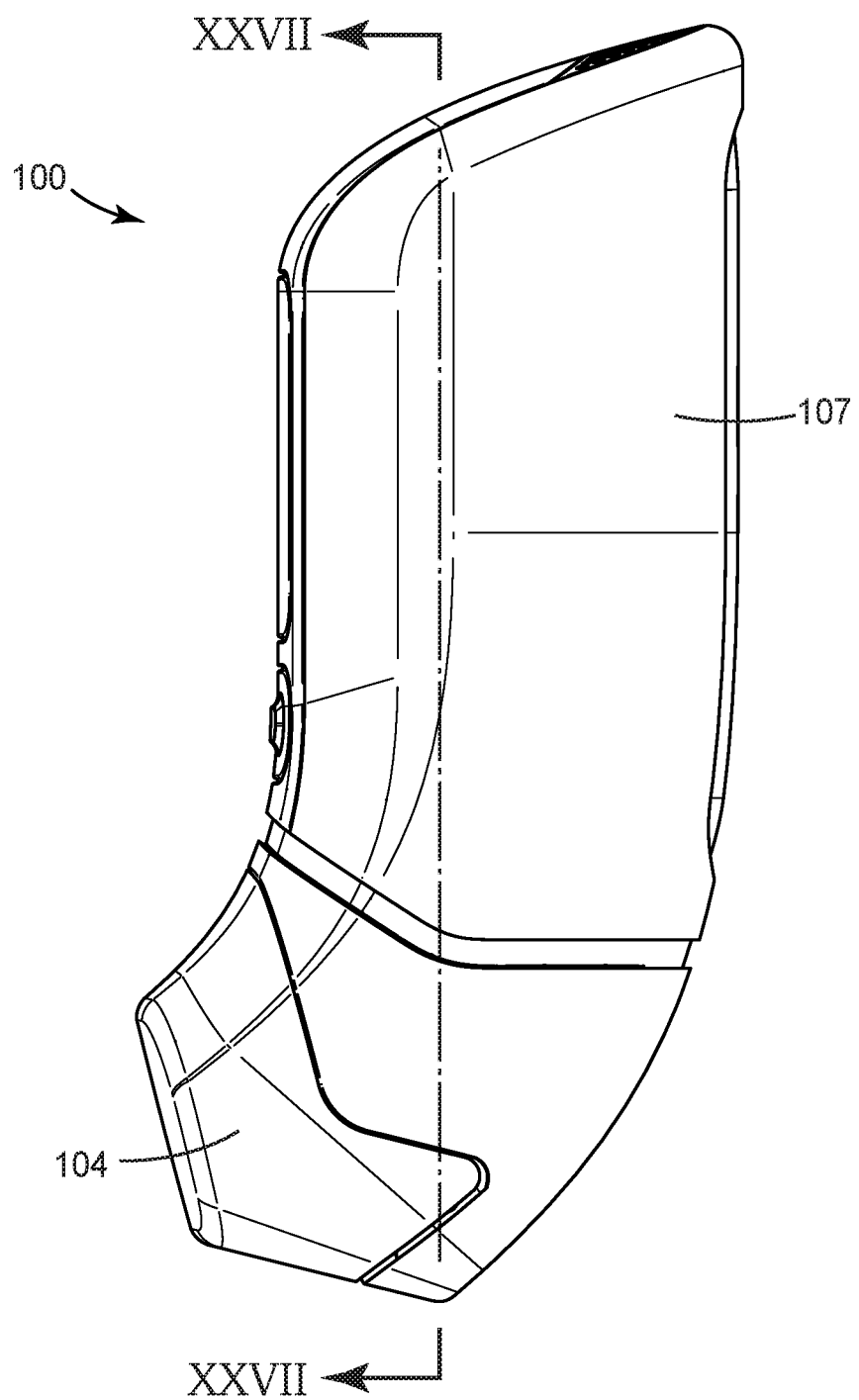
FIG. 2B is a side view of the inhaler of FIG. 1.

As shown in FIGS. 1 and 2, the inhaler 100 has a reusable assembly 109 and a refill assembly 110.

The inhaler 100 (or a portion thereof, such as the reusable assembly 109 and/or the refill assembly 110) has a longitudinal axis A that defines an axial direction that extends along or substantially parallel to the axis. The refill assembly 110 and reusable assembly 109 are coupled together by moving the refill assembly 110 and the reusable assembly 109 toward one another in the axial direction (e.g., along the axis A).

The inhaler 100 has an air inlet (or aspiration orifice) 101, a display screen 151 and a display screen cover 102, a control button 103, a patient port cover (e.g., a mouthpiece cover) 104, an actuator assembly 105, an air sealing cap 106, a rear outer housing 107 and a front outer housing 108. By way of example, the air inlet 101, the display cover 102, the control button 103, the rear outer housing 107 and the front outer housing 108 are shown as forming a portion of the reusable assembly 109, and the patient port cover 104, the actuator assembly 105 and the air sealing cap are shown as forming the refill assembly 110. The air inlet 101 may include a grill, a screen or grate positioned to inhibit debris from entering the air inlet 101.

Referring now to FIGS. 2 to 4B, the refill assembly 110 includes a sleeve 111 dimensioned to receive a medicament canister 114, a patient port cover 104, an actuator assembly 105, an air sealing cap 106, a biasing element in the form of spring 113, an override element 115, a resilient element in the form of spring 116, a patient port cover linkage 117, a stem post assembly 118 and a refill memory device 112. The memory device 112 is configured to be operatively coupled to a controller 149 which is located in the reusable assembly 109.

The reusable assembly 109 includes a grille 119, a cover switch linkage 120, a rocker plate 121, a lead screw 122, a follower 123, a chassis 124, two biasing elements (e.g., springs) 125, a clip 126, an air flow path 127, an air flow path funnel 128, a motor assembly 129 (e.g., an electric motor with a gear box attached and an axle), a pinion gear 130, a bridge 131, an electronics assembly 132, the display cover 102, the rear outer housing 107 and the front outer housing 108. The reusable assembly 109 includes a reusable air flow path 127 and a flow governor 140 positioned in the reusable air flow path 139.

Various features of the refill assembly 110 and reusable assembly 109 and how they interact or engage to prevent the use of the refill assembly 110 when not coupled to the reusable assembly 109 are described in greater detail below.

Figure 5:
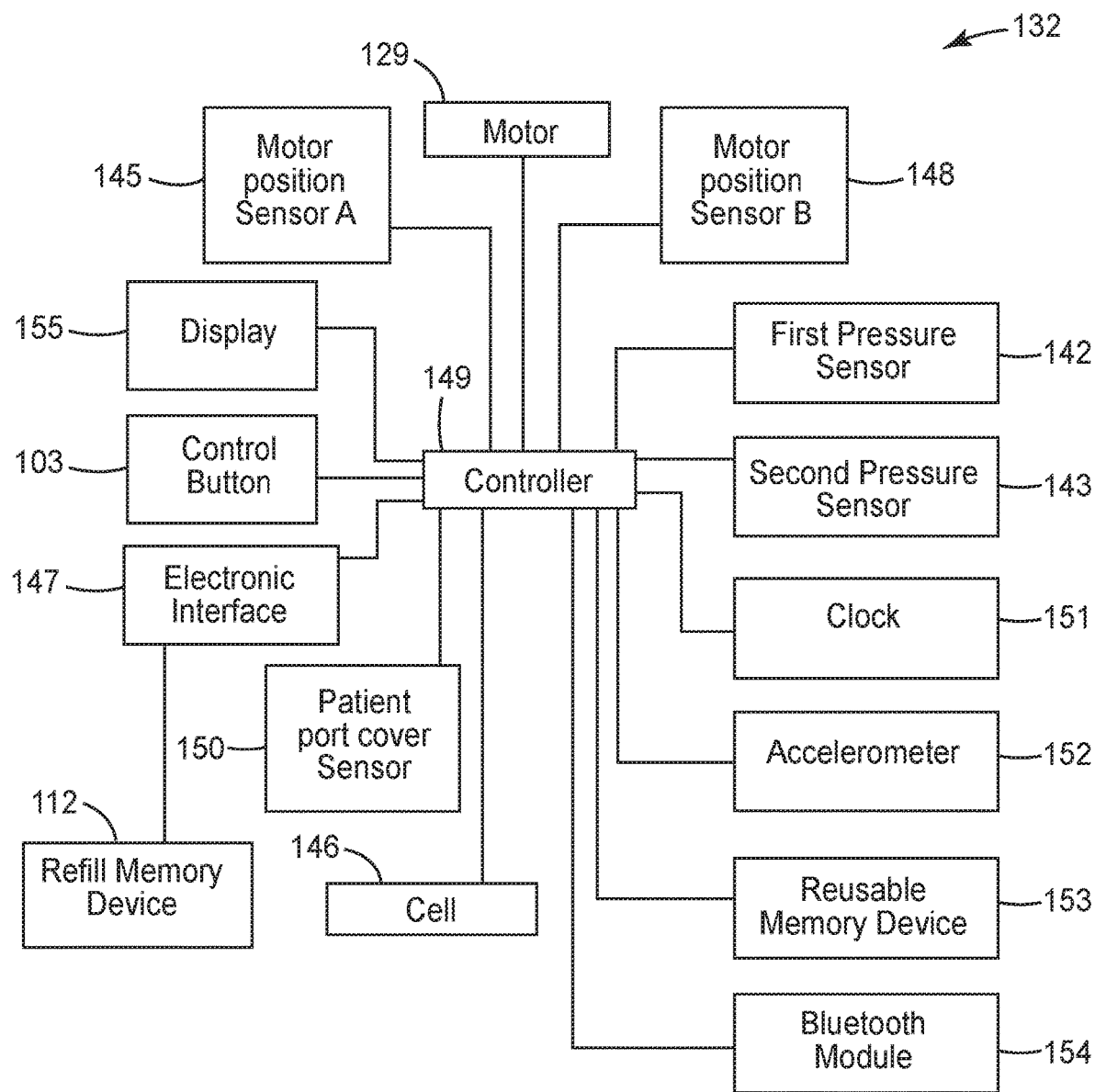
FIG. 5 is a schematic block diagram of the inhaler of FIG. 1.
Figure 6:
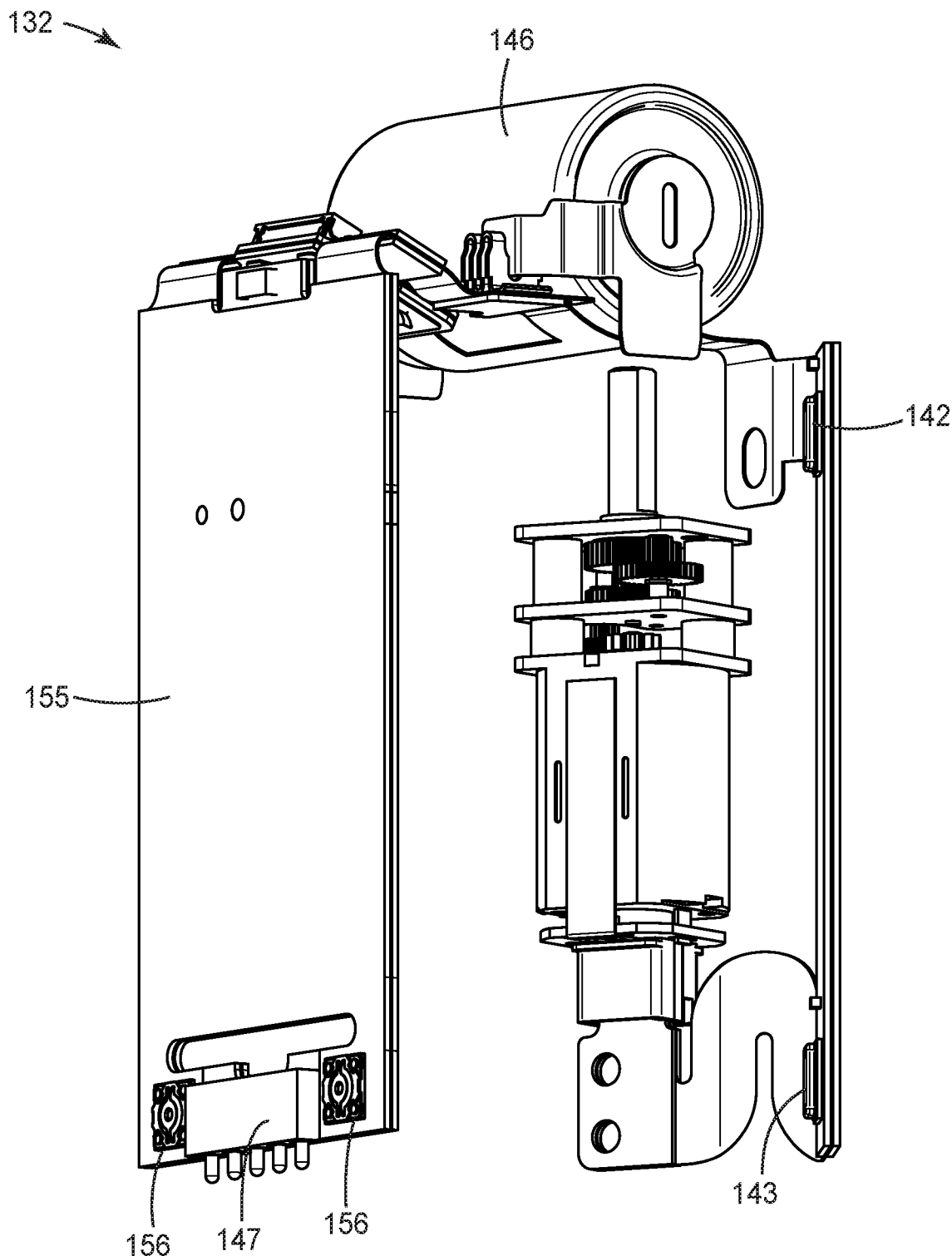
FIG. 6 is a front isometric view of the electrical system of the inhaler of FIG. 1.
Figure 7:
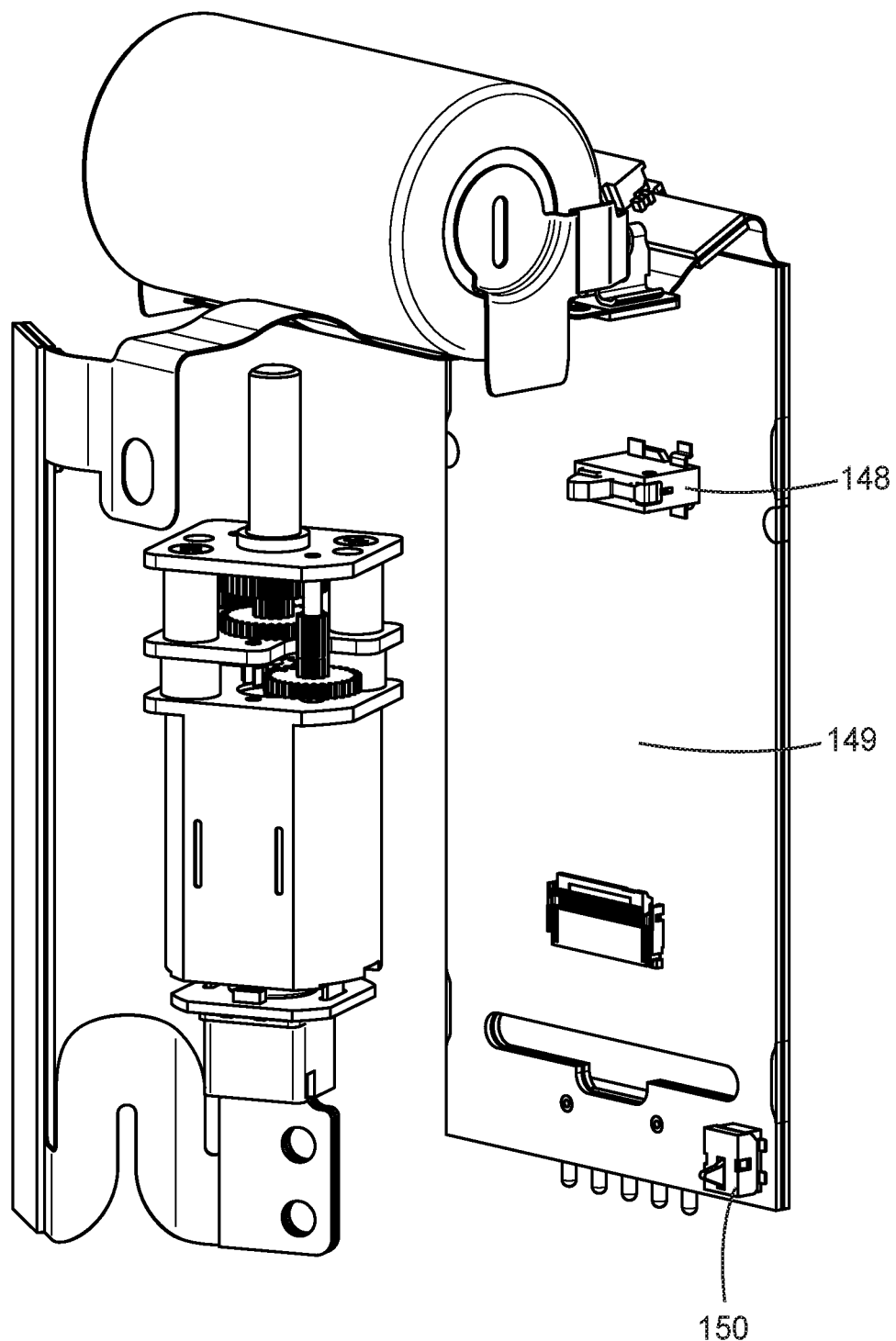
FIG. 7 is a rear isometric view of the electrical system of the inhaler of FIG. 1.

Referring briefly to FIGS. 5 to 7, the memory device 112 of the reusable assembly 110 can connect to an electronic interface 147 connected to a controller 149, to which the control button 103 and the display 155 can also connect. In some embodiments, the display 155 can include a liquid crystal display (LCD) screen. Power can be supplied from an on-board power supply such as a cell 146, which can be connected to the controller 149.

Generally, the controller 149 can be a suitable device such as, for example a programmable logic controller ("PLC"), a microprocessor or the like. As such, the controller may include both hardware and software components, and the term "controller" is meant to broadly encompass the combination of such components.

As shown in FIGS. 5 to 7, the cell 146 can be connected to the controller 149 and can provide power for all of the electronic components of the inhaler 100, or a portion thereof, which can be regulated by the controller 149. In some embodiments, by way of example, the controller 149 can include or be associated with one or more of a clock 151, an accelerometer 152, a memory device 153 and a Bluetooth module 154. The controller 149 can also be connected to a first pressure sensor 142 and second pressure sensor 143, a motor 129 and the electronic interface 147. In addition, the display 155, a patient port cover sensor 150, a motor position sensor A 145 and a motor position sensor B 148 and the memory device 112 (e.g., located in the refill assembly) can be connected to the controller 149. As mentioned above, in some embodiments the Bluetooth module 154 can be located in, or can form a portion of, the reusable assembly, and the Bluetooth module 154 can enable sharing of various information (e.g., the usage data of the inhaler 100) with a health care professional.

The flow governor 140 can be adapted to change its geometry, and thereby its resistance to air flow, as a function of pressure drop between its inlet and its outlet. The flow governor 140 can therefore provide a means of governing the air flow rate (i.e., volumetric flow rate) through the inhaler 100 to reduce inter-patient and intra-patient inhalation variability and provide a more reproducible level of drug deposition in the lung.

The flow governor 140 includes (i) a tubular element that defines at least a portion of an air flow path therewithin, the tubular element comprising one or more flexible walls configured to flex (or collapse) inwardly in response to an air flow in the air flow path, and (ii) an internal support structure located within the tubular element and configured (e.g., shaped, dimensioned, positioned and having desired material properties) to preserve at least a predetermined cross-sectional area of the air flow path within the tubular element when the one or more flexible walls of the tubular element are flexed (or collapsed) inwardly.

As a result, part of the air flow path cross-sectional area remains open even when the tubular element has collapsed, in order to allow the continued inhalation of air and emitted medicament. A "predetermined cross-sectional area of the air flow path within the tubular element" can include a portion of the air flow path that passes through the internal support structure, e.g. when the internal support structure includes one or more solid portions or components, as well as a cross-sectional area of space between the tubular element and the internal support structure. The material makeup of the tubular element flexible walls can also be chosen to achieve the desired cross-sectional area between the tubular element and the internal support structure.

The controller 149 and the pressure sensors 142 and 143 form at least a portion of an inspiratory air flow detection system that can provide an electrical signal that is used to activate an electromechanical firing mechanism to cause a dose of medicament to be released (described in further detail below) according to a defined algorithm.

During this inspiratory process, the flow governor 140 ensures that the inhalation is governed to within a desired range of flow rates. After delivery of the dose, the controller 149 can communicate with the memory device 112, such that data are written to the memory device 112 indicating that a dose has been delivered. The inhaler 100 can also be capable of capturing other data, such as the patient's inhalation profile and the time/date that the dose was taken, e.g., as derived from the clock 151.

Additionally, the presence of the accelerometer 152 (e.g., a three axis accelerometer) can allow capture of data relating to the force and duration of the shake performed by the patient prior to taking a dose of medicament and the orientation of the inhaler 100 during medicament dosing. These data can also be written to the memory device 112 of the refill assembly 110 and/or can be written to the memory device 153 associated with the controller (See FIG. 5).

Referring once again to FIG. 3, the actuator assembly 105 includes a patient port 133 and a stem post assembly 118 with a spray orifice 134 in it. The patient port 133 is shown as being in the form of a mouthpiece that defines an inspiration orifice (or an air outlet). Such a patient port of an inhaler is sometimes referred to herein as a "mouthpiece" for simplicity. However, it should be understood that such patient ports can instead be configured to be nosepieces of nasal inhalers and that the present disclosure can equally apply to nasal inhalers even when not specifically mentioned herein.

The refill assembly 110 includes a refill air flow path 135. The refill air flow path 135 is shown as being defined in the refill assembly 110 between the actuator assembly 105 and the air sealing cap 106. The refill air flow path 135 and the reusable airflow path 139 can be connected when the refill assembly 110 is coupled to the reusable assembly 109 (e.g., to form the inhaler 100), so that they form an air tight seal. As a result, when suction, e.g., patient inhalation, is applied at the patient port 133, air can only enter through the air inlet 101.

Figure 3:
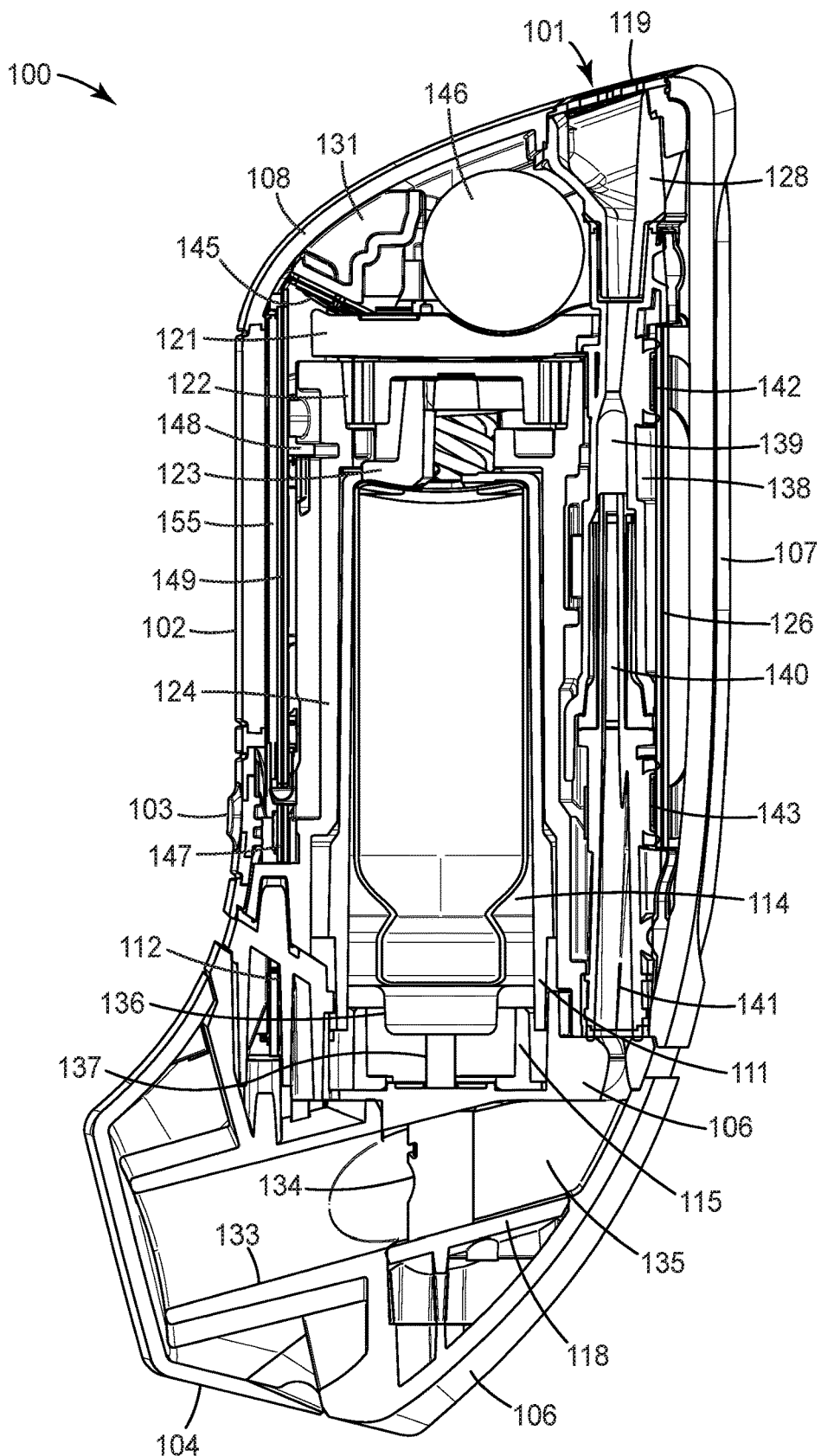
FIG. 3 is a side cross-sectional view of the inhaler of FIG. 1 taken along line of FIG. 2A.

The inhaler 100, and particularly the refill assembly 110, includes or can be configured to house or employ the medicament canister 114 containing a medicament formulation. The canister 114 is illustrated in FIG. 3 as being a pressurized metered dose inhaler (pMDI) canister, including a valve 136 having a stem 137 that can be seated in the stem post assembly 118. The canister 114 is positioned in (e.g., enveloped by) the override element 115 and the sleeve 111 (FIGS. 2 to 4), which can be dimensioned to receive at least a portion of the canister 114 and can include an annular shape or an annular portion.

The sleeve 111 is configured to be received within at least a portion of the housing of the reusable assembly 109, within the outer housing, comprising the front outer housing 108 and the rear outer housing 107 and, particularly, within at least a portion of an inner housing 124 of the reusable assembly 109. The inner housing can also be referred to as the chassis 124. The features of the chassis 124 and the front outer housing 108 and the rear outer housing 107 are described in greater detail below.

The inhaler 100, and specifically the reusable assembly 109, includes an electromechanical firing mechanism. In the illustrated embodiment, the element that drives the firing mechanism is a motor 129, to which a pinion gear 130 is connected, which in turn engages a lead screw 122. A follower 123 is connected to the lead screw 122 so that drive from the motor 129 brings about axial travel of the follower 123. Various electronic components contribute (as described previously with reference to FIG. 5) to defining when the motor 129 starts to drive the firing mechanism, when the firing mechanism has reached full axial travel, and when the motor 129 returns the firing mechanism back to its starting position. Collectively, in this example, the motor 129, pinion gear 130, lead screw 122, follower 123 and rocker plate form a drive mechanism for mechanically driving the canister to deliver a dose of medicament although it will be appreciated that alternative forms of drive mechanism are conceivable within the scope of the invention.

By employing a refill assembly 110 that can be coupled to the reusable assembly 109, depleted, discarded and replaced with a new refill assembly 110, at least a portion (i.e., the reusable assembly 109) of the inhaler 100 can be reused with consumable refill assemblies 110, providing a cost saving benefit, i.e., the reusable assembly which comprises expensive electronic/electromechanical components can be reused with several refill assemblies. A depleted refill assembly 110 can be recycled. Additionally, refill assemblies 110 of the present disclosure comprising canisters containing different medicaments can be used with the same reusable assembly 109. Therefore, a patient can have several refill assemblies 110, of differing medication, but only require one reusable assembly 109.

Figure 8A:
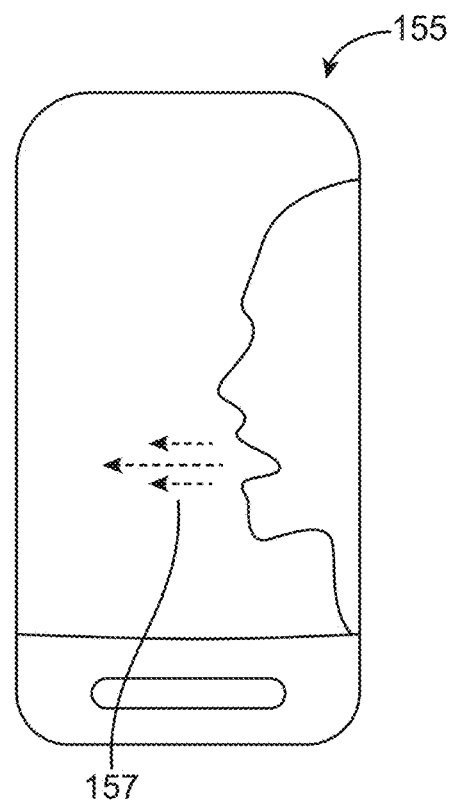
FIGS. 8A, 8B and 8C are front views of a user interface of the inhaler of FIG. 1.
Figure 8B:
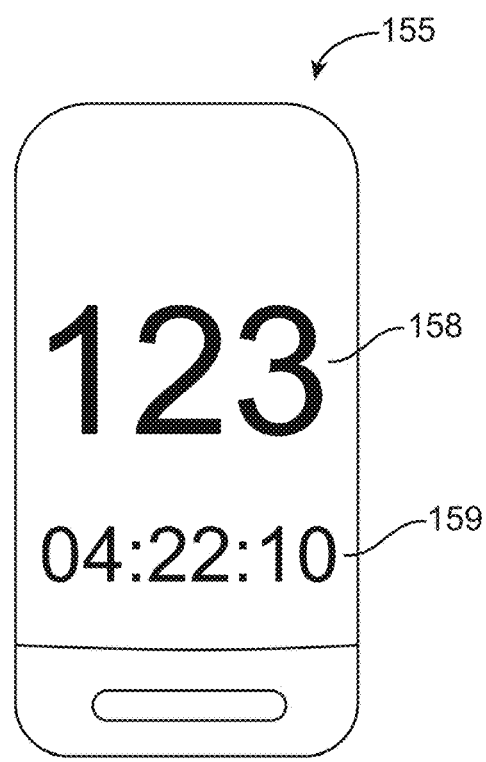
Figure 8C:
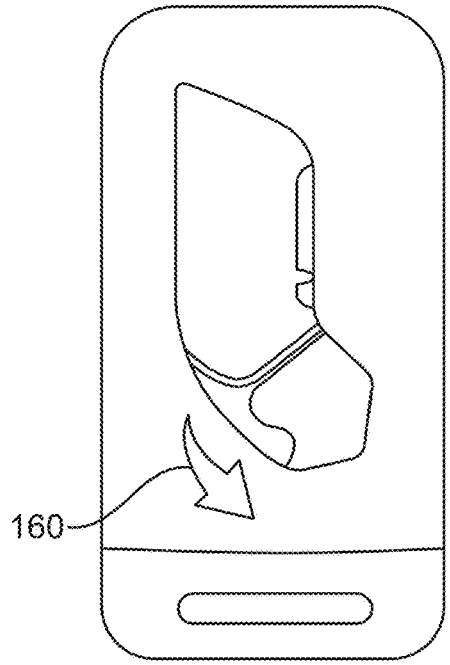

The refill memory device 112 stores information relating to the medicament canister 114. Such information may take the form of medicament type, expiry date, doses remaining, and data relating to the usage of the canister 114 (e.g., inhalation profiles for each dose). By providing a memory device 112 in the refill assembly 110, all pertinent information relevant to the canister 112 of a particular refill assembly 110 can remain with the refill assembly 110. As a result, when the refill assembly 110 is re-coupled to the reusable assembly 109 (e.g., to reform the inhaler 100), the above-described relevant information can be accessed by the patient. By way of example, at least some of such information can be shown on a display (e.g., an LCD screen) 155 (see FIG. 5, described below). FIG. 8A to FIG. 8C provides examples of iconography that may be displayed to the patient on the display 155. FIG. 8A shows an icon on the display 155 of a patient exhaling 157, thus reminding the patient to exhale prior to taking a dose. FIG. 8B shows that the LCD screen 151 can display the remaining number of doses 158 and the elapsed time since the last dose 159 was dispensed. FIG. 8C shows an icon on the display screen 151 of the patient port cover being closed 160. Additional iconography can be used to convey instructions and/or information to the patient at specific time points during their use of the inhaler 100 to aid compliance (competence and adherence) with their dosing technique/regime. Indeed, sequential iconography (e.g. several icons displayed one after the other) can be employed as opposed to static iconography (e.g. one icon) to further convey more complex instructions. Furthermore, alpha-numerical instructions can also be presented to the patient via the display 155, in isolation or in combination with static or sequential iconography.

Figure 9:
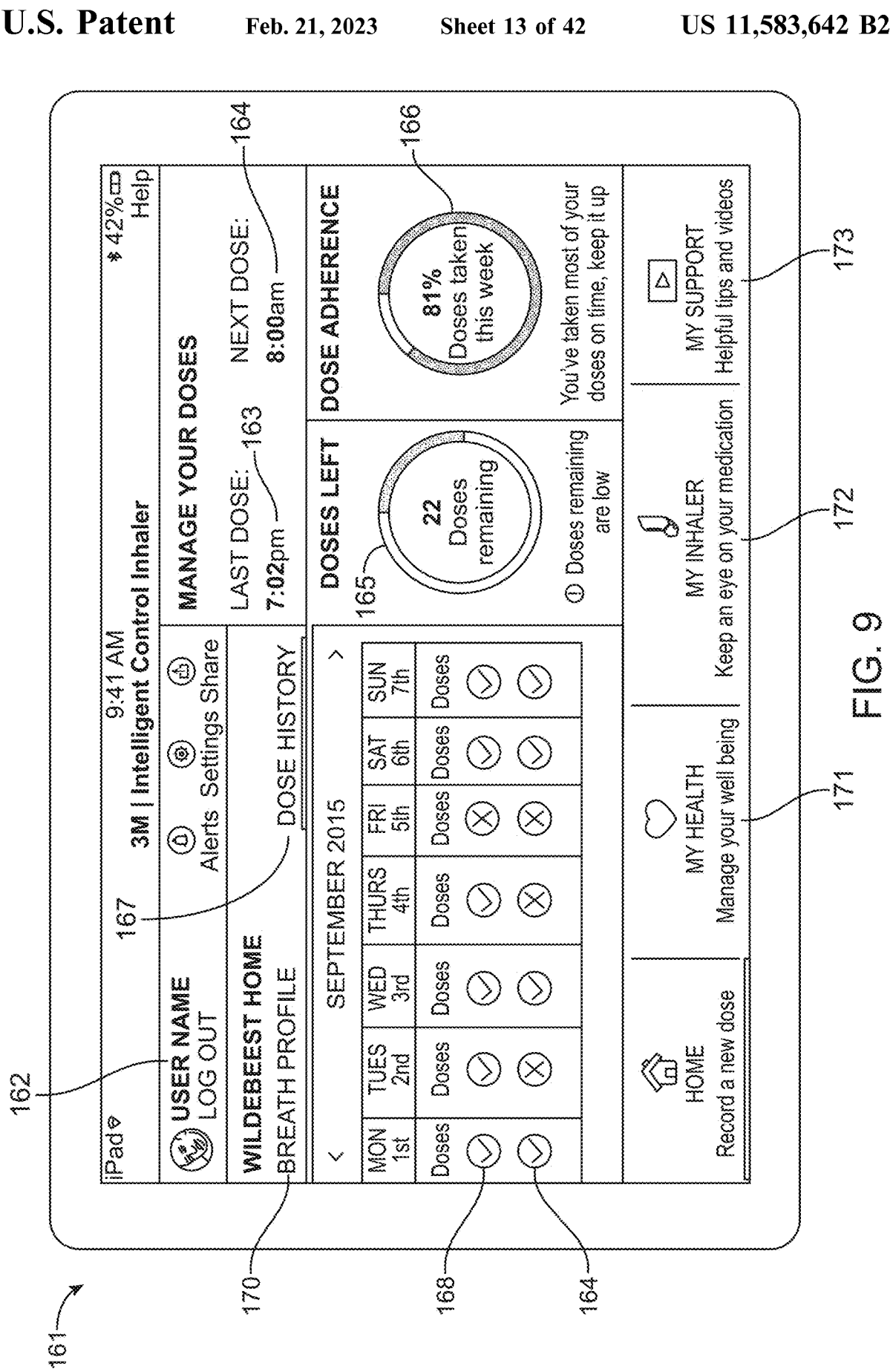
FIG. 9 is a top plan view of a user interface of a supporting app for the inhaler of FIG. 1 shown on a handheld device.

As mentioned previously, the reusable assembly 109 can include a Bluetooth module 154 (see FIG. 5) or wireless of wired data transfer means such that various information (e.g., the usage data) can be shared with a health care professional. The usage data can be reviewed by the healthcare professional and used to aid the treatment of the patient's condition(s). Additionally, the patient usage experience can be enhanced using the Bluetooth module 154 to pair the inhaler 100 with another electronic device, e.g., a smartphone or tablet with a specific software "application" or a personal computing device with specific software. Furthermore, it is also possible for the inhaler 100 to communicate with an intermediary device (e.g., wearable technology such as an electronic wrist band or waist-worn device) that can have similar functionality to a smartphone, a tablet or a personal computing device. Such applications or software can comprise features that aid the patient. FIG. 9 shows a tablet 161 which using an appropriate application can process data received from the inhaler 100 via Bluetooth communication between the inhaler 100 and the tablet 161.

The application can display the patient's name 162, time of last dose 163, time for next dose 164, number of doses remaining in a particular refill 165, dose adherence 166, dose history 167 for a specified time range, and/or further indication as to whether a dose was missed 168 or whether a dose had been taken 169. Additionally, through accessing other menus of the application, other data/information can be accessed, for example breath profile data 170, information about the patient's health 171 (e.g., the patient's mood on particular days, data from other electronic devices e.g., breathing/blood pressure, heart rate, etc.), inhaler information 172 (e.g. number/type of refill assemblies used; when a replacement reusable assembly 109 is required), and support functions 173 (e.g., tips on how to use an inhaler, encouragement on staying active, etc.). Thus information and data are provided to the patient to allow them to review their medicament usage, aid them with reaching compliance with their prescribed dosing regimen, and offer them additional training/support.

Furthermore, a similar application can be provided to a healthcare professional so that they are able to review the patient's data to aid with treatment of the patient. The version of the application, or software, used by the healthcare professional can have additional functionality for analyzing and interpretation of the data to help better manage the patient's condition(s). Indeed, multiple versions of the application, or software, are possible each to suit the needs of a specific user type, for example a healthcare provider.

It is important that the refill assembly 110 can only be used when it is coupled with the reusable assembly 109, e.g., to form the inhaler 100. That is to say, it is important that the refill assembly 110, when not coupled with the reusable assembly 109, precludes actuation of the canister 114 by a user and that delivery of medicament can only be achieved through the coupling of the refill assembly 110 with the reusable assembly 109 (e.g., to form the inhaler 100). That can be important for various reasons or can be useful for various scenarios.

For example, if a dose of medicament were to be delivered when the refill assembly 110 was not coupled to a reusable assembly 109 (e.g., accidentally during transportation or handling of the refill assembly 110), a record of this would not be written to (stored in) the refill memory device 112 of the refill assembly 110. Therefore, when the refill assembly 110 was subsequently coupled to a reusable assembly 109, the count displayed would be inaccurate, potentially leading to a situation where the patient might run out of medication.

Figure 38:
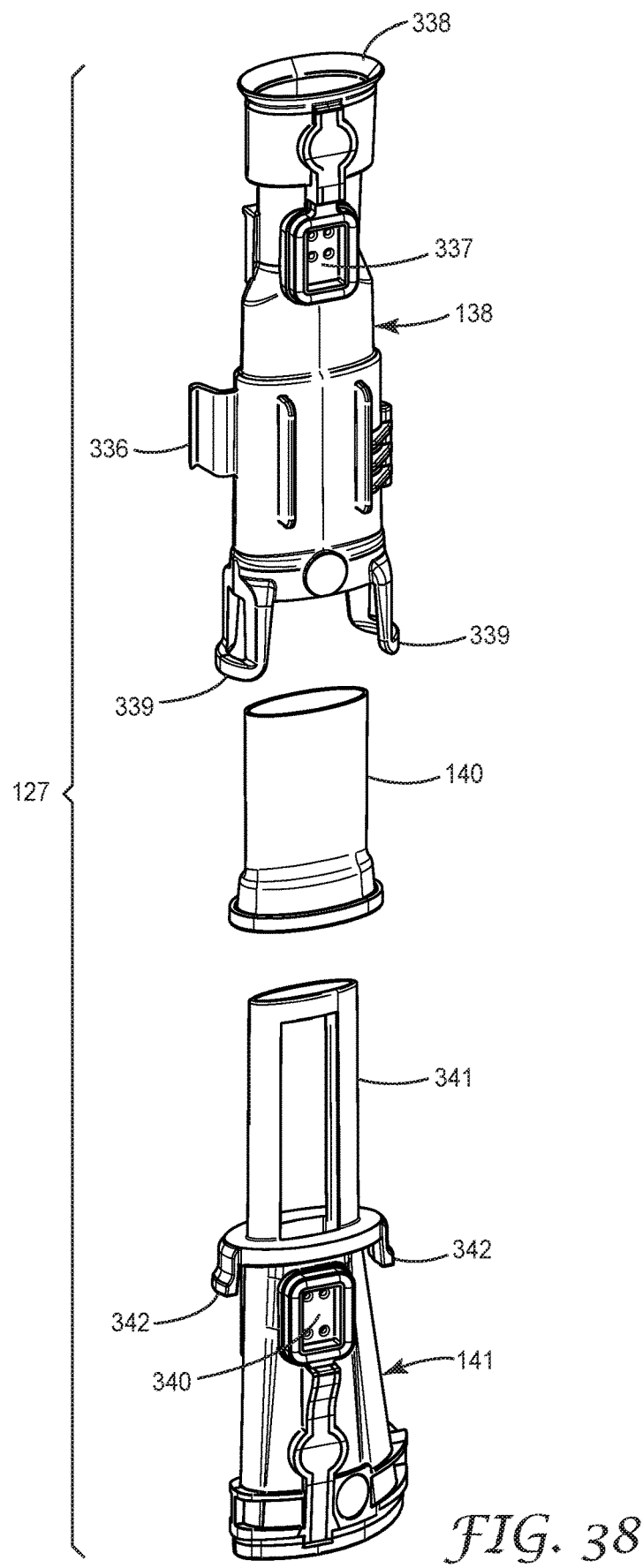
FIG. 38 is an isometric view of the air flowpath of the inhaler of FIG. 2.

The reusable assembly 109 includes a breath-actuated dose release firing system and a flow governor (such as a flow governor 140 of FIG. 3 and FIG. 38). If a patient were able to use the refill assembly 110 (e.g., as a 'press and breathe' inhaler) when not coupled to the reusable assembly 109, again an accurate does count would not be maintained, but additionally the patient would not benefit from the timed delivery resulting from the breath-actuated firing system and/or the medicament being delivered at a governed flow rate, as provided by the reusable assembly 109. Furthermore, as no usage data would be collected regarding time of dosing, inhalation profiles and the like, no usage data would be available for a healthcare professional to review to aid in the management of the patient's condition(s).

The components of the refill assembly 110 and reusable assembly 109 will now be described in greater detail.

Figure 10:
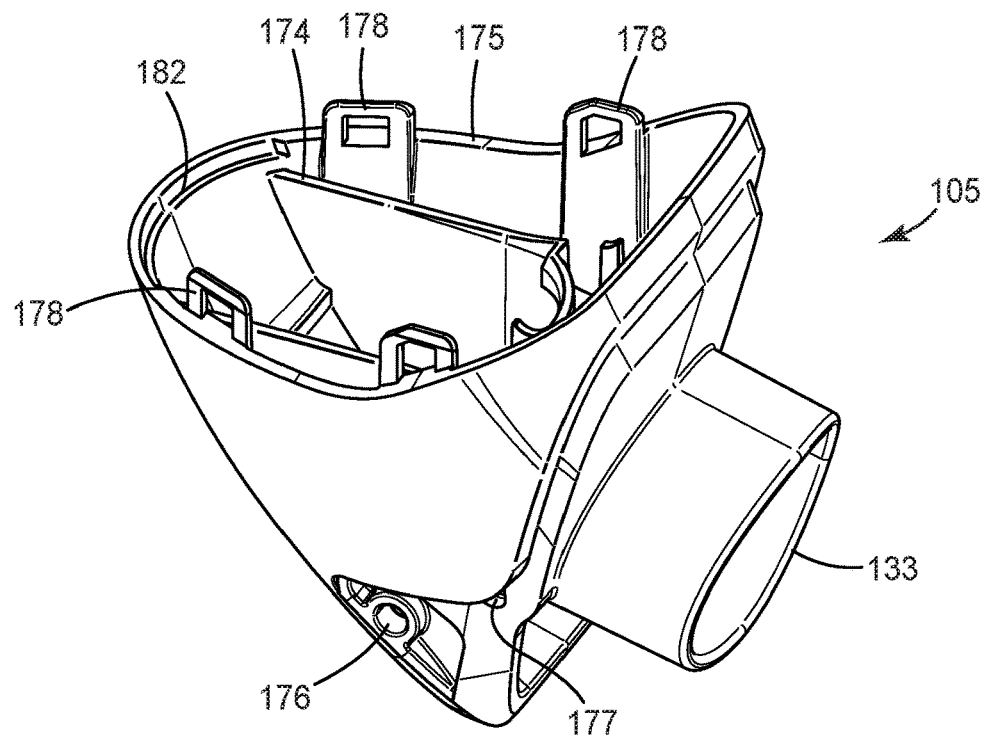
FIG. 10 is a front isometric view of the actuator assembly of the inhaler of FIG. 1.
Figure 11:
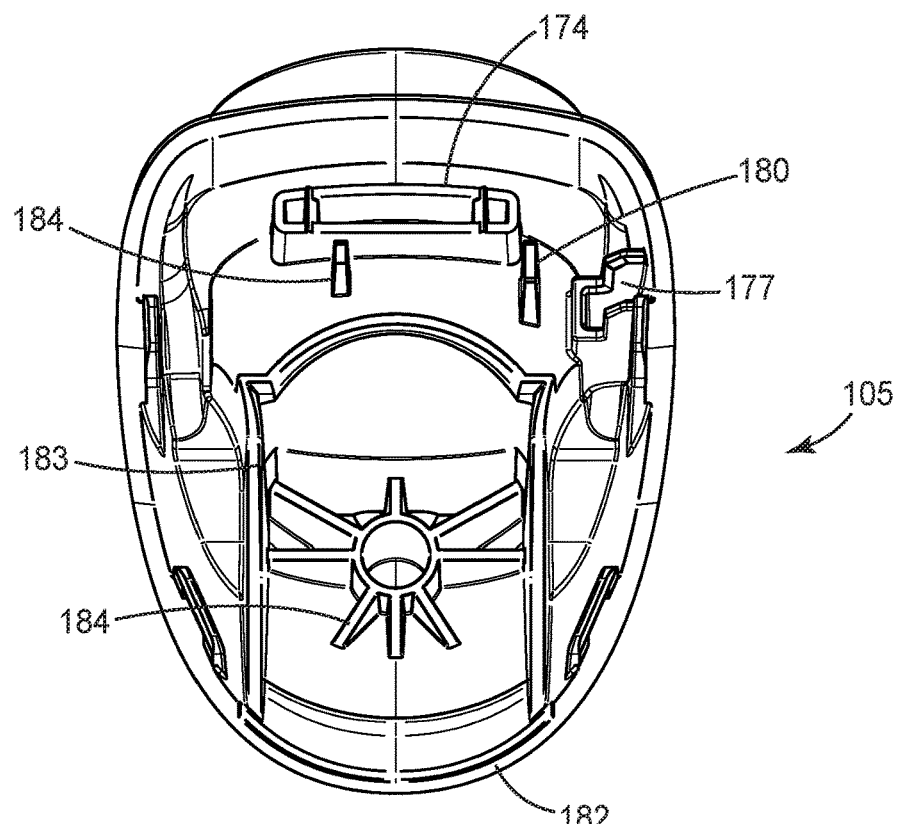
FIG. 11 is a plan view of the actuator assembly of FIG. 10.

The actuator assembly 105 is shown in greater detail in FIGS. 10 and 11. As shown in FIG. 10, the actuator assembly 105 includes an inner section or portion 174 and an outer section or portion 175, as well as the patient port 133. In some embodiments the actuator assembly 105 can be formed of one single piece, such that the patient port 133 is integrally formed with the inner section 174 and the outer section 175. Each side of the actuator assembly 105 includes an axle seat 176, such that the actuator assembly 105 includes a pair of opposing axle seats 176 (one on each side of the actuator assembly 105) Channel 177 exists between the inner section 174 and outer section 175 and is shaped to receive the patient port cover linkage 117 (see FIG. 15).

Figure 4:
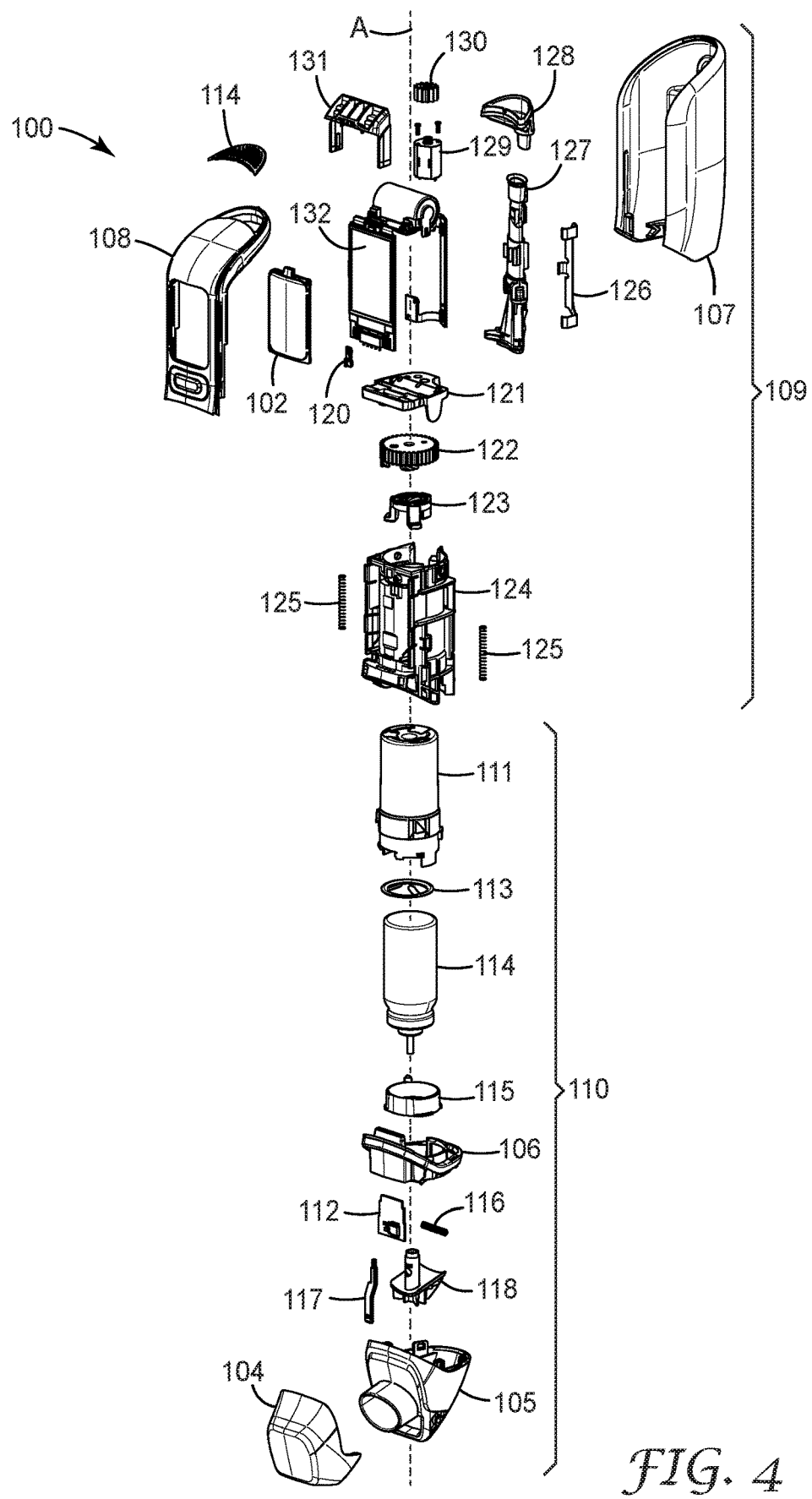
FIG. 4 is an exploded front isometric view of the inhaler of FIG. 1, with the reusable assembly and the refill assembly each shown disassembled.
Figure 4A:
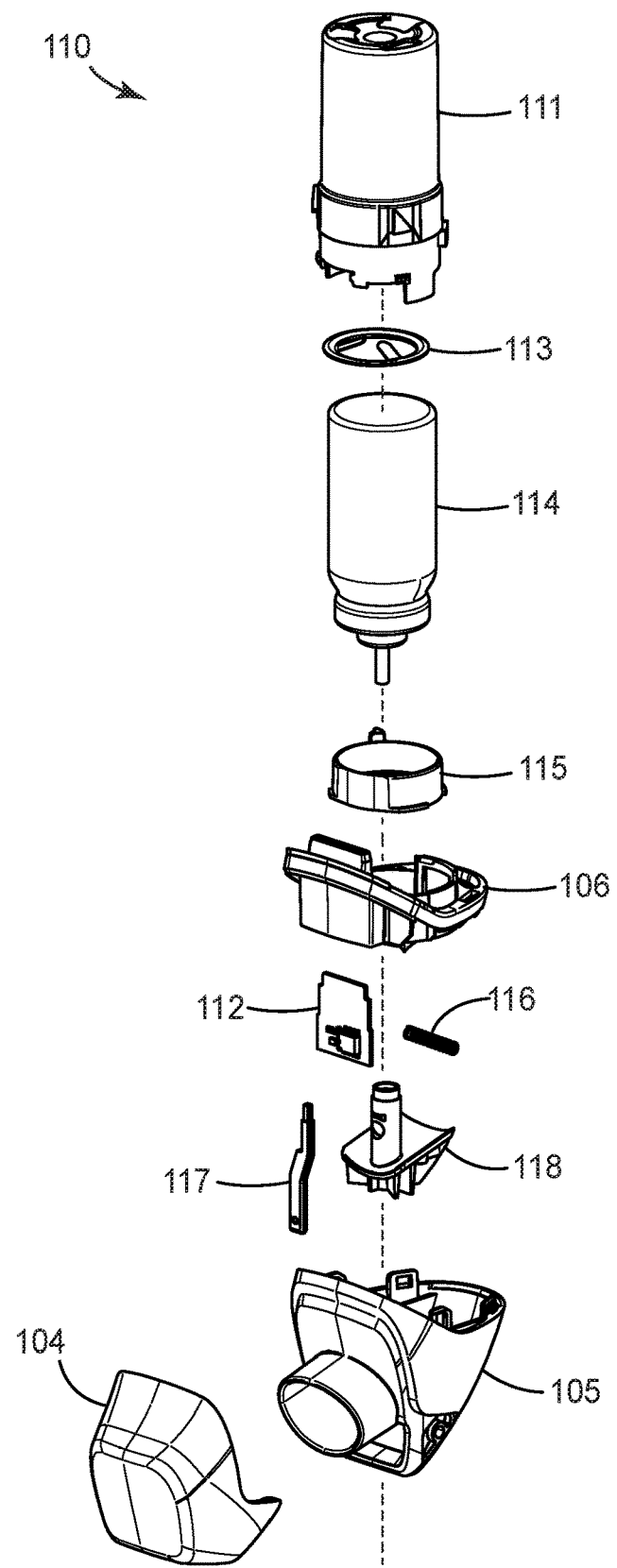
FIG. 4A is an exploded front isometric view of the refill assembly of the inhaler of FIG. 1, shown disassembled.
Figure 4B:
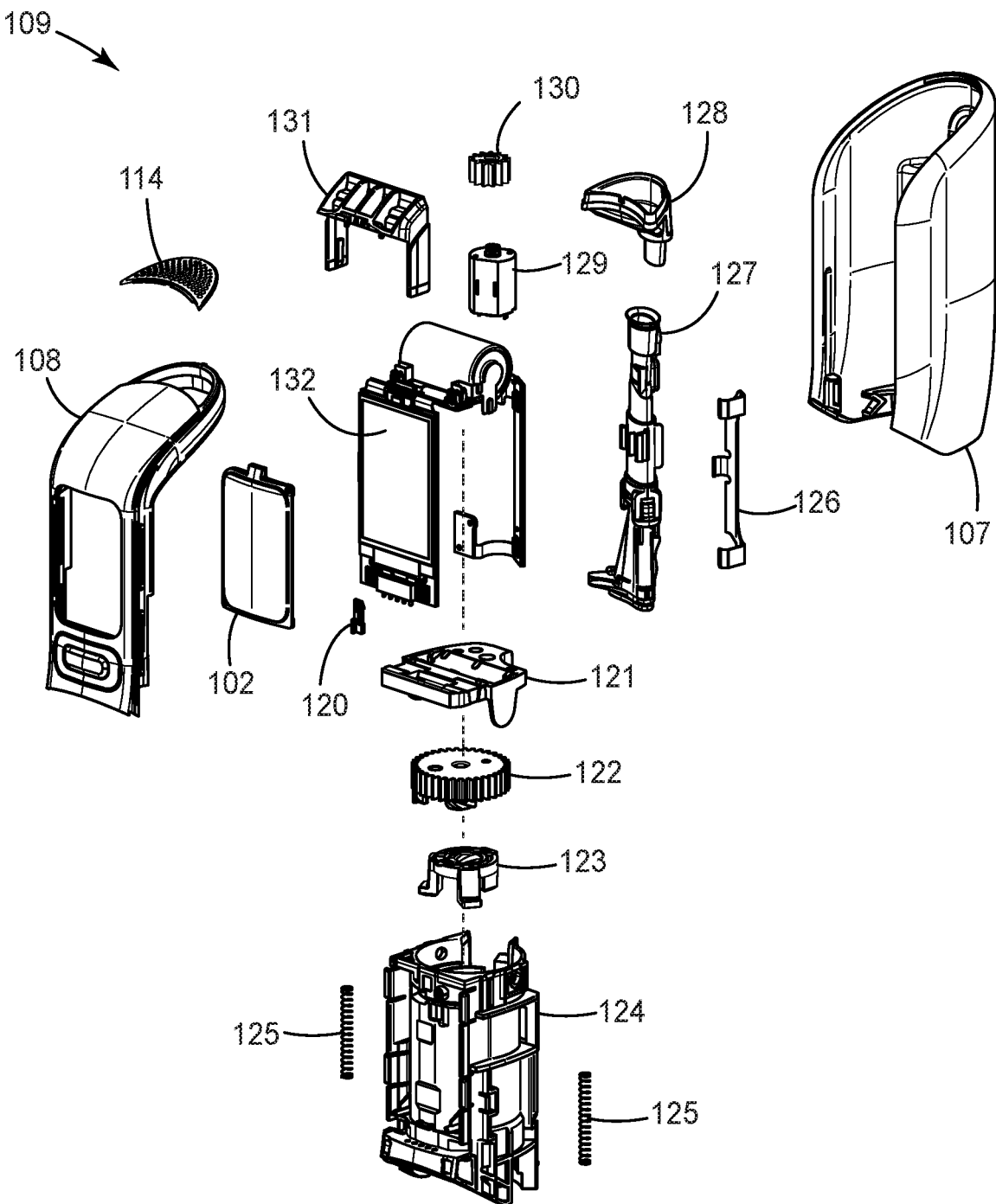
FIG. 4B is an exploded front isometric view of the reusable assembly of the inhaler of FIG. 1, shown disassembled.
Figure 16:
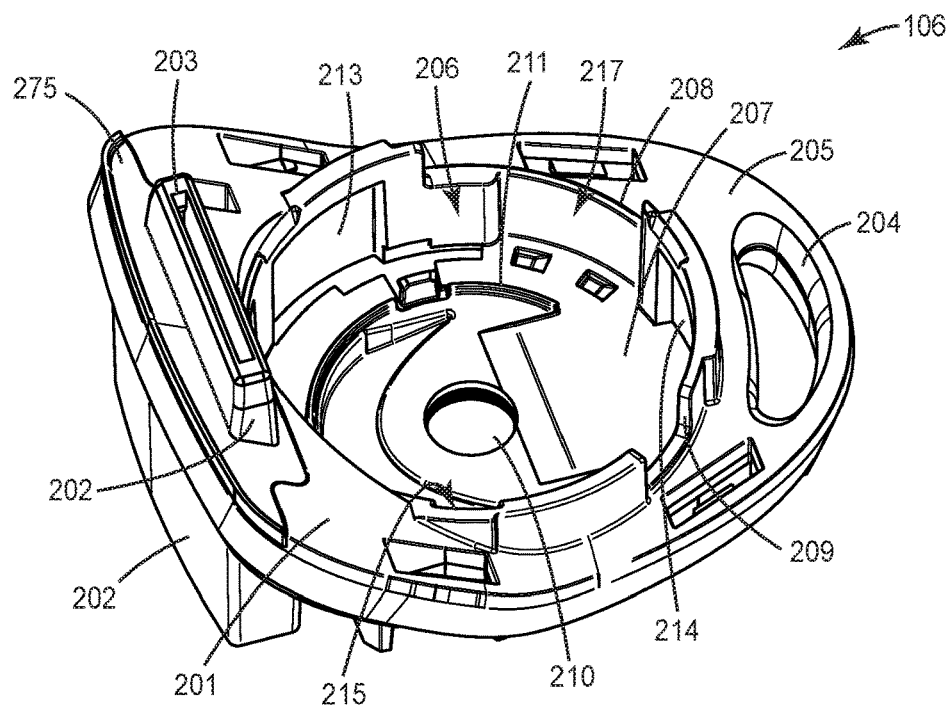
FIG. 16 is a side isometric view of the air sealing cap of the refill assembly of FIG. 2.
Figure 17:
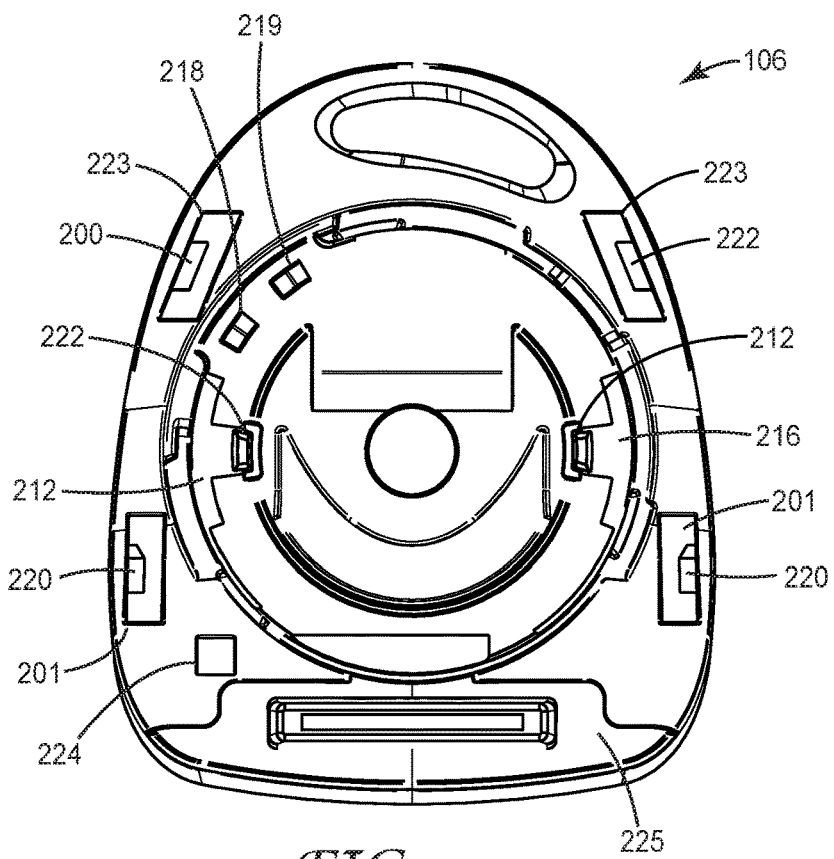
FIG. 17 is a top plan view of the air sealing cap of FIG. 16.
Figure 18:
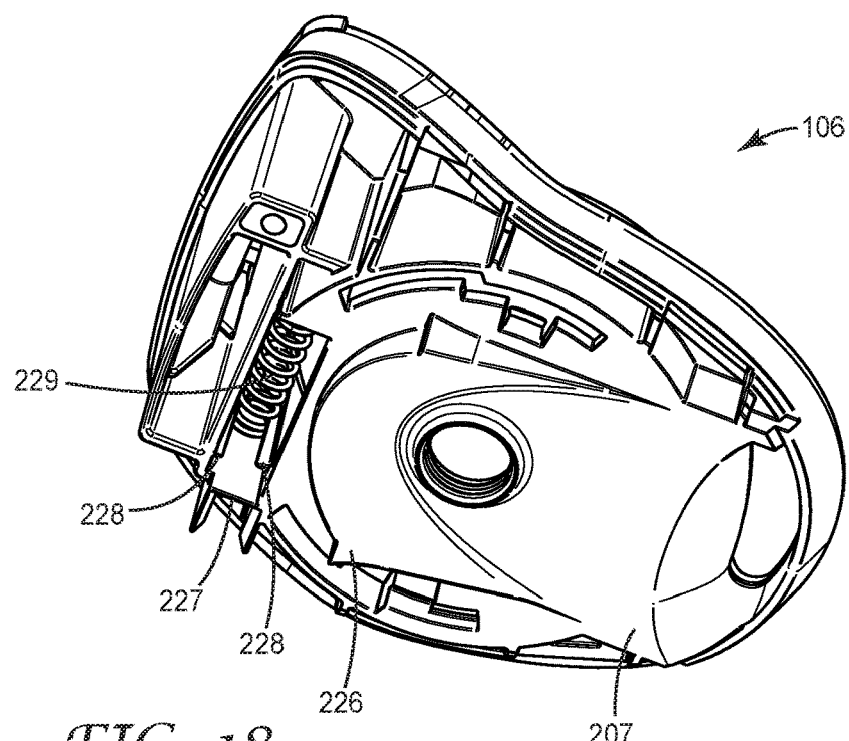
FIG. 18 is a lower isometric view of the air sealing cap FIG. 16.

The actuator assembly 105 further comprises four clips 178 that project above the outer section 175 and which are positioned and sized such that they can interact with the air sealing cap 106 (see FIGS. 16 to 18). As shown in FIG. 11, located on the outer surface of the inner section 174 is a memory device receiver 179 which provides partial housing and support of memory device 112. Additionally, column 180 and column 181 are located proximate the receiver 179. The function of column 180 and column 181 is to provide support for the air sealing cap 106 when it is connected to the actuator assembly 105. At the rear of the actuator assembly 105, on the inner surface of the outer housing 175, is a curved ledge 182 that provides support and location for the air sealing cap 106. A stem post assembly recess 183 is located inside the inner section 175, defining a receiving/locating area for the stem post assembly 118 (FIG. 4). The stem post assembly recess 183 further comprises ribs 184 which provide rigidity for the actuator assembly 105 and provide support, alignment and rigidity for the stem post assembly 118.

Figure 12:
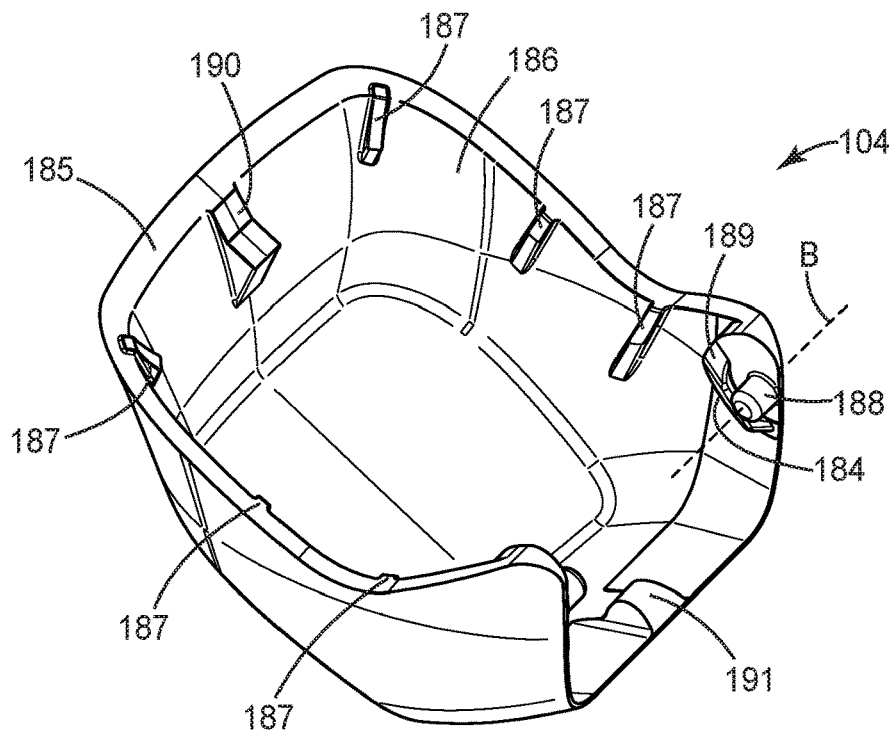
FIG. 12 is an isometric view of the patient port cover of the refill assembly of FIG. 2.

Referring to FIG. 12, the patient port cover 104 has a mating surface 185 shaped and sized to fit closely against the opposing surface of the actuator assembly 105 to form a flush fit to prevent ingress of debris when the inhaler 100 is not in use. On the inner surface 186 of the patient port cover 104 exist ribs 187 (three on each side, such that the patient port cover includes six ribs). Additionally, located on the inner surface 186 are axles 188 and guides 189 (one on each side, such that patient port cover 104 includes two axles 188 and two guides 189). The axles extend along and define the pivot axis B. The patient port cover 104 can be dimensioned to receive (i.e., to cover) the patient port, and to house or enclose at least a portion of the contour of the front of the outer section of the actuator assembly 105, i.e., when in its closed position (FIGS. 1 to 3). The six ribs 187, in addition to a larger central rib 190, provide rigidity to the patient port cover and additionally are shaped and sized such that they aid with engagement between the patient port cover 104 and the actuator assembly 105. Furthermore, the patient port cover 104 contains a curved detent 191 which provides a degree of resistance when the patient port cover 104 is closed, thus ensuring that the patient port cover 104 remains in place when it is closed.

Figure 13:
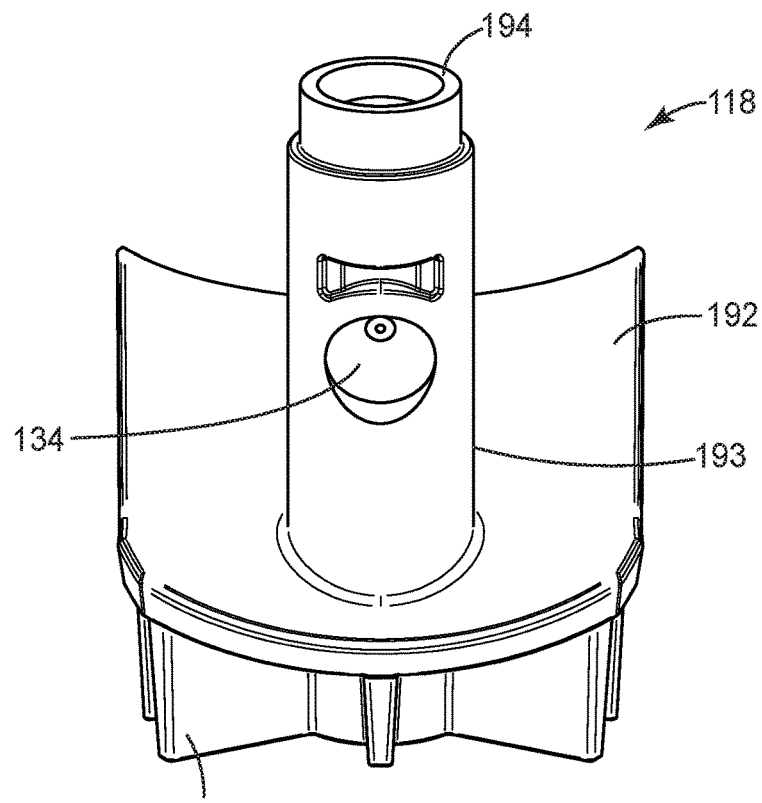
FIG. 13 is a front isometric view of the stem post assembly of the refill assembly of FIG. 2.
Figure 14:
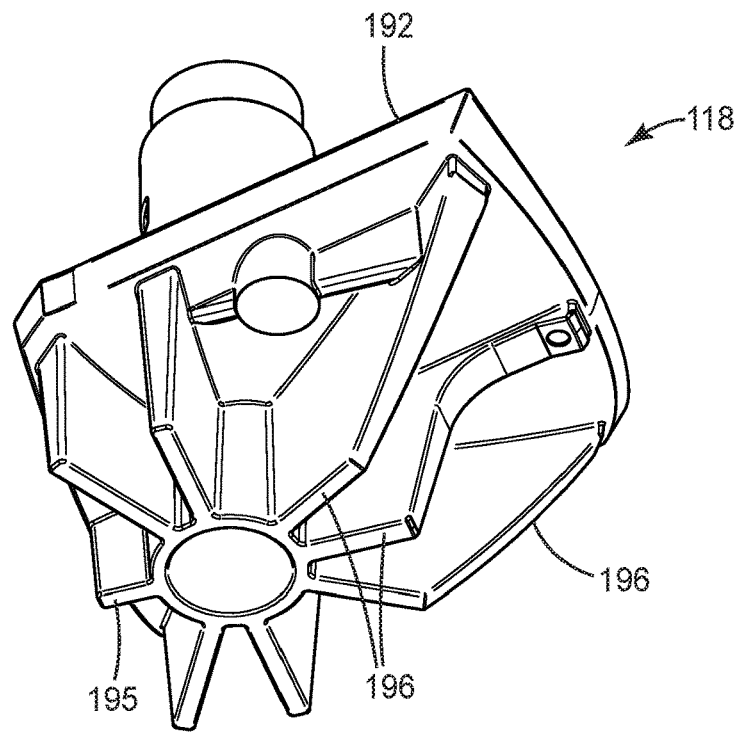
FIG. 14 is a front isometric view of the stem post assembly of the refill assembly of FIG. 2.

The stem post assembly 118 is shown in greater detail in FIGS. 13 and 14. The stem post assembly 118 has a base 192 which is both convex and sloped. Towards the front of the base 192, positioned centrally with respect to the convex curvature, is the stem post housing 193 that further comprises the spray orifice 134 and the stem socket 194.

Additionally, as shown in FIGS. 13 and 14, beneath the base 192 are ribs 195 that are shaped and sized so that they engage with the ribs 184 of the actuator assembly 105. In addition, three of the rear ribs 196 have angled surfaces which are contoured to align with the actuator assembly 105 when the stem post assembly 118 is located in the stem assembly recess 183 of the actuator assembly 105.

Figure 15:
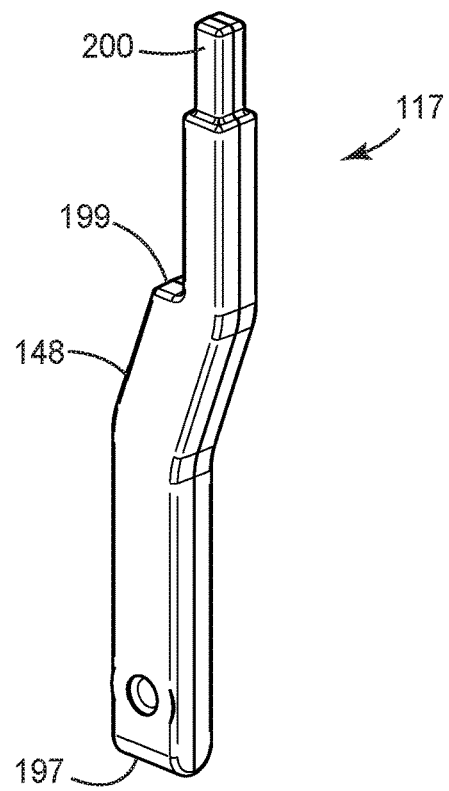
FIG. 15 is a front isometric view of the patient port cover linkage of the refill assembly of FIG. 2.

FIG. 15 shows the patient port cover linkage 117 having a curved, lower end 197, a kinked section 198, a ledge 199 and a top pin end 200. Because of the kinked section 198, the top pin end 200 and the curve lower end 197 are not axially aligned.

The air sealing cap 106 is shown in greater detail in FIGS. 16 and 17. At the front of the air sealing cap 106 is a curved banked surface or section 201 in the middle of which a memory device housing 202 is located. The memory device housing 202 protrudes above and below the curved banked section 201 and envelopes the memory device 112. However, access to the memory device 112 is made possible through the aperture 203. Towards the back of the air sealing cap 106 is a refill air flow path inlet 204. As shown, the air sealing cap 106 can further include a flat surface 205 that connects the refill air flow path 204 with the banked surface 201. A wall 206 connects the flat surface 205 with a base 207. Some sections of the wall 206 are essentially flush with the flat surface 205, but other sections are raised to leave slot 208 and slot 209. The base 207 comprises several further features. Centrally located is a stem post housing receiver 210, a rail 211, two clips 212, an aperture to receive a wedge 213, an aperture to receive a wedge 214 and an aperture to receive a wedge 215 (not visible in FIGS. 16 and 17).

Furthermore, two "T" shaped apertures 216 exist between the base 207 and the wall 206 on opposite sides of the air sealing cap 106. The wall 206 comprises a thinner wall section forming a further recess 217. Partially disposed within the recess 217, located on the base 207, are yet further apertures to receive wedges 218 and 219. The air sealing cap 106 further comprises four clips: two front clips 220 visible through front apertures 221 that exist in the curved banked surface 201, and two rear clips 222 visible through rear apertures 223. The air sealing cap further comprises a hole 224 that is located in the curved banked surface 201 of the air sealing cap 106. The hole 224 receives the top pin end 200 of the patient port cover linkage 117 (FIG. 15).

The air sealing cap 106 can be made of any material with sufficient rigidity; preferably the material used is a plastic. However, in some embodiments, surfaces and/or regions thereof can be covered with a secondary material. By way of example, section 225 can be over-molded with TPE to provide a degree of dimensional tolerance take up when the refill assembly 110 is coupled to the reusable assembly 109.

FIG. 18 shows that the underside of the base 207 of the air sealing cap 106 has a profiled section 226 that projects and is shaped and sized as to mate with the actuator assembly 105. Furthermore, it can be seen that the air sealing cap 106 comprises a housing 227. Contained within the housing 227 at one end are retaining ribs 228 and a biasing element 229. The retaining ribs 228 engage with part of the biasing element 229 to retain the element 229 within the housing.

The sleeve 111 is shown in greater detail in FIGS. 19 to 22. The term "sleeve" is considered herein to mean any component that extends over a substantially part of the canister such that it protects the canister and covers at least a portion of the top of the canister to prevent direct contact by the user. The sleeve of the present invention need not extend around the full circumference of the canister. The sleeve 111 of the present example is essentially cylindrical with a top portion 230 that has three circumferentially symmetrical apertures 231. Approximately three quarters of the way along the cylindrical body 232 of the sleeve 111 is a ring 233, upon which are formed three teeth 234, 235 and 236. Just beneath the ring are two lower teeth, 237 and 238. Tooth 237 further comprises upper sloped edge 237a and lower sloped edge 237b. Likewise tooth 238 further comprises upper sloped edge 238a and lower sloped edge 238b.

At the base 239 of the sleeve 111, spaced at equal circumferential distance, are a wedges 240, 241 and 242. Furthermore, at the base 239 of the sleeve 111 is a recess 243, to one side of which is a boss 244. Extending from the base 239 of the sleeve 111 are two legs 245. The sleeve 111 includes an inner chamber 246, dimensioned to receive, at least a portion of the canister 114.

Importantly, the apertures 231 are not sufficiently large to readily accommodate an adult patient's finger(s), thus preventing the patient from applying force to the canister 114 to release a dose of medicament.

The sleeve 111 is formed of a material that is substantially opaque, such that when the canister 114 is positioned in the inner chamber 246, the canister 114 is only visible to the patient through the apertures 231. However, it should be understood that the sleeve 111 can instead be constructed using a transparent material so that the patient is able to see any labelling on the canister 114. Alternatively, in some embodiments, the sleeve 111 can include a transparent portion (e.g., a window) through which the patient can view any labelling on the canister 114 (at least when the refill assembly 110 is not coupled to the reusable assembly 109). In further embodiments, labelling can be provided on the outer cylindrical body 232 of the sleeve 111.

Figure 23:
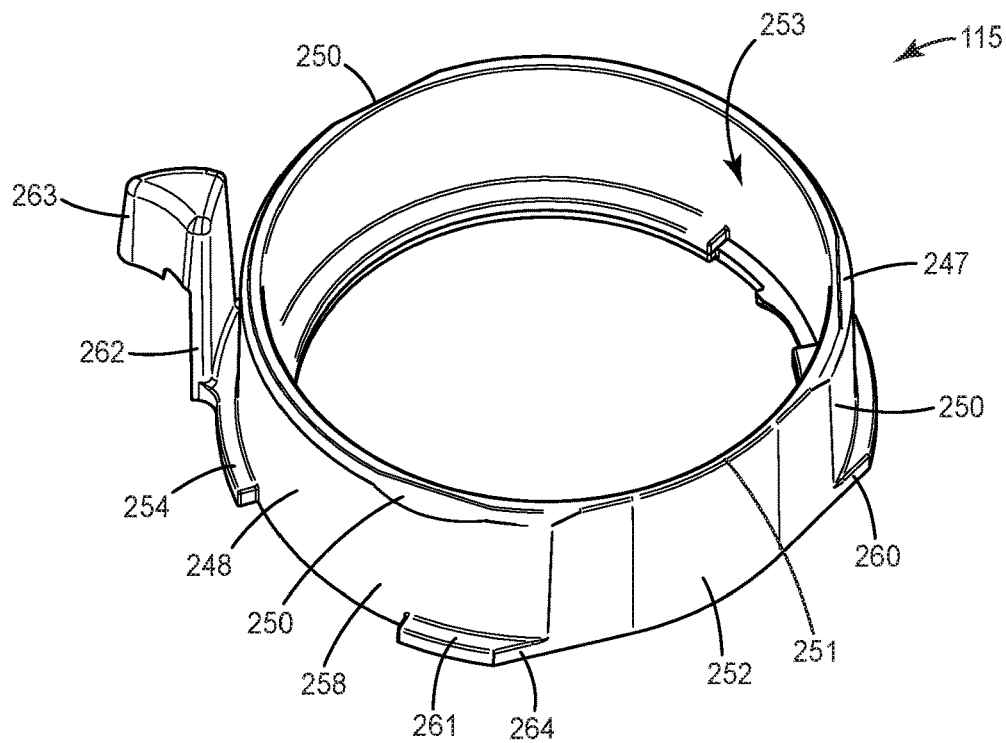
FIG. 23 is a upper side isometric view of the override element of the refill assembly of FIG. 2.
Figure 24:
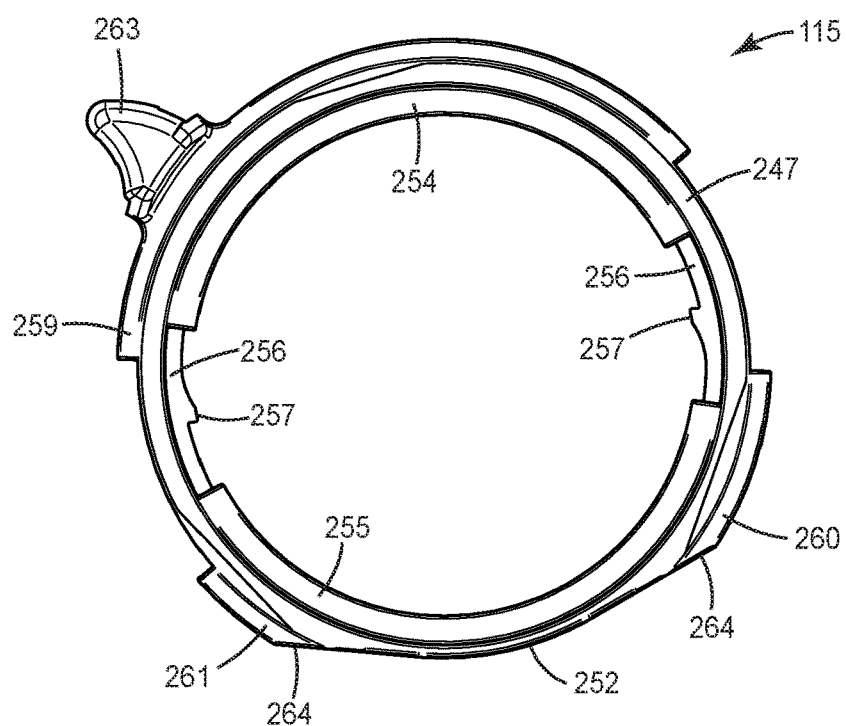
FIG. 24 is a top plan view of the of the override element of FIG. 23.
Figure 25:
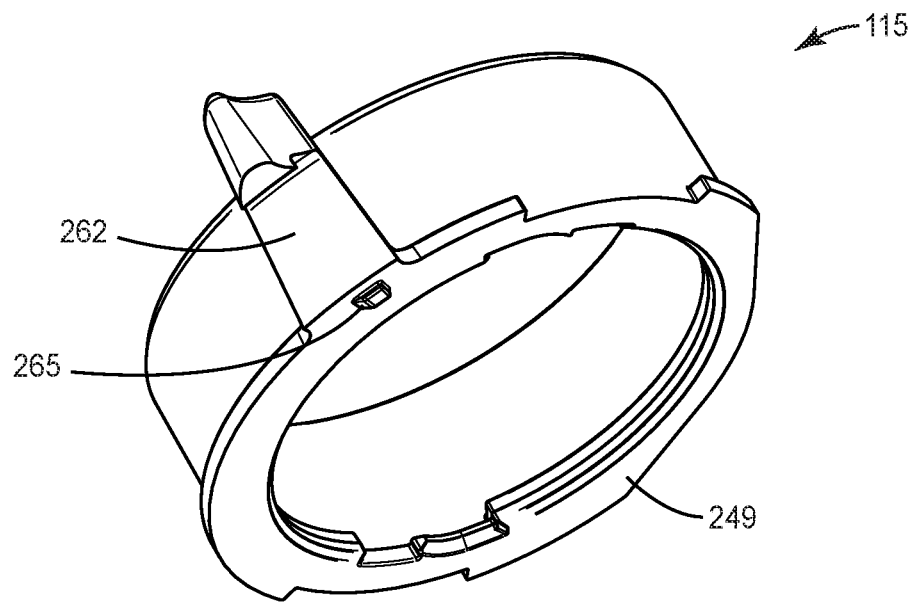
FIG. 25 is a lower isometric view of the override element of FIG. 23.

The refill assembly 110 includes an override element 115, as shown in FIGS. 23 to 25. The override element 115 is generally annular in shape and is dimensioned to be received, at least in part, by the sleeve 111. The override has a top section 247, a body section 248 and a bottom section 249. The top section 247 has three chamfers 250 equally spaced about it. Additionally it can be seen that the body section 248 further comprises a thin wall section 251 which is thinner and has a generally flatter body section 252 than the rest of the body section 248. At the bottom of the inner surface 253 of the body section 248 are a rear inner ledge 254 and a front inner ledge 255 that follow the shape of the body section 248. The rear inner ledge 254 and the front inner ledge 255 are connected together via two side inner ledges 256. Located approximately in the middle of each of the two inner side ledges is a ratchet 257. At the bottom of the outer surface 258 of the body section 248 are three outer ledges, a rear outer ledge 259, a long front outer ledge 260, and a short front outer ledge 261, that extend radially outwardly. The rear outer ledge 259 follows the contour of the body section 248 however it is not aligned with the rear inner ledge 254. Projecting up from the rear outer ledge 259, parallel to the body section 248, is a post 262, and sitting on top of the post 262 is a boss 263. The long front outer ledge 260 has a tapered edge 264 so that the ledge 260 tapers into the flatter body section 252. The long front outer ledge 260 is misaligned with the front inner ledge 255. The short front outer ledge 261 also comprises a tapered edge 264, and furthermore the short front outer ledge 261 is also misaligned with the front inner ledge 255. The bottom 249 of the override element 115 is essentially flat with the exception of a protruding wedge 265 that is positioned just off-center from the post 262.

Figure 26:
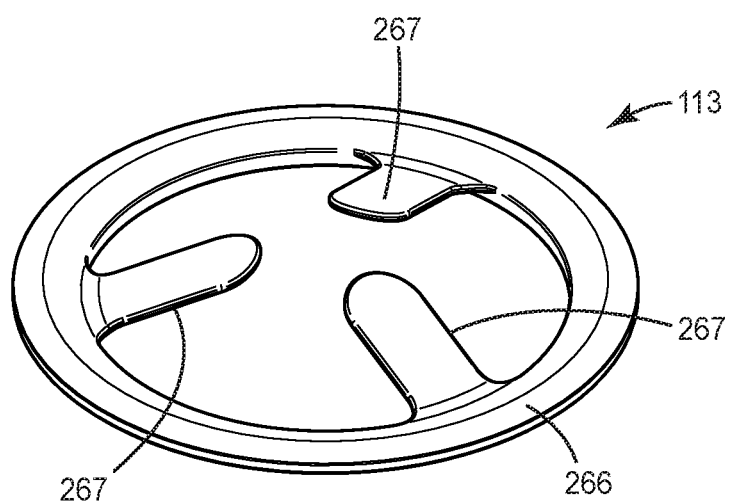
FIG. 26 is an upper side isometric view of a biasing element of the refill assembly of FIG. 2.

The biasing element 113 is shown in FIG. 26. It is essentially annular, having a ring 266 from which three arms 267 project inwardly, angled above the plane of the ring 266. The biasing element 113 sits on the base of the canister 114 with the arms 267 in contact with the inner top surface of the sleeve 111. It is conceivable within the scope of the invention that an additional spacer is positioned between the canister 114 and the biasing element 113 (e.g., if a smaller canister were to be used). The arms 267 of the biasing element 113 serve to partially secure it to the sleeve 111 in order to avoid unwanted sounds (e.g., rattles) being generated by unwanted relative movement between the biasing element 113 and the sleeve 111.

Assembly of the refill assembly 109 and the interaction of each part will now be described with reference to FIGS. 10 to 26. The axles 188 of the patient port cover 104 (See FIG. 12) are dimensioned to be received in the axle seats 176 of the actuator assembly 105 (FIG. 10). The patient port cover linkage 117 is received by the patient port cover linkage housing 177 of the actuator assembly 105 (FIGS. 10 and 11). The stem post assembly 118 (FIG. 13) is received in the stem post assembly recess 183 of the actuator assembly 105 (FIG. 11) so that it forms a flush fit. The memory device 112 is inserted into the memory device receiver 179 of the actuator assembly 105 (FIG. 11). The override element 115 is received by the air sealing cap 106, positioned such that the wedge 265 of the override element 115 (FIG. 25) is located in the wedge slot 218 of the air sealing cap 106 and the clips 212 of the air sealing cap 106 clip over the side inner ledges 256 of the override element 115. Additionally, the three chamfers 250 of the override element 115 are aligned (i.e., facing) the three wedge receivers 213, 214 and 215 of the air sealing cap 106. The post 262 of the override element 115 is located in the recess 217 of the air sealing cap 115, with the boss 263 of the override element 115 residing in slot 208 of the air sealing cap 115.

The biasing element 113 is placed on the base of the canister 114, orientated so that the arms 267 of the biasing element 113 project away from the base of the canister 114. The canister 114 and the biasing element 113 are received by the inner chamber 246 of the sleeve 111. The air sealing cap 106, with the override element 115 connected, receives the sleeve 111, containing the canister 114 and the biasing element. The body section 248 of the override element 115 is received by the inner chamber 246 of the sleeve 111. Importantly, wedges 240, 241 and 242 of the sleeve 111 are positioned in alignment with the chamfers 250 of the override and wedge receivers 213, 214 and 215 of the air sealing cap 115 respectively. The chamfers 250 allow the sleeve 111 to flex somewhat so that wedge 240, wedge 241 and wedge 242 can clip into wedge receiver 213, wedge receiver 214 and wedge receiver 215 respectively of the air sealing cap 106. Once clipped in place, the sleeve 111 cannot be removed from the air sealing cap 106, at least not without the use of destructive force; hence the canister 114 cannot be removed.

Figure 19:
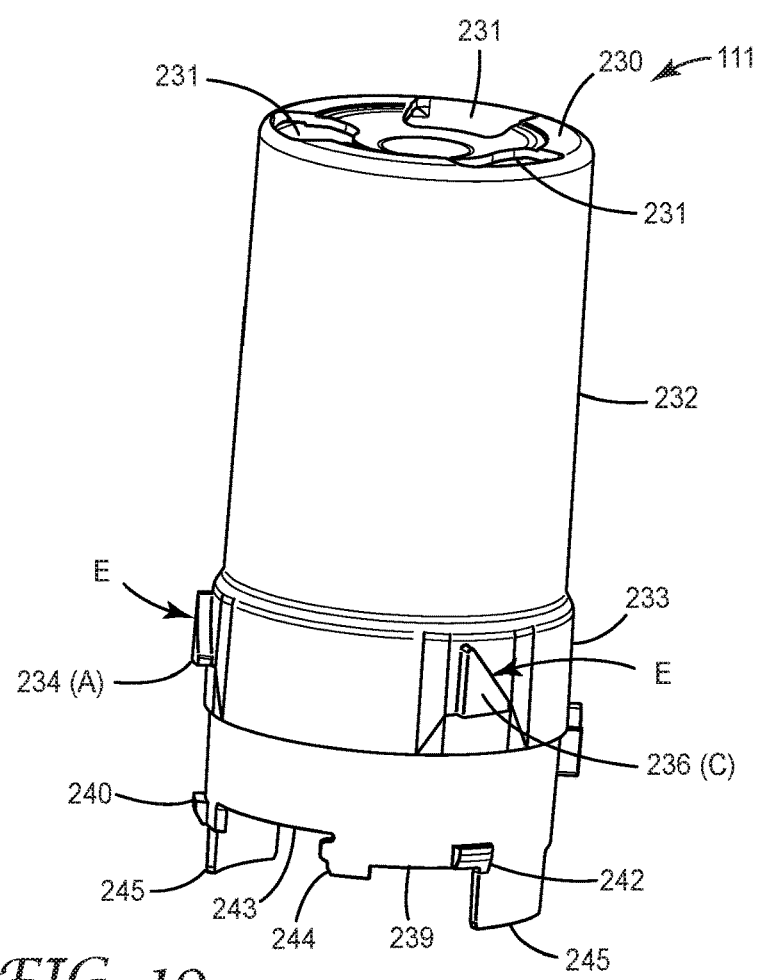
FIG. 19 is a upper side isometric view of the sleeve of the refill assembly of FIG. 2.
Figure 20:
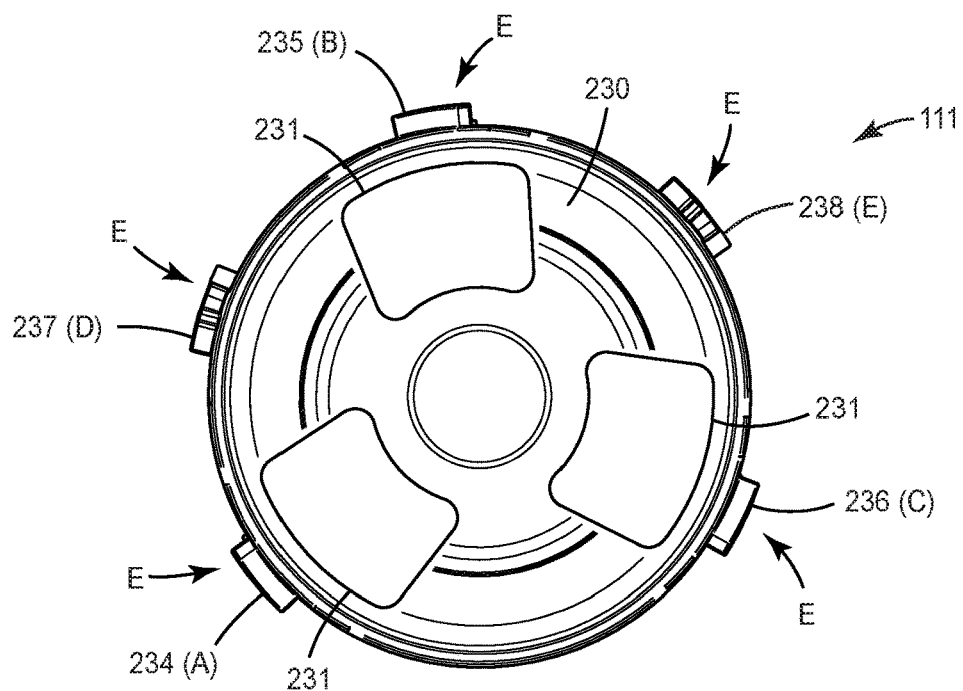
FIG. 20 is a top plan view of the sleeve of FIG. 19.
Figure 21:
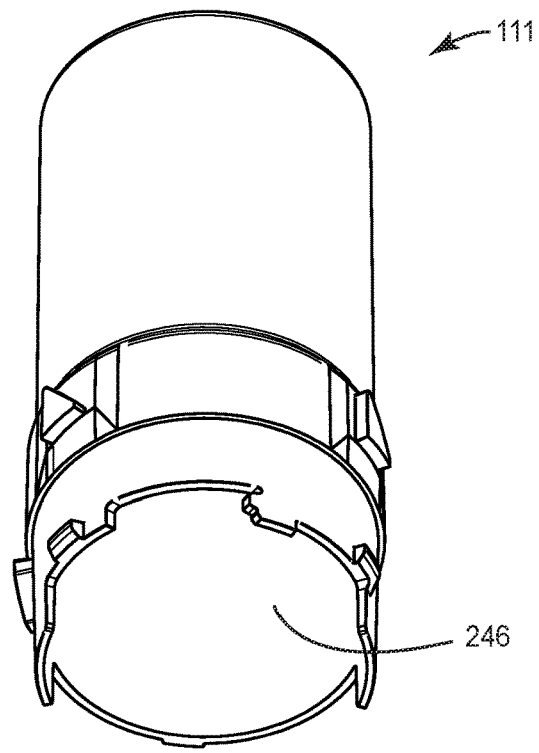
FIG. 21 is a lower isometric view of the sleeve of FIG. 19.
Figure 22:
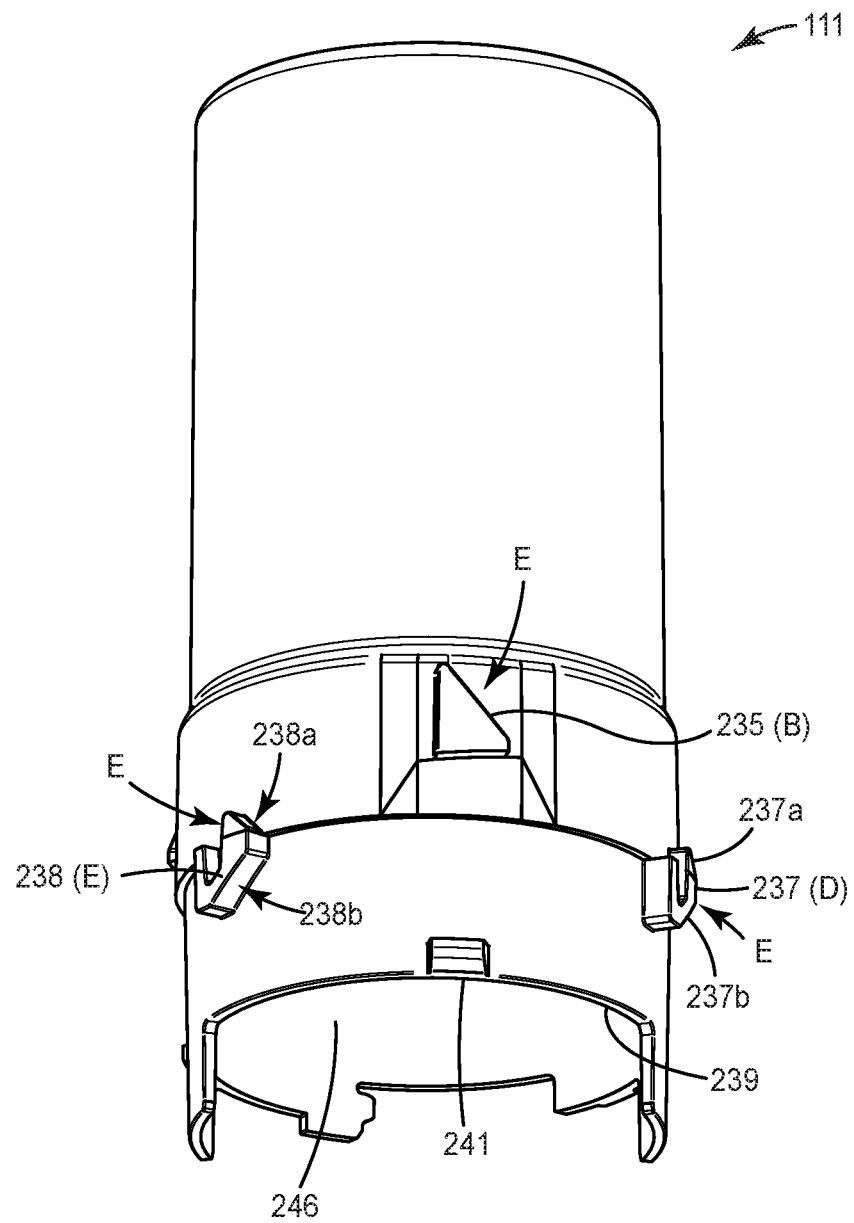
FIG. 22 is a lower side isometric view of the sleeve of FIG. 19.

The biasing element 229 is inserted into the housing 227 of the air sealing cap 106 by sliding a section (i.e., a coil) of the biasing element 229 over the ribs 228 of the housing 227 (as shown in FIG. 18). The other end of the biasing element 229 is pressed against the boss 244, and is partially located in the recess 243 of the sleeve 111 (FIG. 19). The legs 245 of the sleeve 111 are positioned above the "T" shaped apertures 216 of the air sealing cap 106; however positioned between them are portions of the rear outer ledge 259 and front long outer ledge 260 of the override element 115. The air sealing cap 106 is received by the actuator assembly 105. The clips 178 of the actuator assembly 105 are received through the front apertures 201 and the rear apertures 203 of the air sealing cap 106 and engage with the front clips 200 and the rear clips 202 of the air sealing cap 106, thereby securing the two parts together. Additionally, the stem post housing 193 engages with the stem post receiver 210 of the air sealing cap 106, and the stem 137 of the canister 114 is located in the stem socket 194 of the stem post assembly 118. Furthermore, the patient port cover linkage 117 is received by the hole 224 of the air sealing cap 106. The memory device 112 is received by the memory device housing 202 of the air sealing cap 106, and a portion of the memory device protrudes through the aperture 203 of the memory device housing 202.

Attaching the air sealing cap 106 to the actuator assembly 105 leads to the formation of the refill air flow path 135 such that when a patient inhales through the patient port 113, entry of air is caused to flow only through the refill air flow path inlet 204 of the air sealing cap 106.

The refill assembly 110 is configured such that after the refill assembly is assembled (FIG. 2) it cannot be dissembled, at least not without the use of destructive force and damage to at least a portion of the refill assembly 110. As a result, the canister 114 and the memory device 112 remain with one another in the refill assembly 110.

Figure 27A:
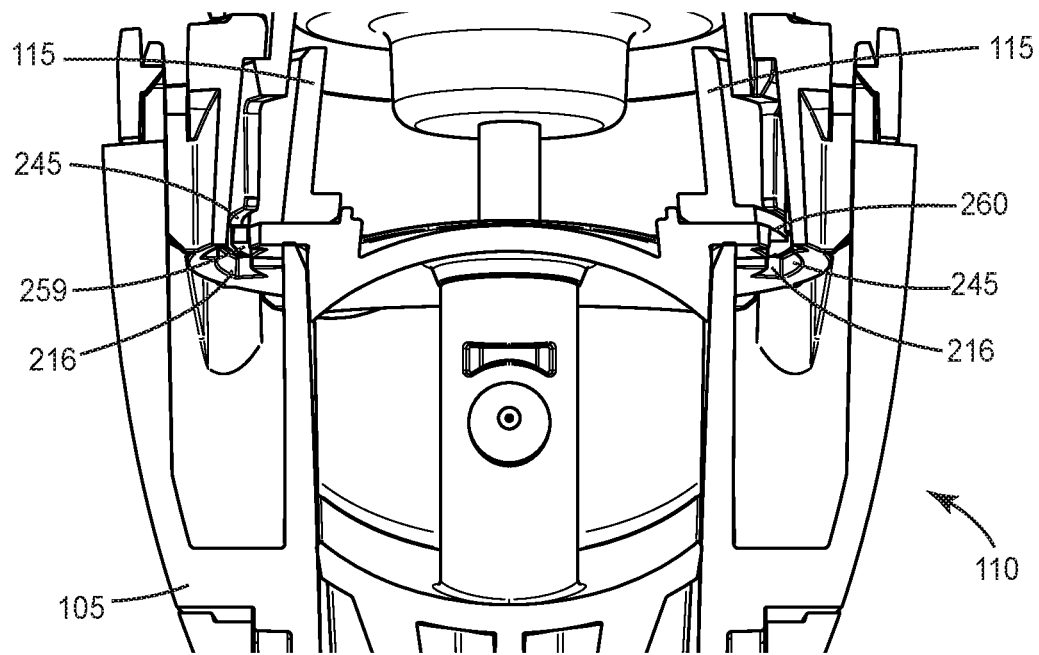
FIG. 27A is a front cross-sectional part view of the inhaler of FIG. 1 taken along line XXVII-XXVII in FIG. 2B showing the relationship between the sleeve, the override element and the chassis.
Figure 27B:
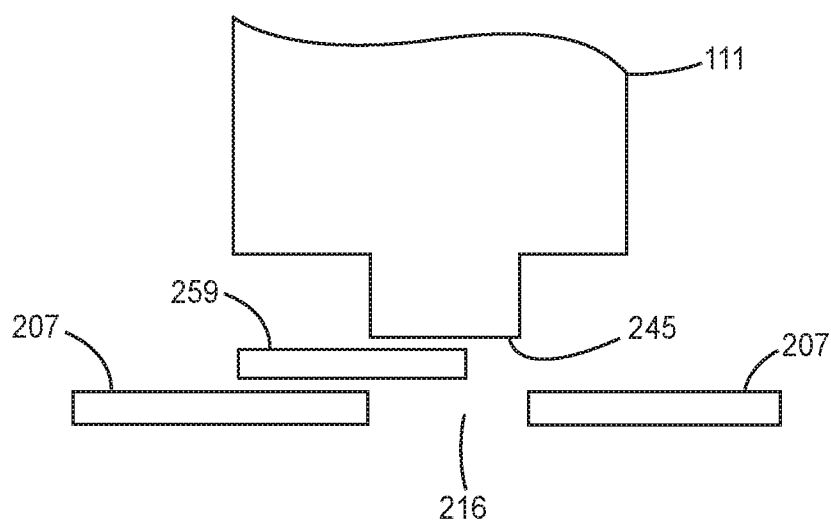
FIGS. 27B to 27E are schematic representations of the inter-relationship between the sleeve, the override element and the chassis shown in FIG. 27A.

Furthermore, the sleeve 111 prevents access to the canister 114, and the sleeve 111 is not capable of axial travel because the legs 245 of the sleeve 111 are prevented from travelling through the "T" shaped apertures 216 of the air sealing cap 106 due to obstruction caused by portions of the rear outer ledge 259 and the front long outer ledge 260 of the override element 115 (see FIGS. 27A and 27B). A dose of medicament thus cannot be released by the patient applying force to the base of the sleeve 111. The only movement that the sleeve is permitted to make is one of rotation. The wedge receiver 213, wedge receiver 214 and wedge receiver 215 of the air sealing cap 115 are somewhat wider than wedge 240, wedge 241 and wedge 242, thus allowing a defined amount of rotation.

In order to obtain a dose, the patient must connect the refill 110 to the reusable 109. Before describing this, the components of the reusable assembly will now be described in further detail.

Figure 28:
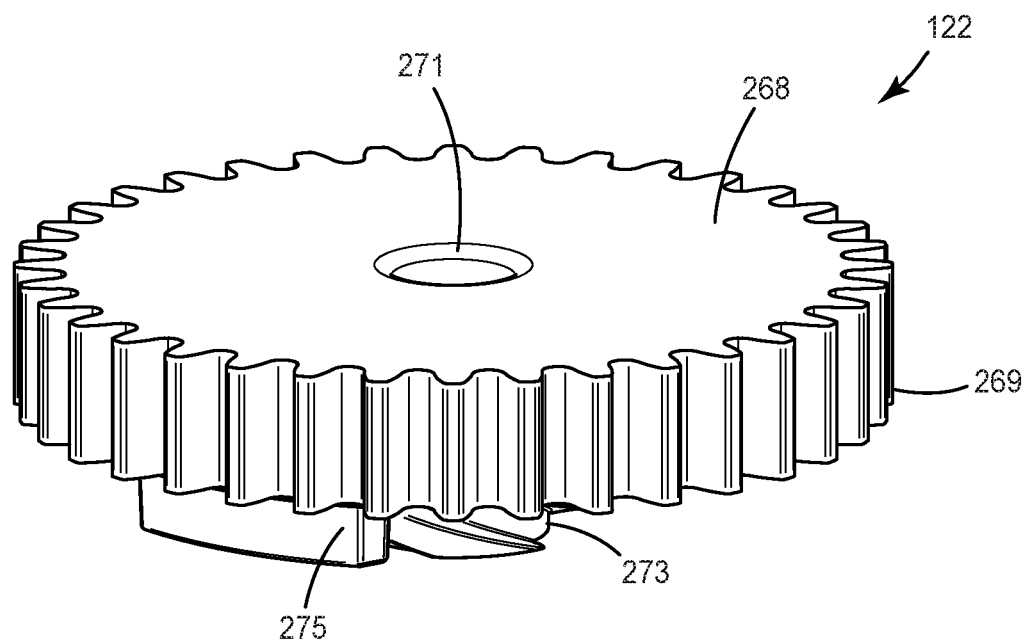
FIG. 28 is an upper side isometric view of the lead screw of the reusable assembly of FIG. 2.
Figure 29:
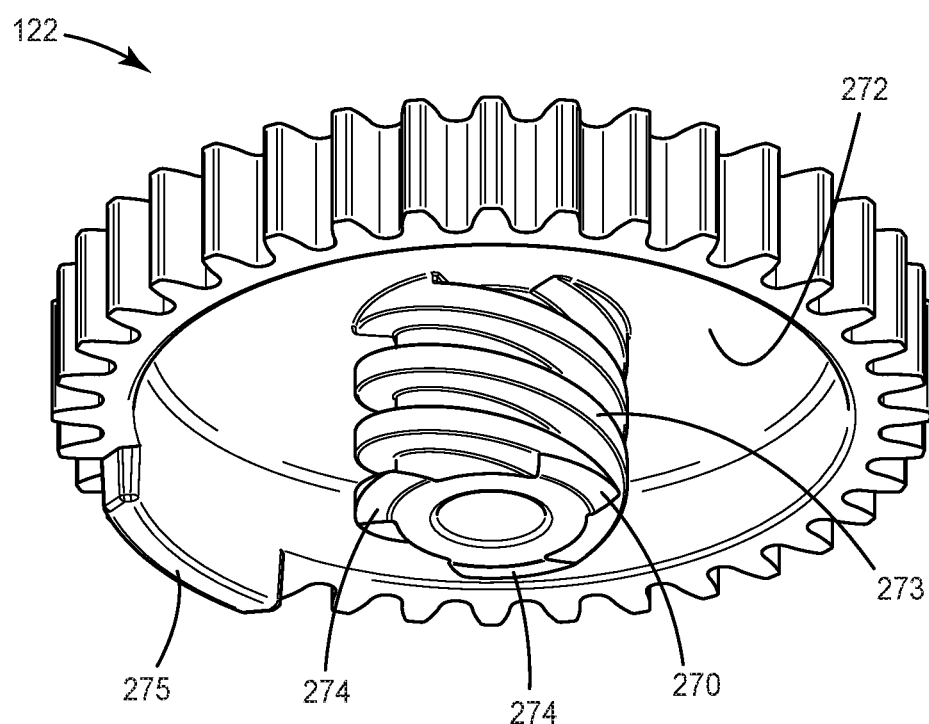
FIG. 29 is a lower side isometric view of the lead screw of the FIG. 28.

The lead screw 122, of the reusable assembly 109 is shown in FIGS. 28 and 29. The lead screw 122 comprises a top surface 268, a toothed body section 269 and a base section 270. Positioned centrally in the top surface is a socket 271. The lead screw 122 further comprises an inner chamber 272 that contains a worm gear 273 with three helical threads 274. Extending form the base section 270 of the lead screw is a latch 275.

Figure 30:
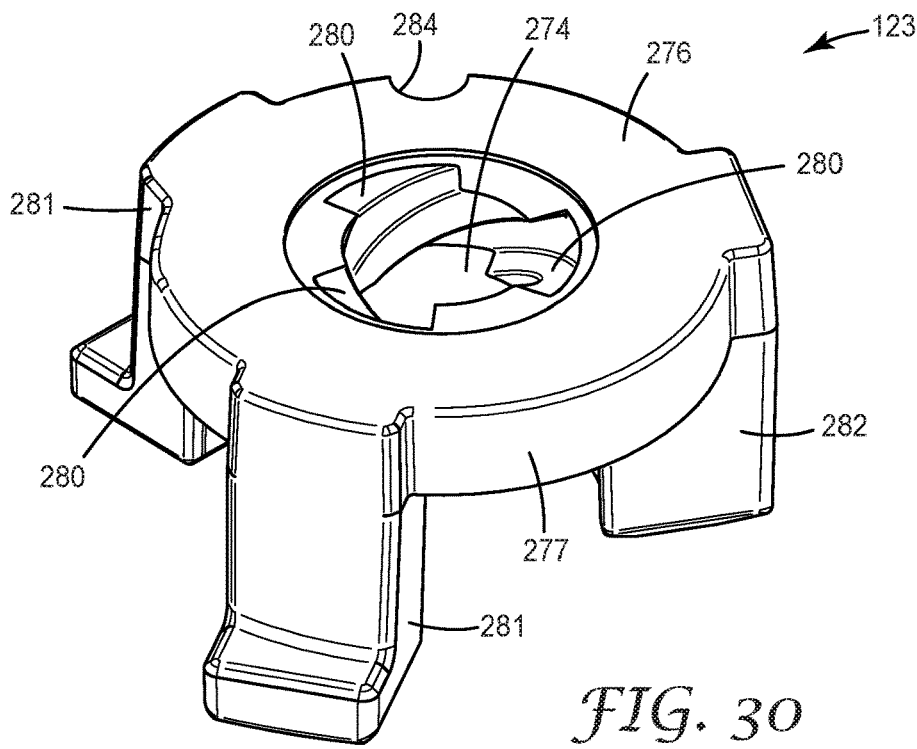
FIG. 30 is an upper side isometric view of the follower of the reusable assembly of FIG. 2.
Figure 31:
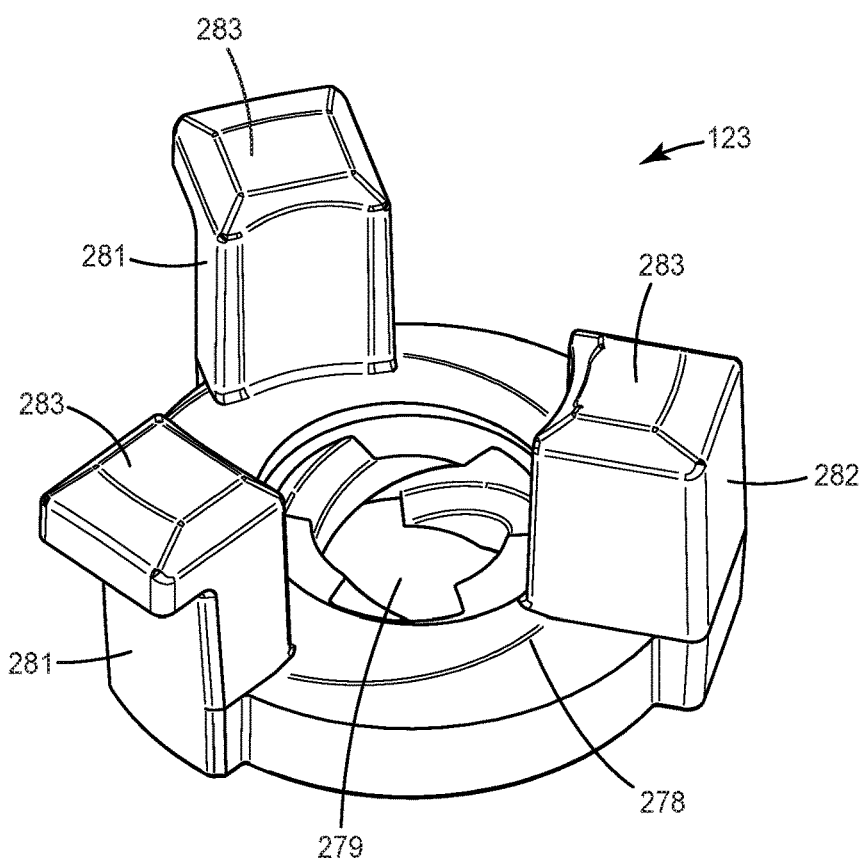
FIG. 31 is a lower side isometric view of the follower FIG. 30.

The follower 123 of the reusable assembly 109 is shown in FIGS. 30 and 31. The follower 123 comprises a top section 276, a body section 277 and a base section 278. Positioned centrally in the top section 276 is worm gear receiver 279 that extends from the top section 276 to the bottom section 278. The worm gear receiver 279 contains helical tracks 280 pitched and spaced to receive the worm gear 273 of the lead screw 122 (FIG. 29). The follower 123 further comprises three projections extending from the base section 278 in the form of two front legs 281 and one rear leg 282. The bases 283 of the two front legs 281 and the one rear leg 282 are arranged in such a manner that they make good contact with the curved base of the canister 114.

The follower 123 is sized such that at least a proportion of it, during certain stages of inhaler 100 usage, is received by the inner chamber 272 of the lead screw 122 (FIG. 29). In addition, a recess 284 exists that extends from the top section 276 through to the base section 278.

Figure 32:
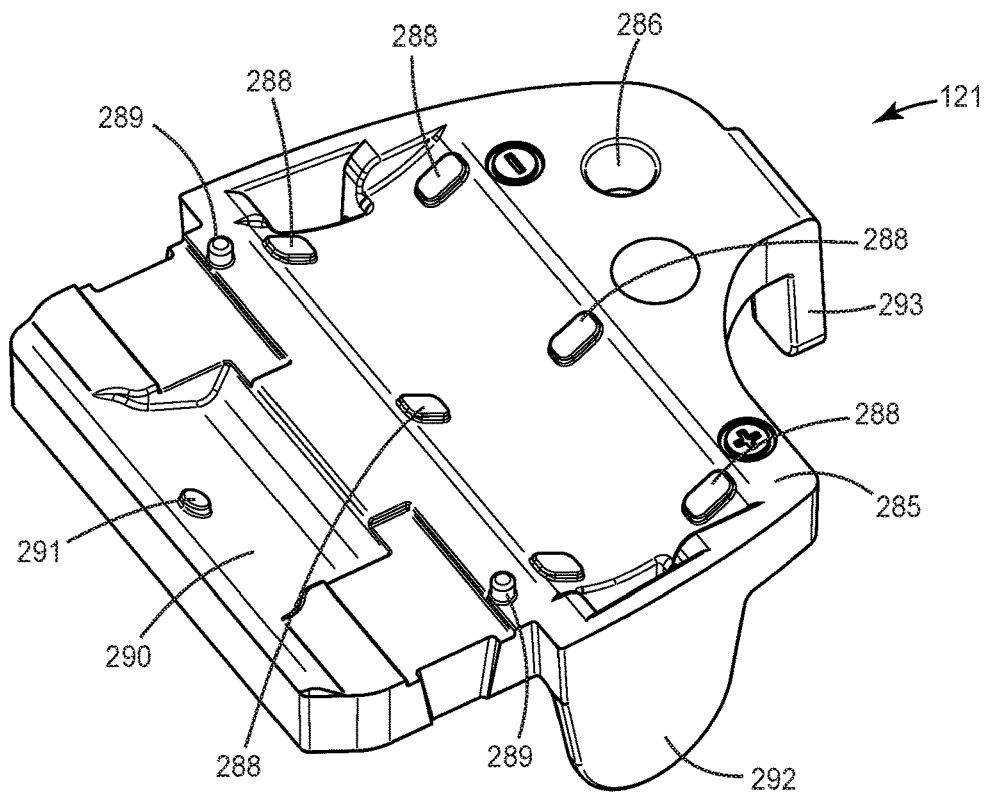
FIG. 32 is an upper side isometric view of the rocker plate of the reusable assembly of FIG. 2.
Figure 33:
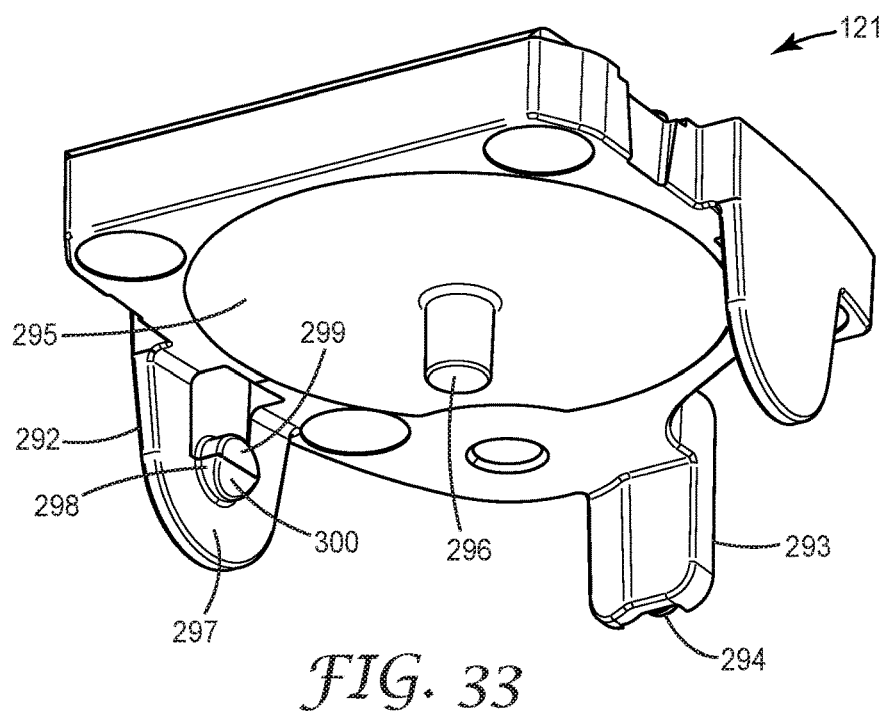
FIG. 33 is a lower side isometric view of the rocker plate of the FIG. 32.

The rocker plate 121 of the reusable assembly 109 is shown in FIGS. 32 and 33. The rocker plate 121 comprises a top section 285 that further comprises an axle hole 286 and a cell recess 287 that further comprises six cell support tabs 288. The top section 285 additionally comprises two pins 289 and a motor position sensor recess 290 that is sloped and which has at its leading edge a detent 291. Extending from the top surface 285 are two legs 292 that are positioned in line with the cell recess 287. Towards the rear of the rocker plate 121 is a support 293 that further comprises a tab 294. On a base section 295 of the rocker plate 121, positioned out of alignment with the legs 292, is an axle 296. The axle 296 is dimensioned such that it can be loosely received by socket 271 of the lead screw 122 (FIG. 28). On the inner sides 297 of the legs 292 there are axles 298. (Note that only one can be seen in FIG. 33.) The axles 298 have a top flat section 299 and a bottom sloped section 300.

Figure 34:
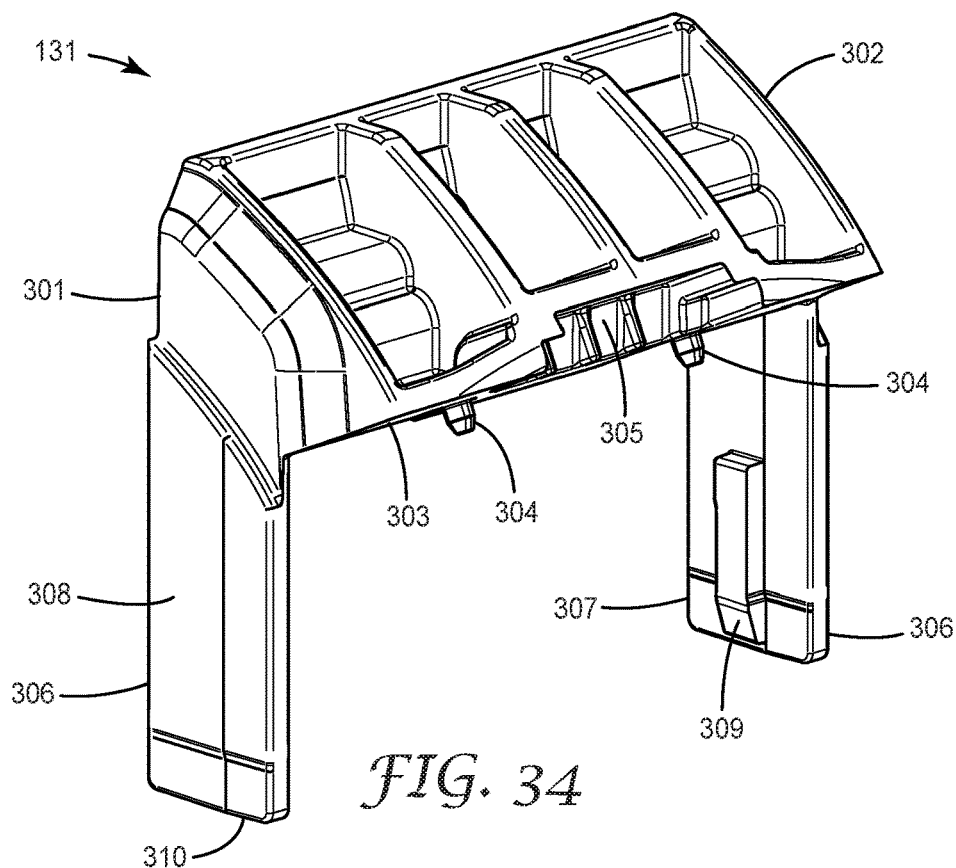
FIG. 34 is an upper side isometric view of the bridge of the reusable assembly of FIG. 2.

The bridge 131 of the reusable assembly 109 is shown in FIG. 34. The bridge 131 comprises a main body 301 that has a top angled section 302 and a bottom angled section 303. The top angled section 301 provides support for part of the front outer housing 108 (FIG. 3). The bottom angled section 302 comprises two pins 304 and a motor position sensor A recess 305. Extending from, the main body 301 are two legs 306 that each have an inner surface 307 and an outer surface 308. On the inner surface 307 of each is an inner spline 309 and on the outer surface of each is an outer spline 310.

Figure 35:
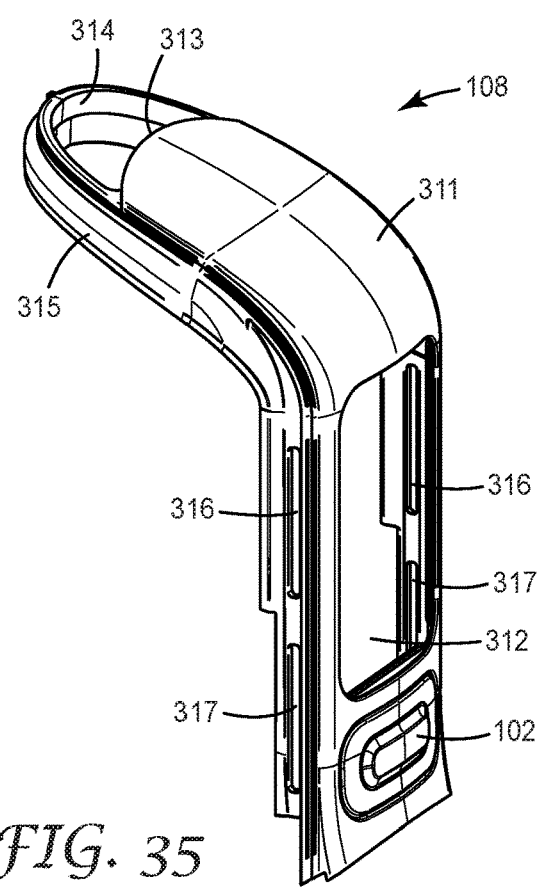
FIG. 35 is a front side isometric view of the front outer housing of the reusable assembly of FIG. 2.

The front outer housing 108 of the reusable assembly 109 is shown in FIG. 35. The front outer housing 108 comprises an outer surface 311 located in which is a display screen cover recess 312, the control button 102 and a grille recess 313. The front outer housing 108 further comprises a hooped rib 315 with an inner surface 314. Disposed in the rib 315 are two top slots 316 and two bottom slots 317.

Figure 36:
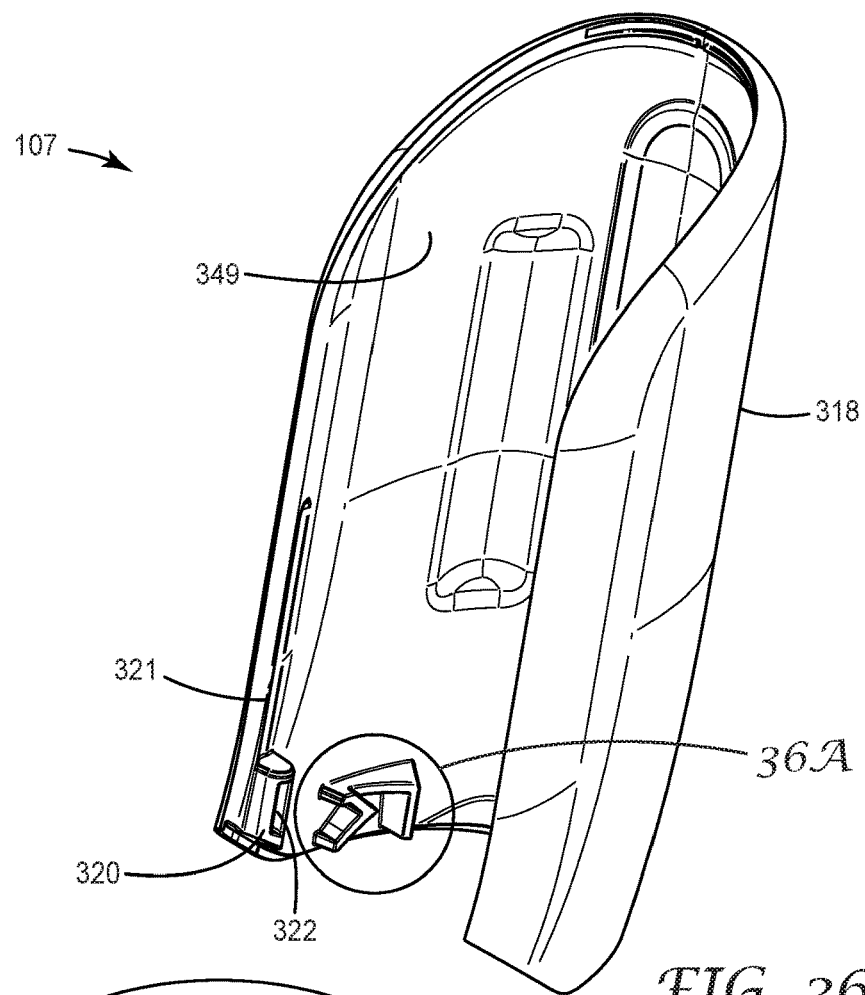
FIG. 36 is a rear right side isometric view of the rear outer housing of the reusable assembly of FIG. 2.
Figure 36A:
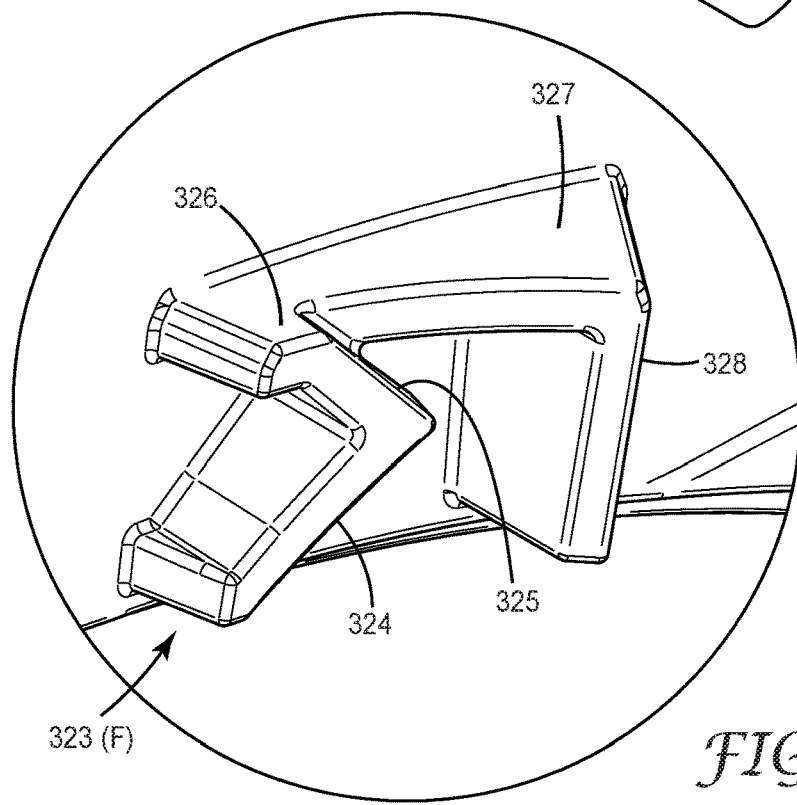
FIG. 36A is an exploded rear right side isometric view of the rear outer housing of the reusable assembly of FIG. 2 showing features of FIG. 36 in greater detail.
Figure 37:
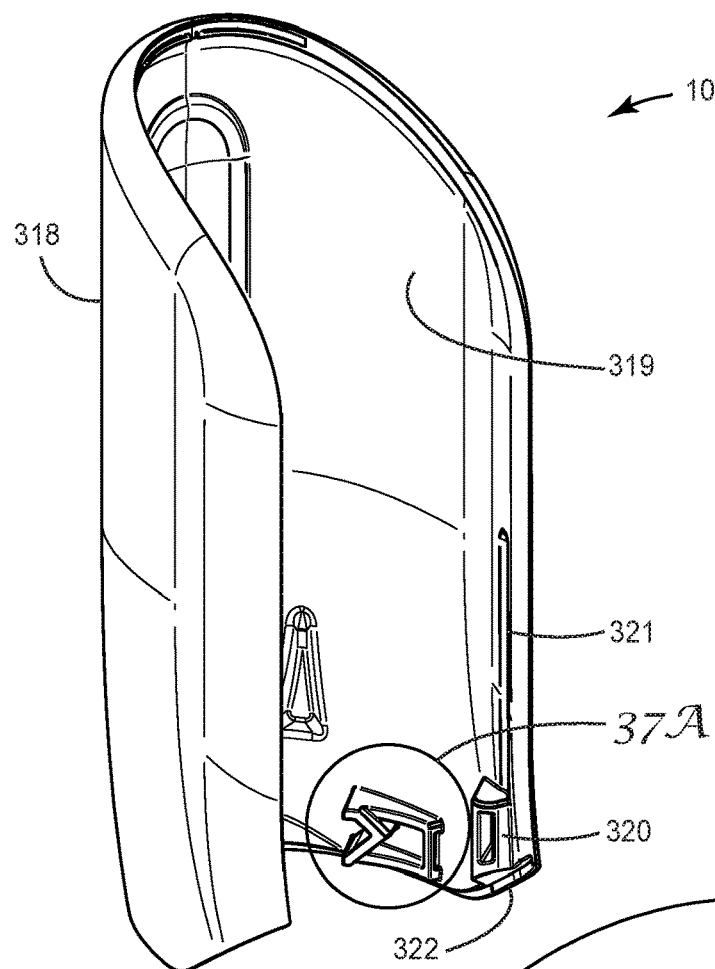
FIG. 37 is a rear left side isometric view of the rear outer housing of the reusable assembly of FIG. 2.

The rear outer housing 107 of the reusable assembly 109 is shown in FIGS. 36 and 37. The rear outer housing 107 comprises an outer surface 318 and an inner surface 319. The rear outer housing 107 is essentially "C" shaped, and is dimensioned to mate with the front outer housing 108 (FIG. 35). Located on the inner surface 319 towards the bottom are two ribs 320, above which are two biasing element recesses 321 that run axially up the ends of the outer housing 107. Referring to FIGS. 36 and 36A, at the bottom end 322 of the rear outer housing 107 is a tooth 323. This tooth 323 comprises a lower sloped surface 324, an upper sloped surface 325 and a top flat surface 326. The top flat surface 326 of the tooth 323 is connected to an elongated flat surface 327. The elongated flat surface is wedge shaped, thus only partially obscuring the upper sloped surface 325 of the tooth 323. Extending axially from the elongated flat surface 327 is a straight side surface 328.

Figure 37A:
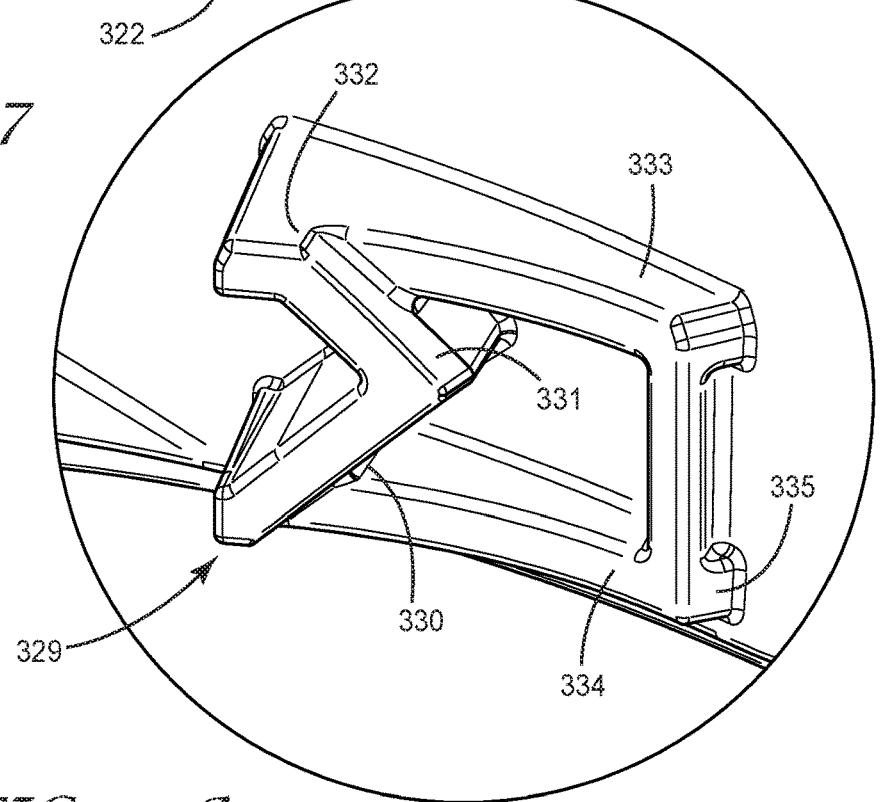
FIG. 37A is an exploded left right side isometric view of the rear outer housing of the reusable assembly of FIG. 2 showing features of FIG. 37 in greater detail.

Referring to FIGS. 37 and 37A, at the bottom end 322 of the rear outer housing 107 is a tooth 329. Tooth 329 comprises a lower sloped surface 330, an upper sloped surface 331 and a top flat surface 332. Extending from the top flat surface 332 and the lower sloped surface 330 of the tooth 329 are an upper elongated flat surface 333 and a lower elongated flat surface 334, both of which are wedge shaped and thus they only partially obscure the upper sloped surface 331 and the lower sloped surface 332 of the tooth 329. Connecting the upper elongated flat surface 333 and the lower elongated flat surface 334 is a straight side surface 335.

Referring to FIG. 38, the air flow path 127 comprises an air flow path upper section 138, a flow governor 140 and an air flow path lower 141.

The air flow path upper section 138 comprises a side clip 336, a first pressure sensor port 337, an air flow path funnel receiver 338 and two bottom clips 339. It should be noted that the boundary of the pressure sensor port 337 and the air flow path funnel receiver 338 can be over-molded with a suitable material, e.g., a thermoplastic elastomer (TPE), to create an air tight seal with their respective mating parts, i.e., with the first pressure sensor 142 and the air flow path funnel 128 respectively. The air flow path lower 141 comprises a second pressure sensor port 340, a flow governor internal support 341 and two clips 342. As with the air flow path upper section 138, surfaces of the air flow path lower 141 which mate with other components can be over-molded with a suitable material, e.g., TPE, to create an air tight seal. The flow governor 140 is positioned on the internal support 341 of the air flow path lower 141. The air flow path upper section 138 can then receive the flow governor 140 and the internal support 341 and be clipped together via clips 339 and clips 342 with the air flow path lower 141 to form the air flow path 127 of the reusable.

Figure 40:
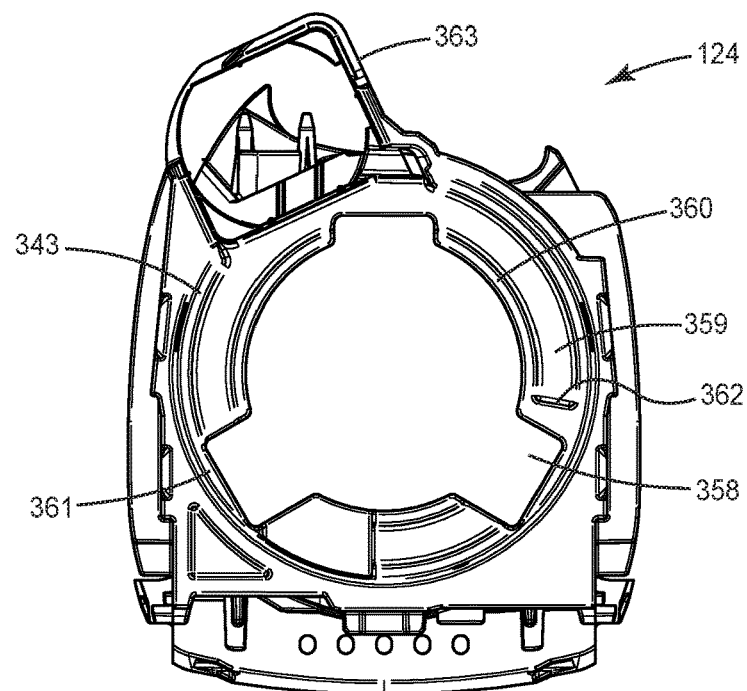
FIG. 40 is a top plan view of the chassis of FIG. 39.
Figure 41:
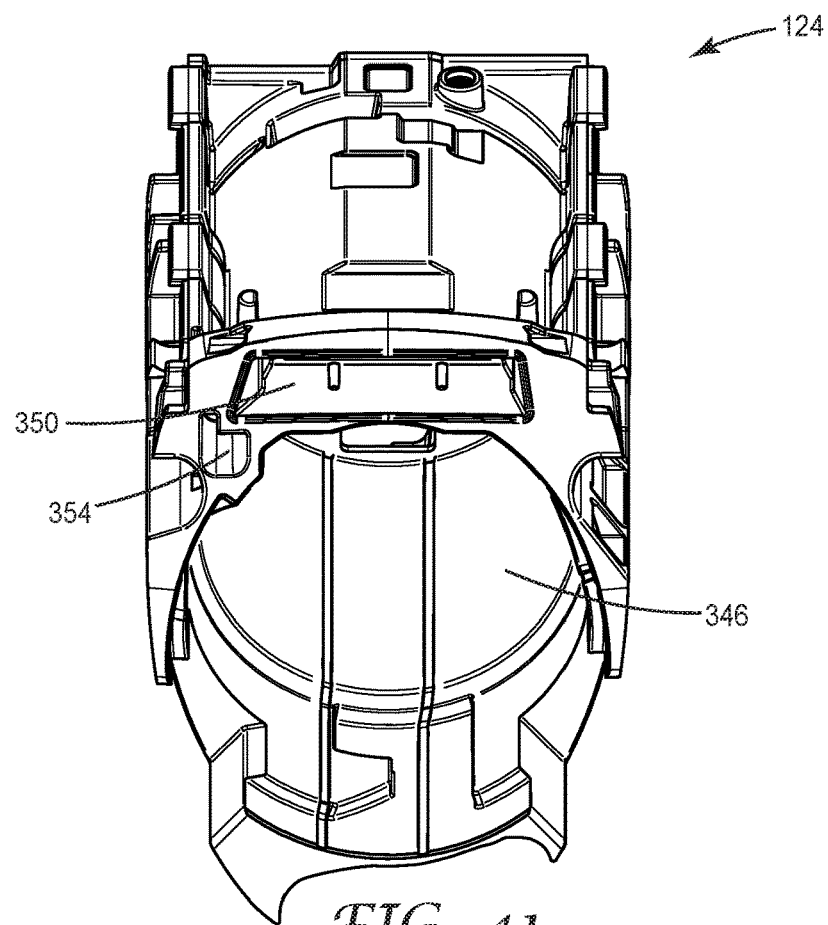
FIG. 41 is a top isometric view of the chassis of FIG. 39.
Figure 42:
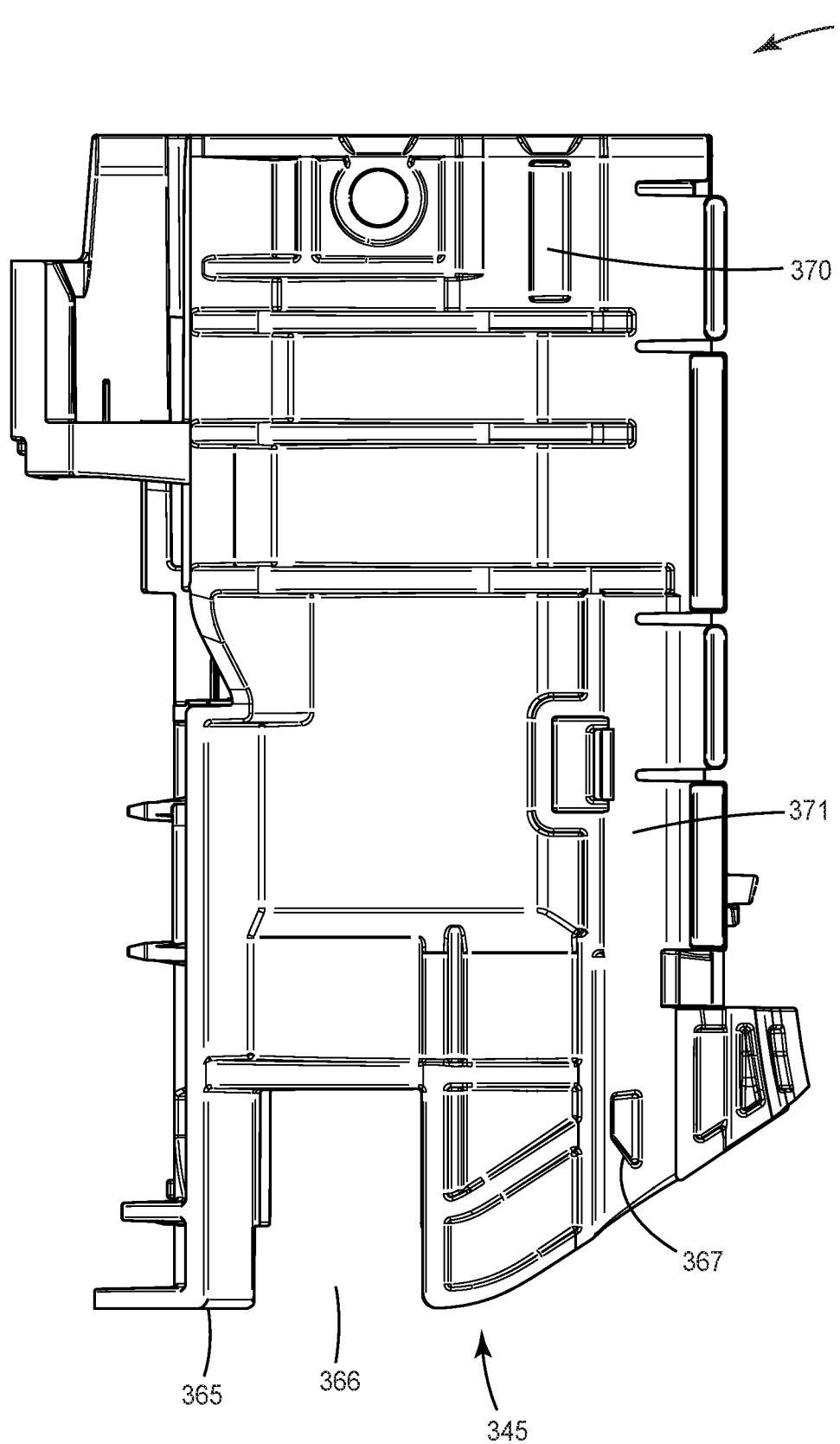
FIG. 42 is a side view of the chassis of FIG. 39.

The chassis 124 is shown in FIGS. 39 to 43. The chassis comprises a top section 343, a body section 344, a bottom section 345 and an inner chamber 346. The bottom section is shaped to mate with the air sealing cap (FIG. 42), and has a flat section 365, a recess 366 and a sloped section 367. Furthermore, on the sides of the chassis 124 there are two biasing element channels 371 (only one is shown in FIG. 42.) The inner chamber 346 is dimensioned to receive at least a portion of the refill assembly 110 and, particularly, at least a portion of the sleeve 111 and the canister 114. The chassis 124 is essentially cylindrical in shape, with numerous protrusions and recesses that facilitate interaction of other components that make up the reusable assembly 109. At the front of the chassis 124 are four ribs 347; in alignment with these are two top splines 348 and two bottom splines 349. Towards the bottom of the chassis 124 is a memory device housing recess 350, dimensioned to receive the memory device 112 and the memory device housing 179 of the refill assembly (FIG. 2).

Also towards the bottom of the chassis 124 are five conduits 351, located above the memory device housing recess 350, which allow the memory device 112 to connect to the electronic interface 147 (FIG. 3). Positioned above the conduits 351 are two pins 352 and a ledge 353, used for connecting, and supporting part of, the electronics assembly 132 (FIG. 6). To one side of the memory device housing recess 350 is a shuttle linkage recess 354. Towards the top of the chassis is a channel 355 that receives the motor sensor 148. Towards the top back is a pinion gear recess 356.

The top inner section 357 is dimensioned to receive the follower 123 (FIG. 30), which resides in a push plate recess 358. The push plate recess 358 is shaped and dimensioned such that the follower 123 is only capable of axial travel and not rotational travel. Furthermore, a channel 359 accommodates the latch 275 of the lead screw 122 (FIGS. 28 and 29). The channel 359 is defined by a channel inner wall 360, a channel outer wall 361 and a channel stop 362. The channel inner wall 360 and channel outer wall 361 act as supporting surfaces for the lead screw 122. The channel 359 provides a path/guide for the latch 275 of the lead screw 122 (FIG. 28) to travel through during rotation of the lead screw 122 (described below). The channel stop 362 ensures that the lead screw 122 is not capable of rotating through a full 360 degrees, i.e., it cannot perform a complete revolution, acting as a physical stop. For example, if the motor assembly 129 continued to drive the lead screw 122 through multiple revolutions after full axial travel of the canister 114 was achieved, e.g., due to failure of the electronic controls, this could lead to damage to the canister 114, particularly to its valve 136. This is prevented as the channel stop 362 prevents the lead screw 122 from making multiple revolutions.

Figure 43:
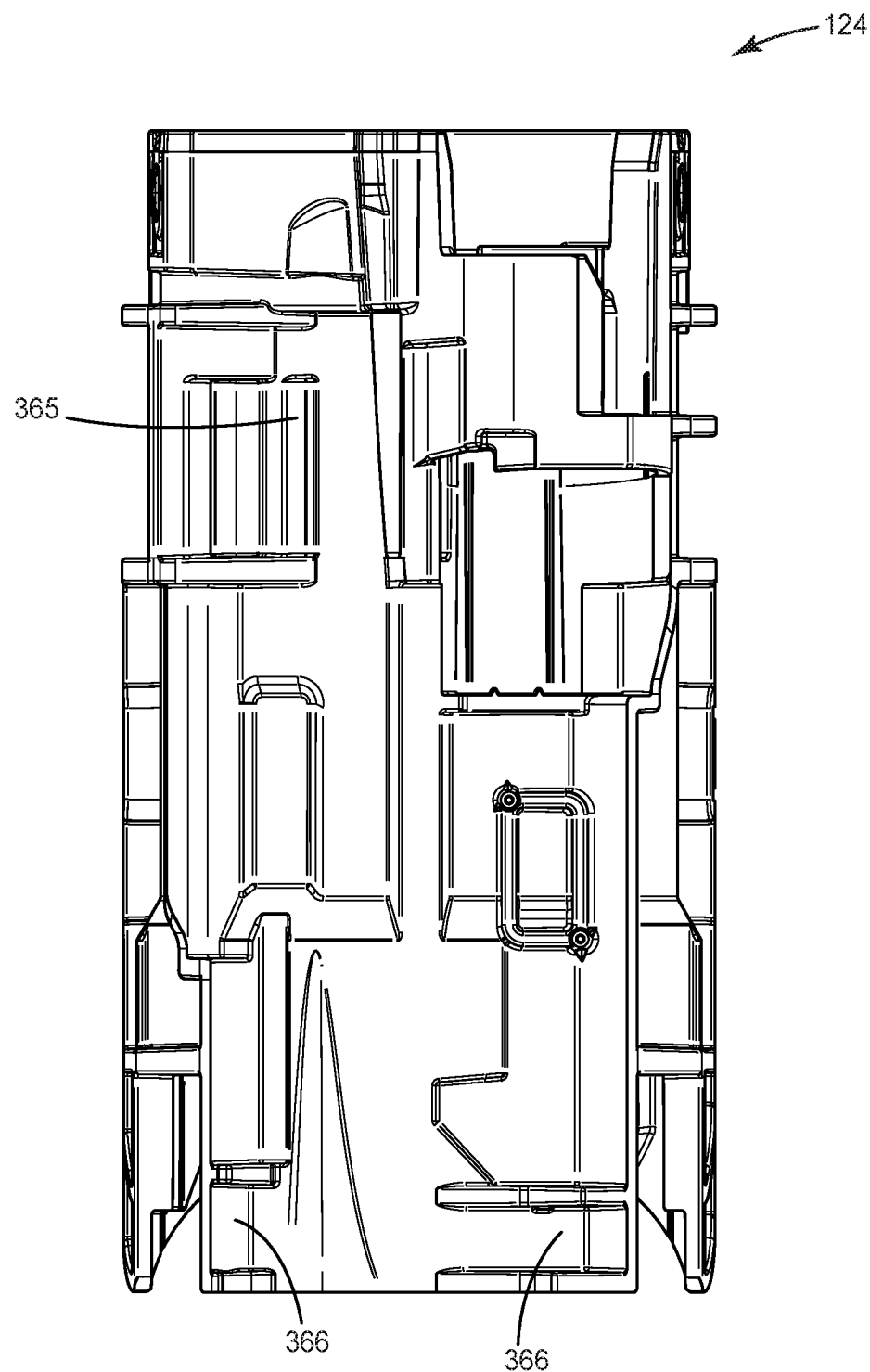
FIG. 43 is a rear view of the chassis of FIG. 39.

Towards the top of the chassis 124 are two axle receivers 364 and two slots 370, positioned on opposing sides. As shown in FIG. 43, the rear of the chassis 124 contains an airflow path upper slot 365 and two airflow path lower slots 366, for receiving the air flow path.

Figure 39:
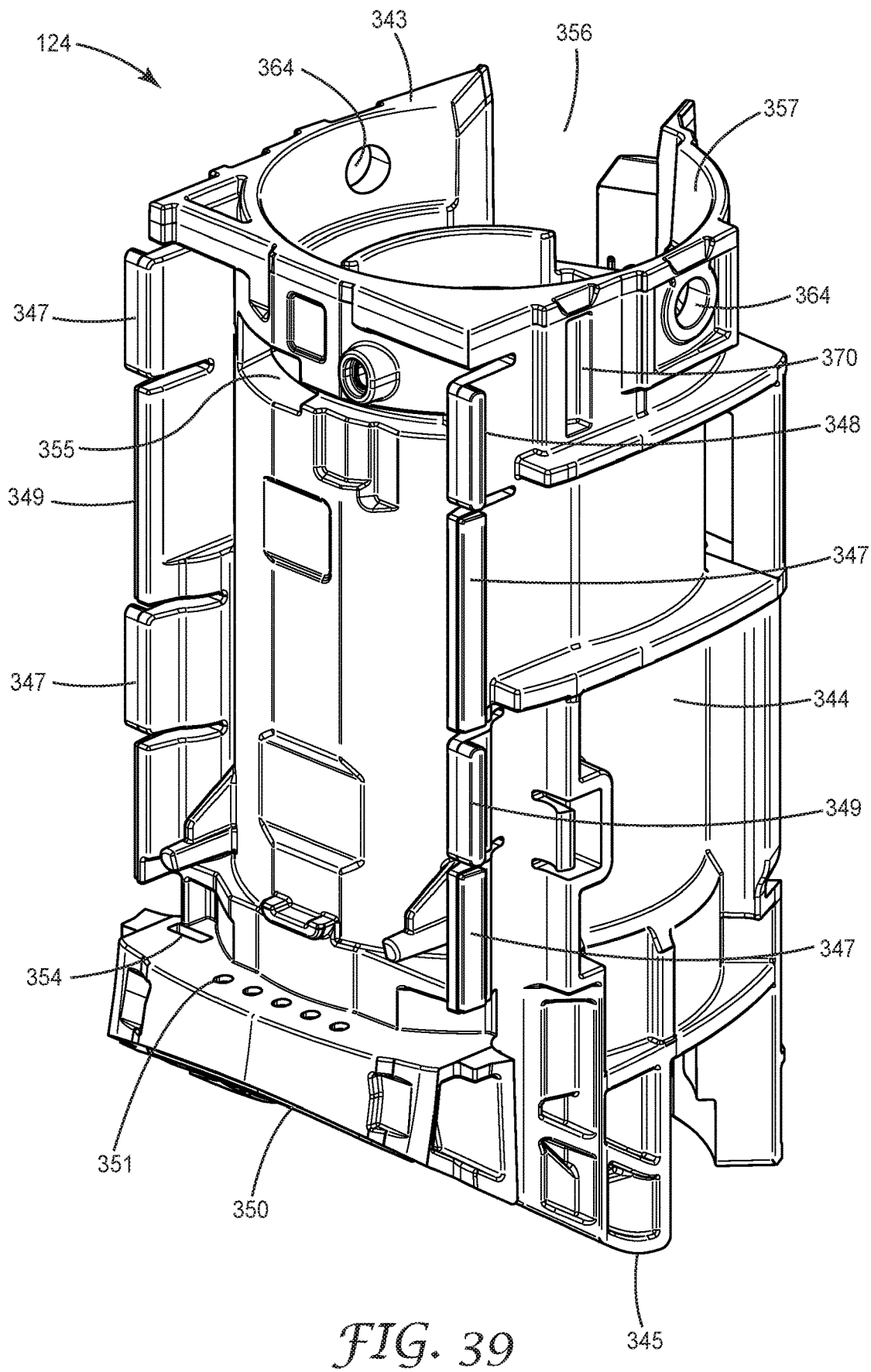
FIG. 39 is an isometric view of the chassis of the inhaler of FIG. 2.

Assembly of the reusable assembly 109 will now be described. The worm gear 273 of the lead screw 122 is received by the worm gear receiver 279 of the follower 123. The lead screw 122 and the follower 123 are received by the top inner section 357 of the chassis 124. Specifically, the follower 123 is located in the push plate recess 358 of the chassis 124, the latch 275 of the lead screw 122 is located in the channel 359 of the chassis 124 and the base 270 of the lead screw 122 locates on top of the channel inner wall 360 and the channel outer wall 361 of the chassis 124. The pinion gear 130 is connected to the motor assembly 129 (via the motor assembly axle, which is not shown), such that a proportion of the axle protrudes from the pinion gear 130, and the motor assembly 129 is inserted into the motor assembly receiver 363 of the chassis 124, thereby bringing about tooth to tooth engagement between the pinion gear 130 and the lead screw 122. The rocker plate 121 is clipped onto the chassis 124, which is achieved by locating the axles 298 on the legs 292 of the rocker plate 121 (FIG. 33), in the axle receivers 364 of the chassis 124 (FIG. 39).

As shown in FIG. 33, and as described previously, the axles 298 of the legs 292 of the rocker plate 121, comprise lower sloped sections 300 which assist the clipping of the axles 298 into the axle receivers 364. Additionally, the axle 296 of the rocker plate 121 locates in the socket 271 of the lead screw 122. As mentioned previously, the axle 296 sits in the socket 298 with a loose fit, such that the rocker plate 121 is able to rock. Furthermore, the portion of the axle of the motor assembly 129 that protrudes from the pinion gear 130 is received by the axle hole 286 in the rocker plate 121. Thus the rocker plate 121 retains the motor assembly 129, the pinion gear 130, the lead screw 122 and the follower 123 in their positions in the chassis 124. However the engagement of the axles 298 of the rocker plate 123 with the axle receivers 364 of the chassis 124 allows the rocker plate to pivot about them, i.e., to rock back and forth slightly. The air flow path 127 is attached to the chassis 124 via the clip 336 of the air flow path 127, engaging with the airflow path upper slot 365 of the chassis 124. The bottom of the air flow path 127 engages with the air flow path lower slots 366 of the chassis 124. The cover switch linkage 120 is located in the shuttle linkage recess 354 of the chassis 124.

The electronics assembly 132 (FIGS. 6 and 7) is connected to the chassis 124 such that the electronic interface 147 engages with the conduits 351 of the inhaler chassis 124, the patient port cover sensor 150 engages the cover switch linkage 120 and the motor position sensor B 150 is received by the channel 355, such that part of the motor position sensor B 150 is located in the channel 359 of the chassis 124. The controller 149 and the display screen 155 are secured in place by engagement with the pins 351 and the ledge 353 of the chassis 124, and are supported by abutting the ribs 357 of the chassis 124.

The motor position sensor 145 is located in the motor position sensor recess 290, on top of the detent 291, of the rocker plate 121. The cell 146 is located in the cell recess 287, supported by the cell support tabs 288 of the rocker plate 121. The pins 289 and the tab 294 of the rocker plate 121 interact with parts of the electronics assembly 132 (e.g., with the flexible connections) to bring about a degree of securement of the electronics assembly 132. The first pressure sensor 142 and the second pressure sensor 143 of the electronics assembly 132 are located in the first pressure sensor port 337 and the second pressure sensor port 340 respectively of the air flow path 131. The clip 126 is positioned about the airflow path 131, thus securing the first pressure sensor 142 and the second pressure sensor 143 in the first pressure sensor port 337 and the second pressure sensor port 340 to provide an air tight seal. The motor assembly 129 is connected to the electronics assembly 132.

The inner splines 309 of the bridge 131 locate in slots 370 in the chassis 124, thus securing the bridge 131 to the chassis 124. This provides additional securement of the electronics assembly 132 via its engagement with the pins 304 of the bridge 131 along with the motor position sensor A 145 being received by the motor position sensor recess 305 of the bridge 131.

The airflow path funnel 128 is attached (e.g., laser welded or ultrasonically welded) to the front outer housing 108, below the grille recess 313, and the grille 119 is received by the grille recess 313. The display cover 102 is located in the display cover recess 312. The front outer housing 108 is then attached to the chassis 124 via the top slots 316 and bottom slots 317 of the front outer housing 108 receiving the top splines 348 and bottom splines 349, respectively, of the chassis 124 (see FIG. 3). Furthermore, the airflow path funnel 128 is received by the airflow path funnel receiver 338 of the air flow path 127 (FIG. 38). Additional the control button 102 contacts the control button contacts 156 (FIG. 6).

The biasing elements 125 are located in the biasing element channels 371 of the chassis 124 (FIG. 42). The rear outer housing 107 is attached to the chassis, by clipping of the ribs 320 of the rear outer housing 107 (FIGS. 36 and 37) into the biasing element channels 371 of the chassis 124, whereby the ribs are positioned underneath the biasing elements 125. Tooth 323 and tooth 329 of the rear outer housing 107 (FIGS. 36 and 37) are received by recesses 368 of the chassis 124 (FIG. 42). The front outer housing 108 and the rear outer housing 107 are then joined (e.g., by ultrasonic welding or laser welding). Once joined, the front outer housing 108 and the rear outer housing 107 are capable of simultaneous axial travel relative to the chassis 124.

Figure 44:
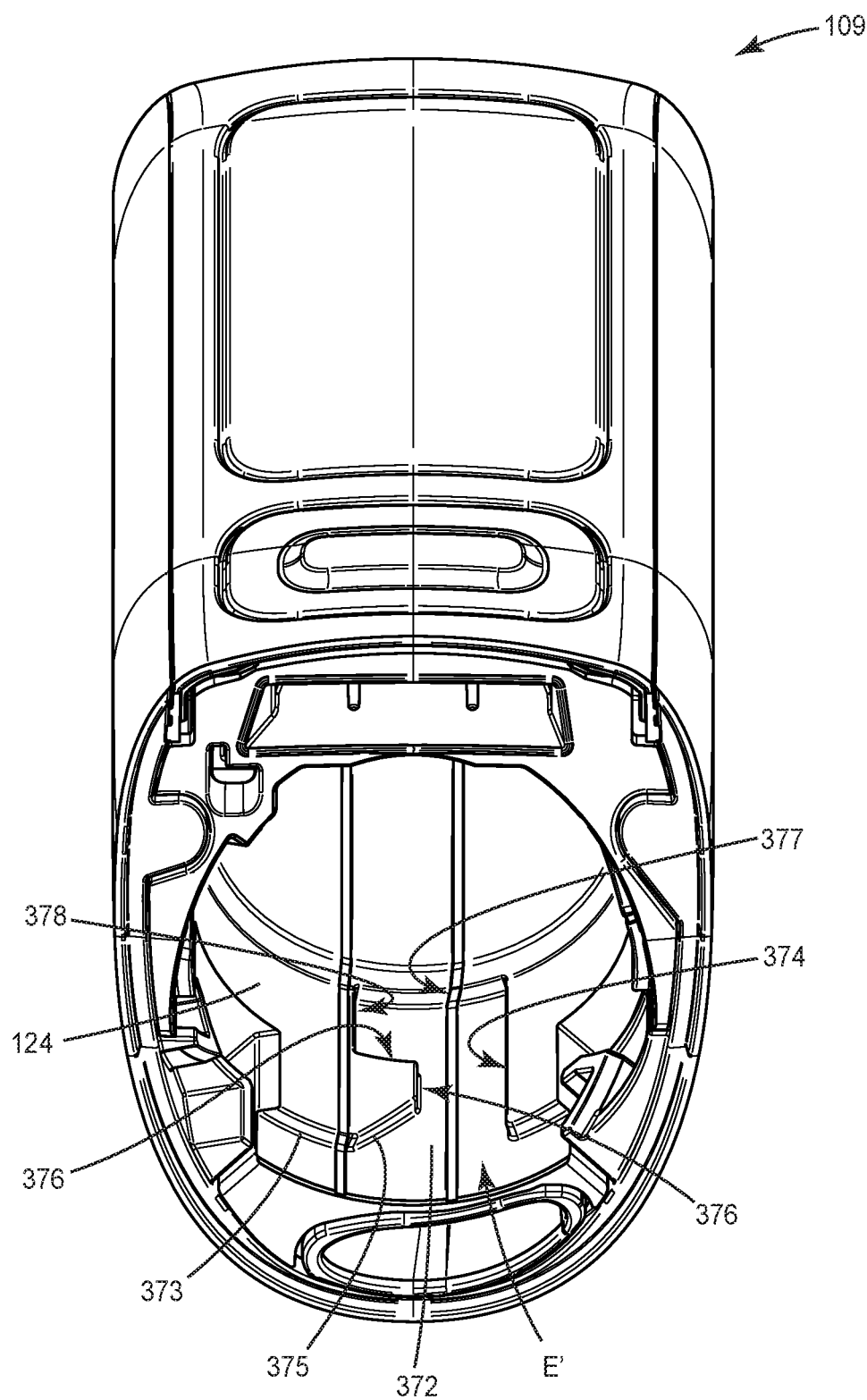
FIG. 44 is a lower isometric view of the reusable assembly of FIG. 2.

Connection of the refill assembly 110 and the reusable assembly 109 is achieved by pushing the refill assembly 110 and the reusable assembly 109 together along axis A (FIG. 2), with the sleeve 111 being received by the inner chamber 346 of the chassis 124 (FIG. 41). As mentioned above, the reusable assembly 109 has one or more engagement features that are configured to engage with the engagement features of the reusable assembly, and in some embodiments, the chassis 124 can include one or more of these features. For example, the chassis 124 can include one or more sockets or recesses dimensioned to receive a post or a tooth of the sleeve 111. By way of example, as shown in FIG. 44, the chassis 124 can include a tooth socket 372 located towards its bottom, having a lower flat edge 373, a side flat edge 374, a sloped edge (or angled wall) 375, a mid short flat edge 376, a top edge 377, an upper flat edge 378 and a ledge (or axial stop) (e.g., a flat, e.g., horizontal, ledge) 379, which are all positioned and configured to control or direct movement of the tooth 235 of the sleeve 111 when the refill assembly 110 and reusable assembly 109 are coupled together. For example, the lower flat edge 273 is shaped to guide the tooth 235 to the sloped edge 375; the sloped edge 375 is shaped to allow axial and rotational movement between the tooth 235 and the tooth socket 372; and the ledge 379 is shaped to allow for relative rotational movement between the tooth B 235 and the tooth socket 372. The edges 373, 374, 375, 376, 377 and 378 can instead by referred to as surface, walls, sections, portions, or the like.

Figure 45:
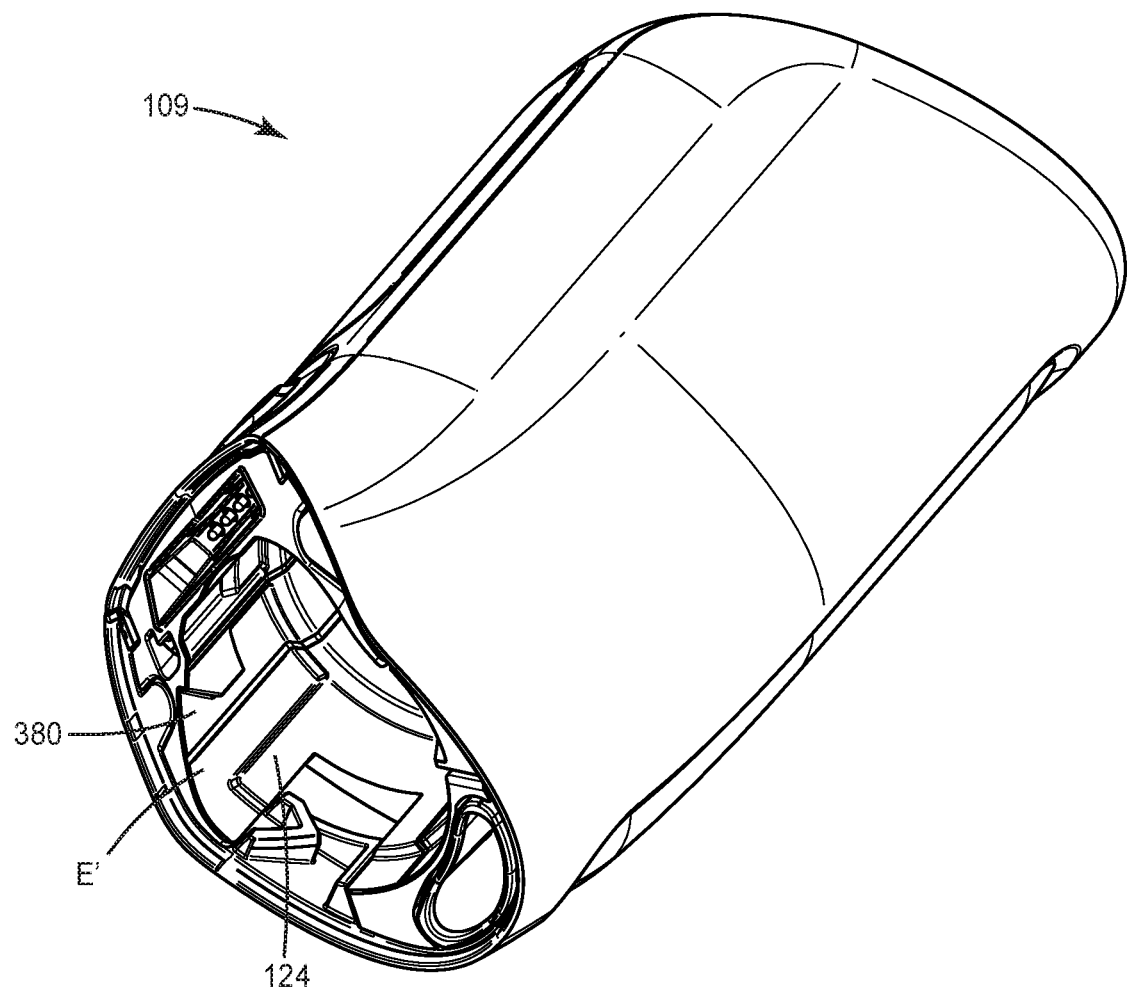
FIG. 45 is a lower side isometric view of the reusable assembly of FIG. 2.
Figure 46:
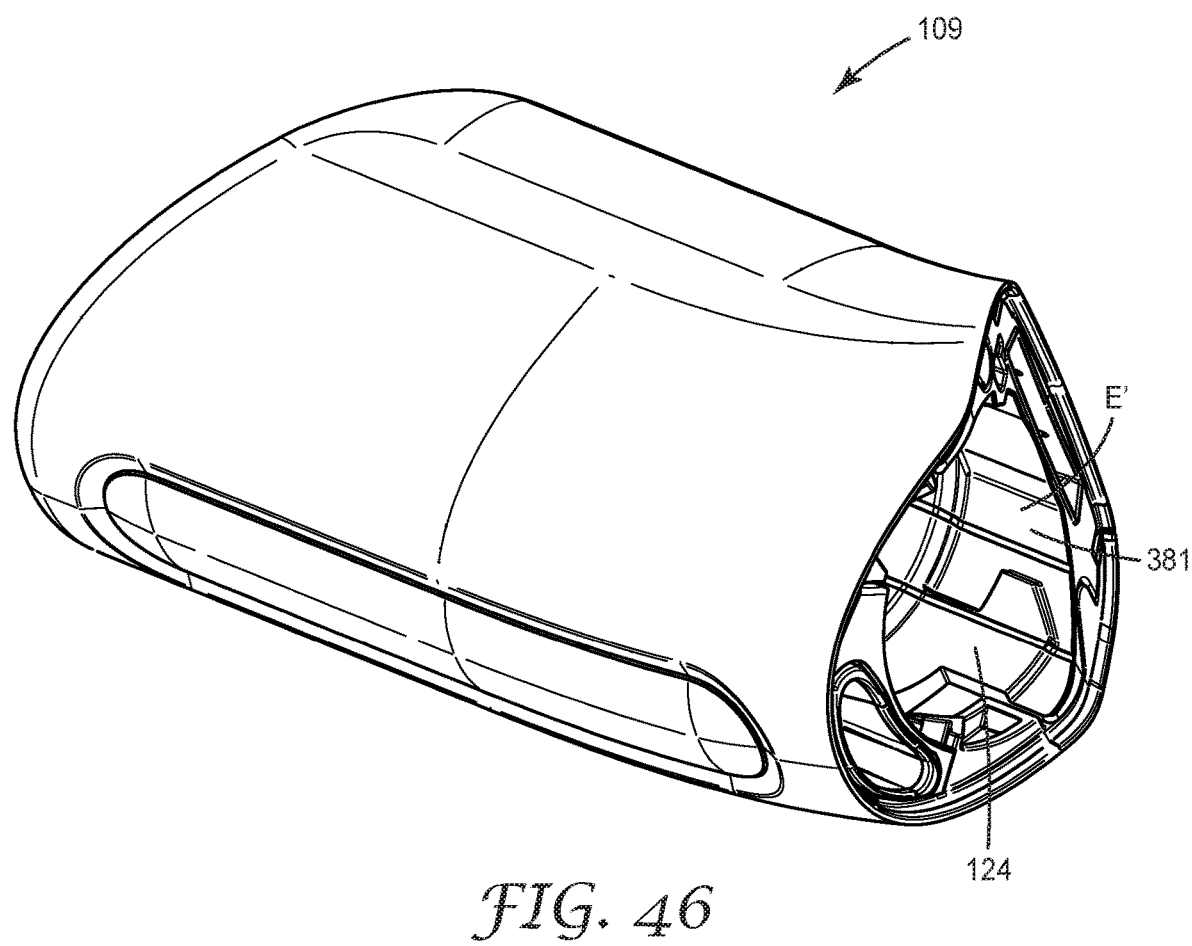
FIG. 46 is a further lower side isometric view of the reusable assembly of FIG. 2.

FIGS. 44 to 46 show the reusable assembly from different angles. FIG. 45 shows that in some embodiments, the reusable assembly 109, specifically the chassis 124, can include a tooth socket A 380 dimensioned to receive the tooth 234 of the sleeve 111. FIG. 46 shows that in some embodiments, the reusable assembly 109, specifically the chassis 124, can further include a tooth socket 381 dimensioned to receive the tooth 236 of the sleeve 111. By way of example only, the tooth socket A 380 and the tooth socket 381 are the same size and shape and have the same features (e.g., edges) as previously described for the tooth socket B 372.

When the refill assembly 110 is coupled to the reusable assembly 109, the first engagement features E of the sleeve 111 engage with the second engagement features E' of the reusable assembly 109 to cause the sleeve 111 to move from a first position to a second position and then to return to its first position and to inter-engagingly couple the refill assembly 110 and the reusable assembly 109 together. By way of example only, in the present embodiment when the refill assembly 110 is coupled to the reusable assembly 109, the tooth 234, tooth 235 and tooth 236 on the sleeve 111 engage with the tooth socket 380, tooth socket 272 and tooth socket 231 of the chassis 124 respectively.

The interaction, i.e., engagement, of the tooth 235 of the sleeve 111 and the tooth socket B 272 of the chassis will now be described in greater detail. It should be understood that in the present embodiment the engagement of tooth 234 with tooth socket 380, as well as the engagement of tooth 236 with tooth socket 381, is identical to that of tooth 235 with tooth socket 272. As a result, reference is made to FIGS. 47A to 47D and their accompanying description for these interactions as well.

FIGS. 47A to 47D schematically illustrate the interaction of a first engagement feature E (e.g., a post or a tooth) of the sleeve 111 of the refill assembly with a second engagement feature E' (e.g., a socket dimensioned to receive a post) of the reusable assembly 109 (e.g., of the reusable assembly chassis 124). More specifically, for the present embodiment FIGS. 47A to 47D schematically illustrate the interaction of the tooth 235 of the sleeve with the tooth socket 272.

As shown, the one or more first engagement features E of the sleeve 111 of the refill assembly 110 and the second engagement features E' of the chassis 124 of the reusable assembly 109 are movable relative to one another from a first position to a second position and back to the first position.

Figure 47A:
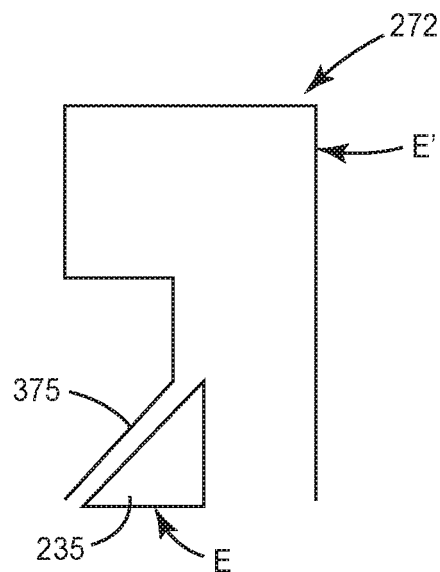
FIGS. 47A to 47D show features of the reusable assembly shown in FIG. 46 in greater detail.
Figure 47C:
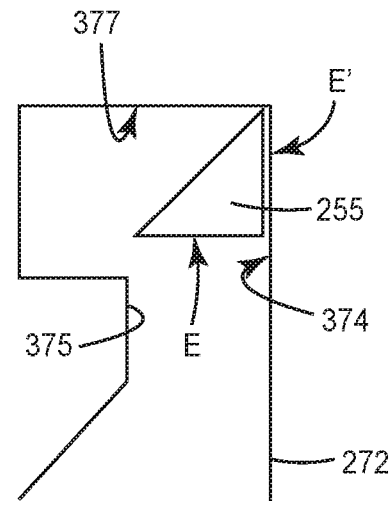
Figure 47B:
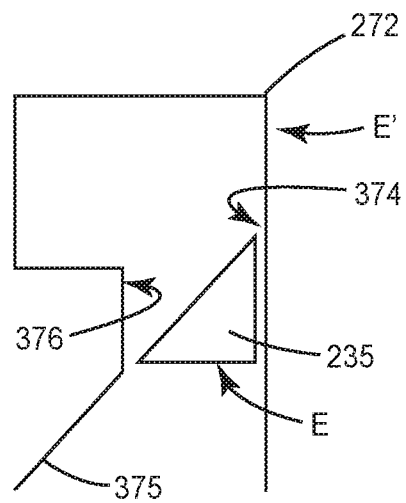

FIG. 47A shows that tooth 235 abuts the sloped edge 375 of the tooth socket 272 as the refill assembly 110 and reusable assembly 109 are brought together (e.g., by moving the refill assembly 110 and the reusable assembly 109 axially together, in the axial direction). As shown in FIG. 47B, as additional force (e.g., in the axial direction) is applied to one or both of the refill assembly 110 and the reusable assembly 109 towards one another, the tooth 235 moves further along, e.g., cams along, the sloped edge 375 causing clockwise rotation of the sleeve 111 (e.g., about the axis A). This rotation also results in simultaneous movement of (i.e., rotation of) the boss 244 of the sleeve 111 against the bias of the biasing element 229 of the air sealing cap 106, e.g., resulting in the biasing element 229 being compressed against its biasing force.

Clockwise rotation of the sleeve 111 ceases when tooth 235 disengages with the sloped edge 375 and engages with the side flat edge 374 and/or the mid flat edge 376 of the tooth socket 372. As additional force (e.g., in the axial direction) is applied to one or both of the refill assembly 110 and the reusable assembly 109 towards one another, the tooth 235 moves further up the side flat edge 374 and mid flat edge 376.

Figure 47D:
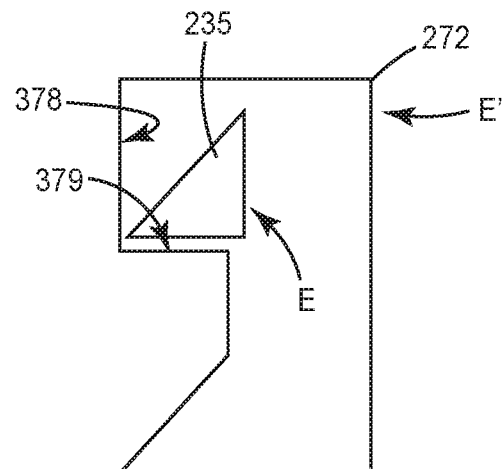

Axial travel ceases when the tooth 235 disengages with the mid flat edge 376 and engages with the top edge 377 of the tooth socket 272. At this point the biasing element 229 of the air sealing cap is able to decompress, and the resultant force acts on the boss 244 of the sleeve 111, resulting in counter-clockwise rotation of the sleeve 111. The counter-clockwise rotation of the sleeve 111 results in horizontal movement (e.g., circumferential movement illustrated as linearly horizontal for simplicity in FIGS. 47C and 47D) of tooth 235 in the tooth socket 272, up to the point where the tooth 235 contacts the upper short flat edge 378 of the tooth socket 272 and rests atop the ledge 379, as shown in FIG. 47D.

The starting position (e.g., starting circumferential or rotation position) of tooth 235 is aligned with its end position (e.g., starting circumferential or rotation position). However, the axial position of tooth 235, relative to tooth socket 372, is different.

During the process of coupling of the refill assembly 110 and the reusable assembly 109, the tooth 237 and tooth 238 of the sleeve 111 (FIG. 22) are positioned and configured to interact with tooth 323 and tooth 329, respectively, of the rear outer housing 107 (FIGS. 36 and 37). As the coupling occurs, the sloped top edges 237A and 328A of tooth 237 and tooth 238 come into contact with the tooth F 323 and tooth G 329 respectively. The clockwise rotation of the sleeve 111 caused by the first and second engagement feature E, E', which occurs as the refill assembly 110 and the reusable assembly 109 are pushed together, causes the sloped top edges 237A and 328A of tooth 237 and tooth 238 to cam along the lower sloped edges 324 and 330 of the teeth 323 and 329 respectively. The immediate subsequent counter-clockwise rotation of the sleeve 111, under the influence of the biasing element 229, causes the upper sloped edge 325 and 331 of tooth 323 and tooth 329 to engage with the sloped bottom edge 237b and 238b of tooth 237 and tooth 238 respectively.

The interaction of the tooth 234, the tooth 235 and the tooth 236 with the tooth socket 380, the tooth socket 372 and the tooth socket 381, respectively, serves to secure the refill assembly 110 to the reusable assembly 109 to prevent separation during, e.g., dispensing a dose of medication or during shaking (e.g., at least partly because of each tooth being prevented from axial movement by the respective ledge of the tooth socket).

Furthermore, coupling of the refill assembly 110 and the reusable assembly 109 brings about engagement of several other features/components. The bases 283 of the front legs 281 and the rear leg 282 of the follower 123 are received through the apertures 231 of the sleeve 111 and contact the base of canister 114 (FIG. 3), the patient port cover linkage 117 abuts the linkage shuttle 120, and the memory device 112 connects to the electronic interface 147. Thus the inhaler 100 is ready for use.

The patient uses the inhaler 100 by first opening the patient port cover 104. This results in the patient port cover linkage 117 dropping and in turn allows the linkage shuttle 120 to travel axially (urged by a biasing element, which is not shown) against the patient port cover sensor 152. The patient port cover sensor 152 communicates with the controller 149 which powers up the electronics and may lead to the display of icons and/or instructions on the display screen, thus prompting the patient to perform certain actions (e.g., shake the inhaler, prime the inhaler) as described previously (FIG. 8A to 8C). Furthermore, the display may provide pertinent information to the patient to aid with management of their regime (e.g., type of medicament, time since last medicament dose was taken, number of medicament dosages remaining in the refill assembly). Indeed, the display 155 may be used to display any pertinent information to the patient at any stage during the use of the inhaler, in ways that will be obvious to one skilled in the art.

Once the patient has performed required actions, prompted by the instructions provided on the display 155 (e.g., shaking of the inhaler, priming of the inhaler), the patient can take their dose of medicament.

Figure 50A:
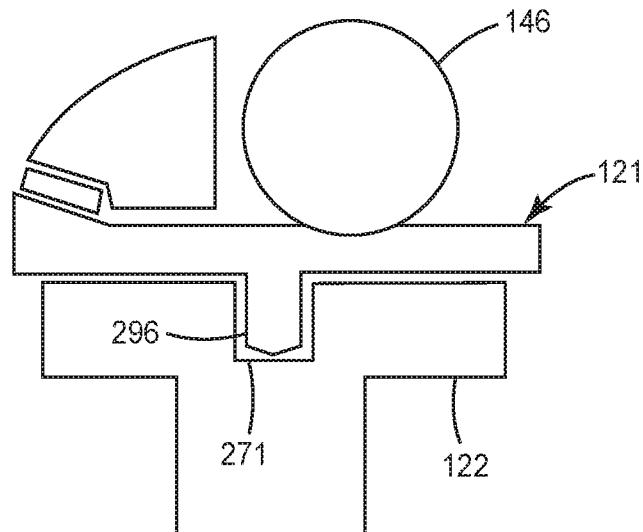
FIG. 50A is a schematic representation of the rocker plate of the inhaler of FIG. 2 in its first position.
Figure 50B:
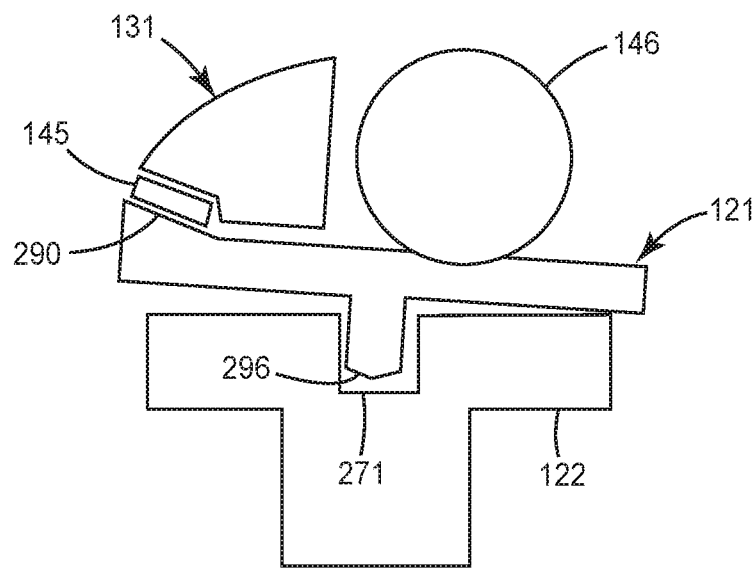
FIG. 50B is a schematic representation of the rocker plate of the inhaler of FIG. 2 in its second position.

The patient positions their lips around the patient port 133 (FIG. 3) to form a tight seal and inhales. The inhalation is sensed by one or both of the pressure sensors 142 and 143 (FIGS. 3 to 5). At a certain pressure drop (and, hence, air flow rate), the controller 149 (FIG. 5) powers up the motor assembly 129 (FIGS. 4 and 5) which, through the gear box, results in rotation of the gear pinion 130 (FIG. 4). As the gear pinion 130 is engaged with the lead screw 122 (FIGS. 28 and 29), this results in rotation of the lead screw 122, and thus rotation of the worm gear 273. Interaction of the helical threads 274 of the worm gear 273 with the helical tracks 280 of the follower 123 (FIG. 30) brings about axial travel of the follower 123 from its first rest position in which the drive mechanism is primed for use. Rotation of the follower 123 is prevented by the push plate recess 358 of the chassis 124 (FIG. 40). The follower 123 moves towards its second position and thereby transfers force to the canister 114 (FIGS. 3 and 4) bringing about axial travel of the canister 114. This causes the valve 136 to actuate and release a dose of medicament when the follower 123 reaches its second position. Once full axial travel of the canister 114 has been achieved, the increasing opposing force generated by the spring inside the valve 136 is transferred from the canister 114 through the follower 123, through the lead screw 122 and to the rocker plate 121. This causes the front end of the rocker plate 121 to pivot from its position shown in FIG. 50A. As the space between the rocker plate 121 and the bridge 131 is reduced, this leads to compression of the motor position sensor 145 as shown in FIG. 50B. The triggering of the motor position sensor 145, which is in communication with the controller 149, informs the controller 149 that the canister has reached full axial travel, i.e., that a dose of medicament has been dispensed. The controller 149 regulates the power to the motor assembly 129 sufficient to hold the canister 114 in a fired position for a defined period of time. After the elapse of this time period, the controller 149 communicates with the motor assembly 129 to reverse the drive. This causes the pinion gear 130 and the lead screw 122 to travel axially in reverse. This allows the valve 136 of the canister 114 to reset itself. The controller 149 detects when the follower 123 has reached its home position, as the latch 275 of the lead screw 122 (FIG. 29) reverses its path in the latch channel 359 of the chassis 124 (FIG. 40) to a point where it engages with the motor position sensor 148. The triggering of the motor position sensor 148, which is in communication with the controller 149, informs the controller 149 that the follower 123 is in its starting position and thus that the canister valve 136 has been allowed to reset. The controller 139 then powers down the motor assembly 129. The patient can then take another dose, if required by their dosage regimen, or close the patient port cover 104. Closing the patient port cover 104 causes the patient port linkage 117 to be moved upwards, which in turn urges the linkage shuttle 120 upwards and disengages it from with the patient port cover sensor 150. The patient port cover sensor 150 then communicates with the controller 149 that the patient port cover 104 is closed, and the inhaler 100 powers down. Prior to power-down, data collected during the use of the inhaler 100 can be written to the memory devices 112 and/or 153 as described above.

In order to remove the refill assembly 110, i.e., to decouple the refill assembly 110 and the reusable assembly 109, the patient grips the reusable assembly 109 with one hand and grips the refill assembly 110 with the other hand. When a pulling force is applied to the refill assembly 110, the front outer housing 108 and rear outer housing 107 of the reusable assembly 109 move axially upwards, due to the interaction of the ribs 320 of the rear outer housing 107 (FIGS. 36 and 37) with the biasing elements 125 (FIG. 4) in the biasing element channels 371 of the chassis 124 (FIG. 42), in addition to the interaction of the top slots 316 and bottom slots 317 of the front outer housing 108 (FIG. 35) with the top splines 348 and bottom splines 349 of the chassis 124, thereby compressing the biasing elements 125. The air flow path funnel 128 (FIG. 4), which is attached to the front outer housing 108 as described above, separates from the air flow path 127. This separation causes clockwise rotation of the sleeve due to the cam action brought by the interaction of tooth 237 and tooth 238 of the sleeve 111 (FIG. 20) with tooth 323 and tooth 329 of the rear outer housing 107 (FIGS. 36 and 37). The clockwise rotation of the sleeve causes the tooth 234, tooth 235 and tooth 236 of the sleeve 111 (FIG. 20) to disengage from the tooth socket 380, the tooth socket 372 and the tooth socket 381 (e.g., by moving out of engagement with the ledge 379 (FIG. 44) in a reverse sequence to that shown in FIGS. 47A to 47D, namely, to move the first and second engagement features E, E' from the first position (FIG. 47D) to a second position (FIG. 47C) and back to the first position (FIG. 47A). Once the refill assembly 110 is fully disengaged from the reusable assembly 109, the front outer housing 108 and the rear outer housing 107 return to the starting position urged by the biasing elements 125 decompressing.

An override mechanism of the present disclosure allows a patient to override the lockout mechanism, that is to say the mechanism that ordinarily prevents the refill assembly from dispensing medicament without being connected to the reusable assembly, of the refill assembly 110. Such an override mechanism can be important to ensure that a patient is able to receive a dose of medication if a reusable assembly 110 is not available in an emergency situation (e.g., is misplaced of lost), or if issues occur with the inhaler, e.g., if one or more of the electronic elements or mechanical elements fail. In such a situation, where a dose cannot be delivered from the inhaler, the patient can remove the refill assembly 110 from the reusable assembly 109 (as described above), if already coupled to the reusable element 109, and operate the override. The patient can then use the refill assembly as a stand-alone inhaler, e.g., as a press-and-breathe inhaler. This means that although the patient will not benefit from the timed delivery resulting from the breath-actuated firing system and from the medicament being delivered at a controlled flow rate (i.e., by virtue of the flow governor), nor from dose counting or data collection regarding time of dosing, inhalation profiles, etc., a system for emergency use is provided.

The override mechanism is designed such that it is irreversible and the refill assembly 110 cannot be coupled to, or re-coupled to, any reusable assembly 109 following use of the override mechanism. This ensures that the patient has a means by which they receive their medication until a new reusable assembly 109 and refill assembly 110 can be obtained.

Figure 27C:
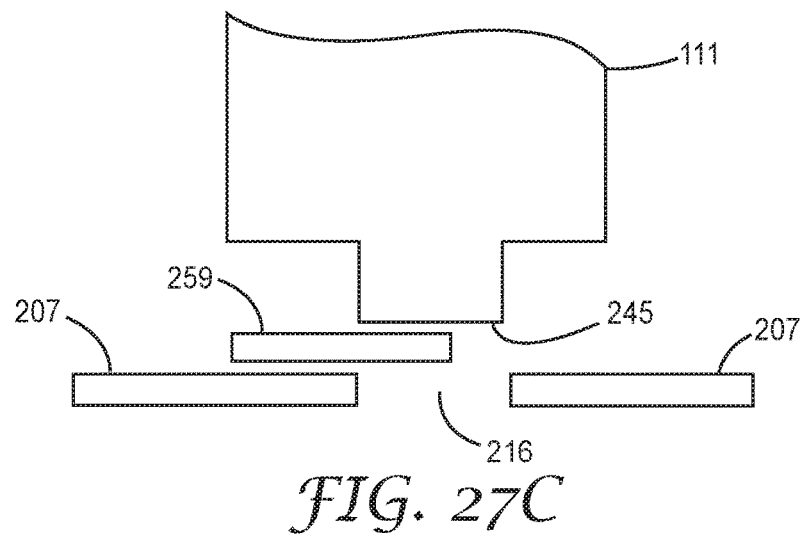
Figure 27D:
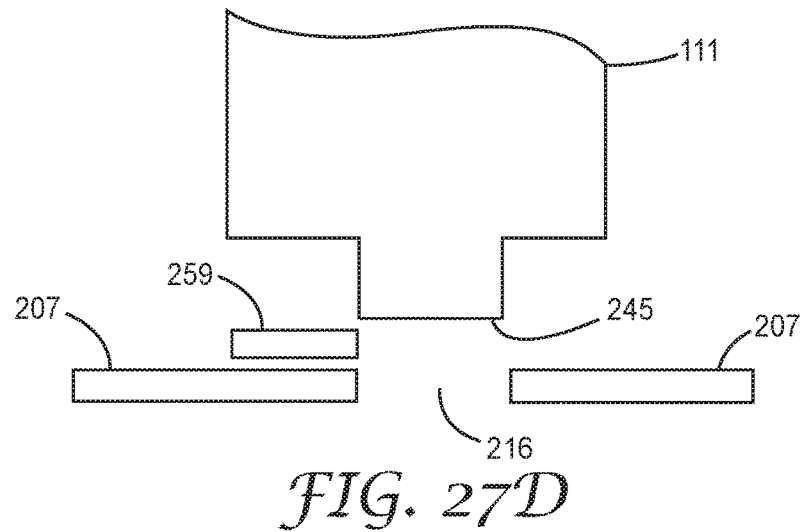
Figure 27E:
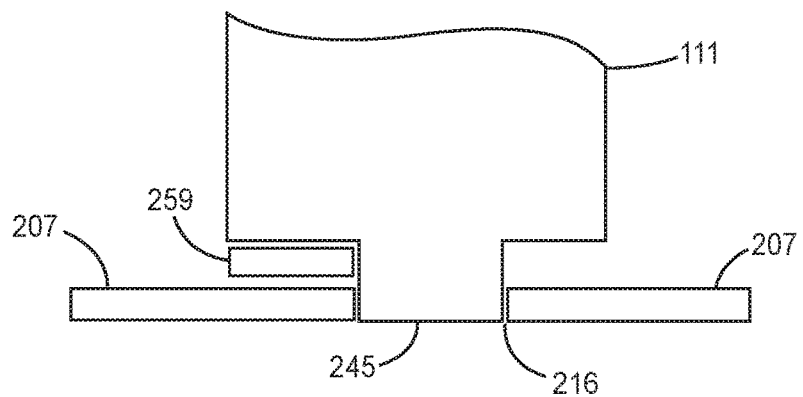
Figure 48A:
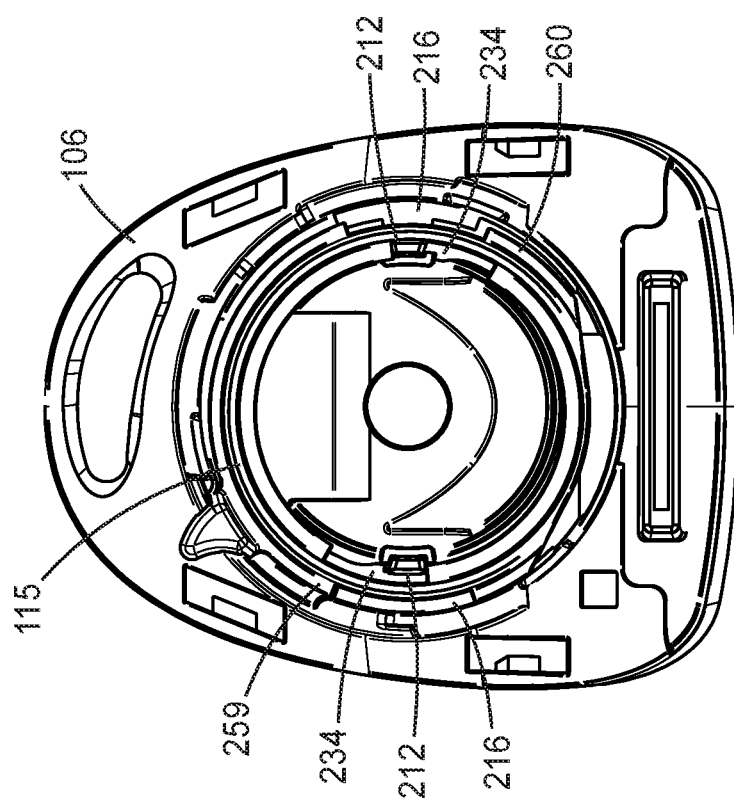
FIG. 48A is a top section view of the inhaler of FIG. 2 with the override element in its first position.
Figure 48B:
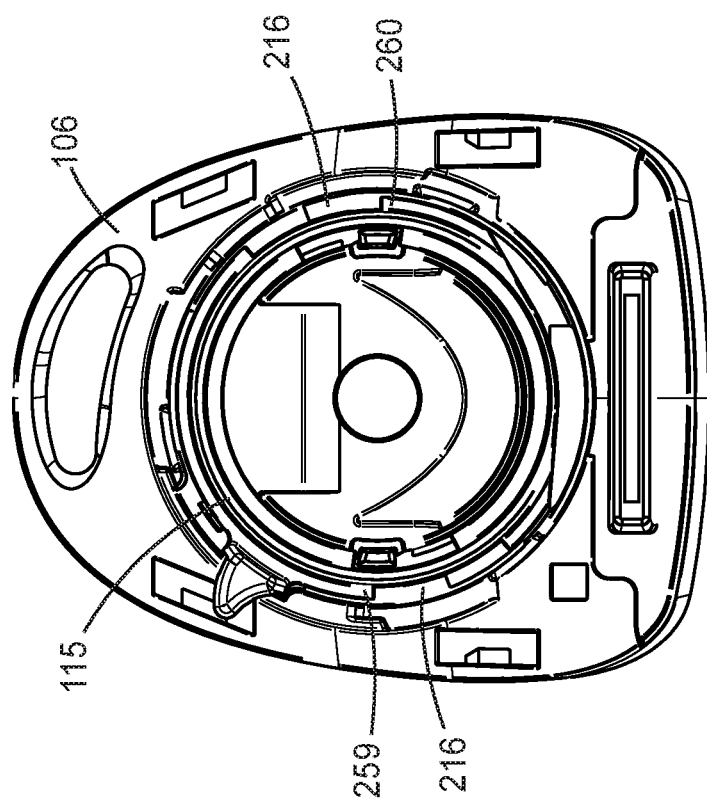
FIG. 48B is a top section view of the inhaler of FIG. 2 with the override element in its second position.

The override is operated by the patient applying force to the post 262 of the override element 115, resulting in clockwise rotation of the override element 115 through approximately 20 degree as depicted by the rotation of the override element 115 from its first position as shown in FIGS. 27B and 27C and its second position as shown in FIGS. 27D and 27E, and similarly from its first position as shown in FIG. 48A and its second position as shown in FIG. 48B. The override cannot be rotated further than this distance as the travel of the lever 263 is defined, i.e., restricted, by slot A 208 of the air sealing cap 106. The patient can then apply force to the top section 230 of the sleeve 111 which is now capable of axial travel. Hence the canister 114 can be depressed and move from its first position as shown in FIGS. 27B, 27C and 27D to its second position as shown in FIG. 27E in order to cause a dose of medicament to be released. Prior to rotation of the override element 115, the sleeve 111 is not capable of axial travel because portions of the rear outer ledge 259 and the long front outer ledge 260 cover portions of the "T" shaped apertures 216 of the air sealing cap (FIGS. 27B, 27C and 48A). Hence, when force is applied to the top section 230 of the sleeve 111, the legs 245 of the sleeve 111 abut portions of the rear outer ledge 259 and the long front outer ledge 260 which obscure portions of the "T" shaped apertures 216. Hence axial travel of the sleeve 111, and also therefore of the canister 114, is not possible. Rotation of the override element 115 results in rotation of the rear outer ledge 259 and the long front outer ledge 260 to positions where they no longer obscure portions of the "T" shaped apertures 216 of the air sealing cap (FIGS. 27D, 27E and 48B). Hence the legs 245 of the sleeve 111 can be accommodated in the "T" shaped apertures 216 (as shown in FIG. 48B), thereby allowing axial travel of the sleeve 111 and the canister 114.

Furthermore, the ratchets 234 of the override element 115 rotate past the clips 212 of the air sealing cap 106 (FIG. 48B). Additionally, rotation of the override element 115 causes the wedge 265 of the override element 115 (FIG. 25) to move from wedge slot 218 to wedge slot 219 of the air sealing cap 106 (FIG. 17). Once the ratchets 234 have rotated past the clips 212 and the wedge 265 is received by wedge slot 219, the override cannot be rotated anti-clockwise (i.e., to its starting position) due to the interference engagement between the ratchets 234 and the clips 212, and the wedge 265 with wedge slot 219, i.e., the override is irreversibly 'locked' in its second position. Importantly, the point at which the rear outer ledge 259 and the long front outer ledge 260 no longer obscure portions of the "T" shaped apertures 216 is after the ratchets 234 have rotated past the clips 212 and the wedge 265 has been received by the wedge slot 219. This prevents use of the refill assembly 110 as a "press and breath" inhaler by only partial rotation of the override.

Figure 49:
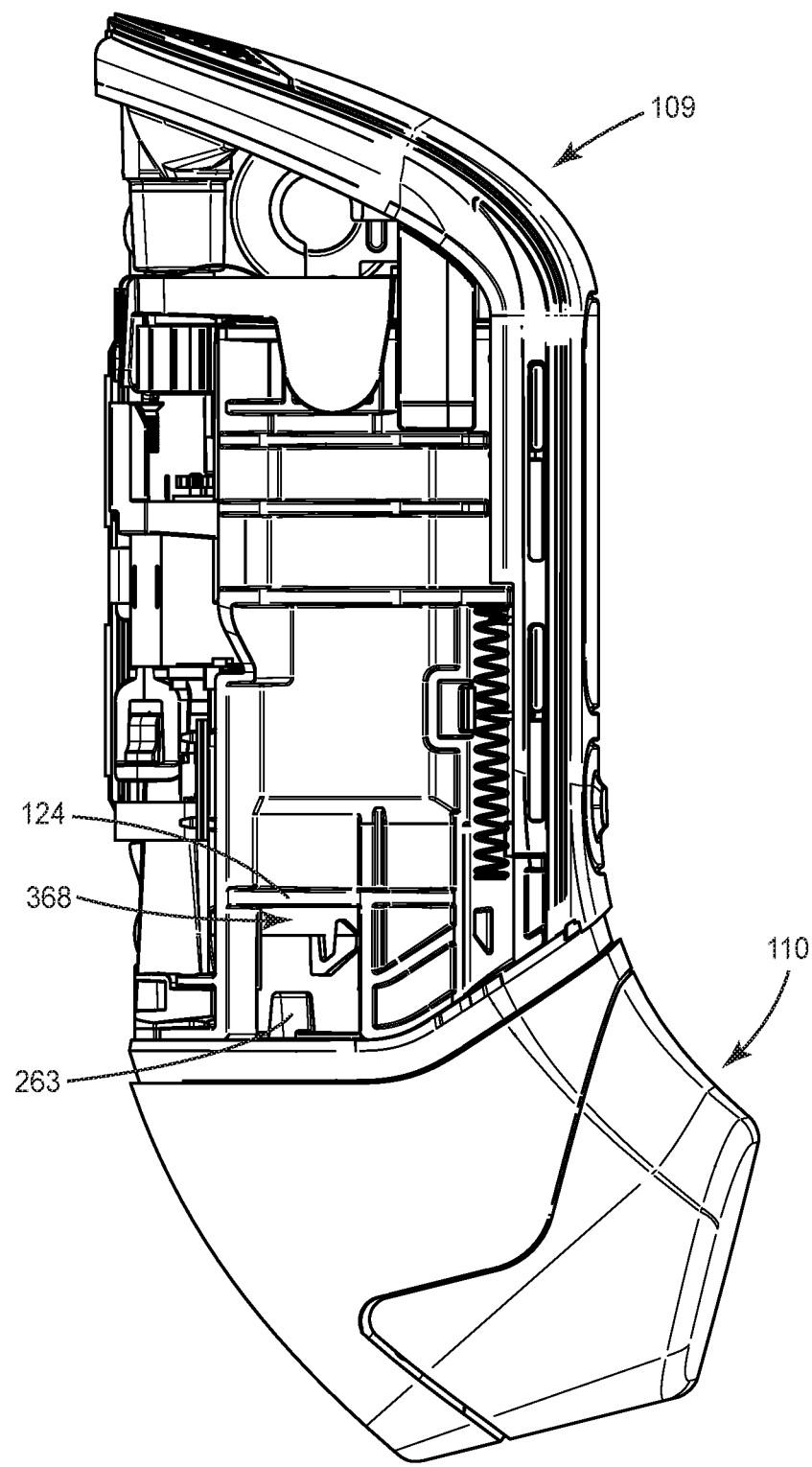
FIG. 49 is a side view of the inhaler of FIG. 2 with the rear outer housing removed.

Referring now to FIG. 49, once the override element 115 of the refill assembly 109 has been activated, the refill assembly 110 cannot ever again couple with a reusable assembly 109, as the boss 263 on the post 262 is now out of alignment and cannot be received by the recesses 368 of the chassis 124 of the reusable assembly 109. Hence the two can no longer be brought together, as shown in FIG. 49.

It is conceivable within the scope of the invention that the inhaler 100 may or may not include a flow governor.

What is claimed is:

1. A refill assembly for use in a medicinal inhaler, the refill assembly being configured to be removably coupled to a reusable assembly of a medicinal inhaler, the refill assembly comprising:
 a patient port;
 a canister configured to be actuable by the reusable assembly to deliver a dose of medicament to the patient port;
 a sleeve which is selectively actuable by a user independently of the reusable assembly so as to act on the canister to deliver a dose of medicament, the sleeve having a first position in which the sleeve cannot be actuated to cause a dose of medicament to be released from the canister and a second position in which the sleeve is actuable to cause a dose of medicament to be delivered to the patient port; and
 an override element which engages the sleeve, the override element being moveable from a first position in which the sleeve is retained in the first position by the override element and a second position in which the sleeve is permitted to move to the second position upon depression of the sleeve by a user;
 wherein the override element is movable from the first position to the second position and cannot be moved from the second position to the first position.

2. The refill assembly of claim 1, wherein the canister is actuable in the absence of the reusable assembly by depression of the sleeve by the user with the override element in the second position.

3. The refill assembly of claim 1, wherein the sleeve is configured to receive at least a portion of the canister, the canister comprising a medicament and a dose release valve, the sleeve movable between the first position in which the dose release valve is not actuated to release a dose of medicament and the second position in which the dose release valve is actuated to release the dose of medicament.

4. The refill assembly of claim 1, wherein the override element is configured to rotate between the first and second positions.

5. The refill assembly of claim 1, wherein the sleeve defines a protrusion for selectively engaging the override element.

6. The refill assembly of claim 5, wherein the protrusion engages an abutment on the override element when the sleeve and override element are in their respective first positions to prevent movement of the sleeve from the first position.

7. The refill assembly of claim 6, wherein the protrusion disengages from the abutment on the override element when the override element is moved from the first position to the second position permitting movement of the sleeve from the first position to the second position upon depression of the sleeve by the user.

8. The refill assembly of claim 7, wherein the sleeve has a cylindrical body and the protrusion is defined by at least one leg which extends from the cylindrical body.

9. The refill assembly of claim 8, wherein the abutment is defined by at least one ledge which is aligned with, and engages with, the at least one leg on the sleeve when the sleeve and override element are in their respective first positions.

10. The refill assembly of claim 9, wherein the at least one leg of the sleeve comprises three legs and the at least one ledge of the override element comprises three ledges, wherein the three legs are respectively aligned with the three ledges when the sleeve and override element are in their respective first positions.

11. The refill assembly of claim 1, wherein the override element includes a boss which is operable by the user to move the override element from the first position to the second position.

12. An inhaler comprising:
 the refill assembly of claim 1; and
 the reusable assembly,
 wherein the reusable assembly is configured to be coupled to the refill assembly, the reusable assembly comprising a dose release firing system configured to act on the canister to deliver the dose of medicament.

13. The inhaler of claim 12, wherein the refill assembly is releasable from the reusable assembly after the refill assembly has been coupled to the reusable assembly.

14. The inhaler of claim 12, wherein the dose release firing system is breath-actuated.

15. A refill assembly for use in a medicinal inhaler, the refill assembly being configured to be removably coupled to a reusable assembly of a medicinal inhaler, the refill assembly comprising:
 a patient port;
 a canister configured to be actuable by the reusable assembly to deliver a dose of medicament to the patient port;
 a sleeve which is selectively actuable by a user independently of the reusable assembly so as to act on the canister to deliver a dose of medicament, the sleeve having a first position in which the sleeve cannot be actuated to cause a dose of medicament to be released from the canister and a second position in which the sleeve is actuable to cause a dose of medicament to be delivered to the patient port; and
 an override element which engages the sleeve, wherein the override element is configured to receive at least a portion of the canister, the override element being moveable from a first position in which the sleeve is retained in the first position by the override element and a second position in which the sleeve is permitted to move to the second position upon depression of the sleeve by a user.

16. The refill assembly of claim 15, wherein the override element is movable from the first position to the second position and cannot be moved from the second position to the first position.

17. The refill assembly of claim 15, wherein the override element comprises an annular shape or an annular portion.

18. The refill assembly of claim 15, wherein the override element includes a boss which is operable by the user to move the override element from the first position to the second position.

19. An inhaler comprising:
 the refill assembly of claim 15; and
 the reusable assembly, wherein the reusable assembly is configured to be coupled to the refill assembly, the reusable assembly comprising a dose release firing system configured to act on the canister to deliver the dose of medicament.

20. The inhaler of claim 19, wherein the refill assembly is releasable from the reusable assembly after the refill assembly has been coupled to the reusable assembly.

* * * * *